US006083716A

United States Patent [19]
Wilson et al.

[11] Patent Number: 6,083,716
[45] Date of Patent: Jul. 4, 2000

[54] CHIMPANZEE ADENOVIRUS VECTORS

[75] Inventors: James M. Wilson, Gladwyne, Pa.;
Steven F. Farina, Chicago, Ill.;
Krishna J. Fisher, New Orleans, La.

[73] Assignee: The Trustees of the University of Pennsylvania, Philadelphia, Pa.

[21] Appl. No.: 08/923,137

[22] Filed: Sep. 4, 1997

Related U.S. Application Data

[60] Provisional application No. 60/024,700, Sep. 6, 1996.
[51] Int. Cl.[7] .................. C12P 21/00; C12N 15/861; C12N 5/10; C07H 21/04
[52] U.S. Cl. .............. 435/69.1; 435/320.1; 435/325; 435/366; 435/455; 435/456; 536/23.72; 424/93.2; 424/93.6
[58] Field of Search .................. 435/69.1, 172.1, 435/172.3, 320.1, 325, 366, 455, 456; 424/93.2, 93.6; 536/23.72

[56] References Cited

U.S. PATENT DOCUMENTS

| | | | |
|---|---|---|---|
| 4,920,209 | 4/1990 | Davis et al. | 435/235.1 |
| 5,543,328 | 8/1996 | McClelland | 435/320.1 |

FOREIGN PATENT DOCUMENTS

| | | |
|---|---|---|
| WO94/26914 | 11/1994 | WIPO . |
| WO 95/02697 | 1/1995 | WIPO . |
| WO 95/16048 | 6/1995 | WIPO . |
| WO 95/23867 | 9/1995 | WIPO . |
| WO 96/12030 | 4/1996 | WIPO . |
| WO96/13596 | 5/1996 | WIPO . |

OTHER PUBLICATIONS

Verma et al., Nature, vol. 389, pp. 239–242, Sep. 18, 1997.
Sprent et al., Science, vol. 265, pp. 1395–1399, Sep. 2, 1994.
M.B.A. Oldstone, Virology, vol. 234, pp. 179–185, 1997.
Orkin et al., "Report and Recommendations of the Panel to Assess the NIH Investment in Research on Gene Therapy", Dec. 7, 1995.
Rabinovich et al., Science, vol. 265, pp. 1401–1404, Sep. 2, 1994.
Cohen, Science, vol. 265, pp. 1371–1373, Sep. 2, 1994.
Chen et al., PNAS, vol. 94, pp. 1645–1650, Mar. 1997.
A. Kidd et al, "Human and Simian Adenoviruses: Phylogenetic Inferences from Analysis of VA RNA Genes", *Virology*, 207(1):32–45 (Feb. 20, 1995).
R. Wigand et al, "Chimpanzee Adenoviruses are Related to Four Subgenera of Human Adenoviruses", *Intervirology*, 30(1):1–9 (Jan./Feb., 1989).
M. Horowitz, "Adenoviridae and Their Replication", *Virology*, 2nd edit., ed. B.N. Fields, Raven Press, Ltd., New York, pp. 1679–1720 (1990).
K. Kozarsky et al., "Adenovirus–Mediated Correction of the Genetic Defect in Hepatocytes from Patient with Familial Hypercholesterolemia", *Somatic Cell and Molecular Genetics*, 19(5):449–458 (1993).

K. Kozarsky et al., "In Vivo Correction of Low Density Lipoprotein Receptor Deficiency in the Watanabe Heritable Hyperlipidemic Rabbit with Recombinant Adenoviruses", *Journal of Biological Chemistry*, 269(18):13695–13702 (May 6, 1994).

Y. Watanabe, "Serial Inbreeding of Rabbits with Heredity Hyperlipidemia (WHHL–Rabbit)", *Atherosclerosis*, 36:261–268 (1980).

K. Tanzawa et al., "WHHL–Rabbit: A Low Density Lipoprotein Receptor–Deficient Animal Model for Familial Hypercholesterolemia", *FEBS Letters*, 118(1):81–84 (Aug. 1980).

J. Goldstein et al., "Defective Lipoprotein Receptors and Atherosclerosis", *The New England Journal of Medicine*, 309(5):288–296 (Aug. 4, 1983).

S. Ishibashi et al., "Hypercholesterolemia in Low Density Lipoprotein Receptor Knockout Mice and its Reversal by Adenovirus–mediated Gene Delivery", *J. Clin. Invest.*, 92:883–893 (Aug. 1993).

S. Ishibashi et al., "Massive Xanthomatosis and Atherosclerosis in Cholesterol–Fed Low Density Lipoprotein Receptor–Negative Mice" *J. Clin. Invest.*, 93:1885–1893 (May 1994).

J. Wilson, "Vehicles for Gene Therapy", *Nature*, 365:691–692 (Oct. 21, 1993).

L. Prevec et al., "A Recombinant Human Adenovirus Vaccine against Rabies", *Journal of Infectious Diseases*, 161:27–30 (Jan. 1990).

T. Ragot, "Replication–Defective Recombiant Adenovirus Expressing the Epstein–Barr Virus (EBV) Envelope Glycoprotein GP340/220 Induces Protective Immunity Against EBV–induced Lymphomas in the Cottontop Tamarin", *Journal of General Virology*, 74:501–507 (1993).

M. Eloit et al., "Construction of a Defective Adenovirus Vector Expressing the Pseudorabies Virrus Glycoprotein gp50 and its Use as a Live Vaccine", *Journal of General Virology*, 71:2425–2431 (1990).

S.C. Jacobs et al., "High–Level Expression of the Tick–Borne Encephalitis Virus NS1 Protein by Using an Adenovirus–Based Vector: Protection Elicited in a Murine Model", *Journal of Virology*, 66:2086–2095 (Apr. 1992).

C.W. Beard et al., "Transcription Mapping of Mouse Adenovirus Type 1 Early Region 3", *Virology*, 175:81–90 (1990).

*Primary Examiner*—David Guzo
*Attorney, Agent, or Firm*—Howson and Howson

[57] ABSTRACT

A recombinant vector comprises chimpanzee adenovirus sequences and a heterologous gene under the control of regulatory sequences. A cell line which expresses chimpanzee adenovirus gene(s) is also disclosed. Methods of using the vectors and cell lines are provided.

30 Claims, 16 Drawing Sheets

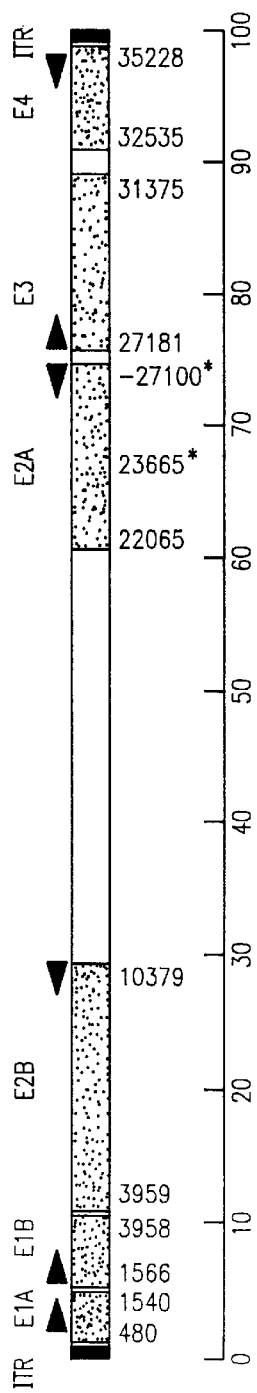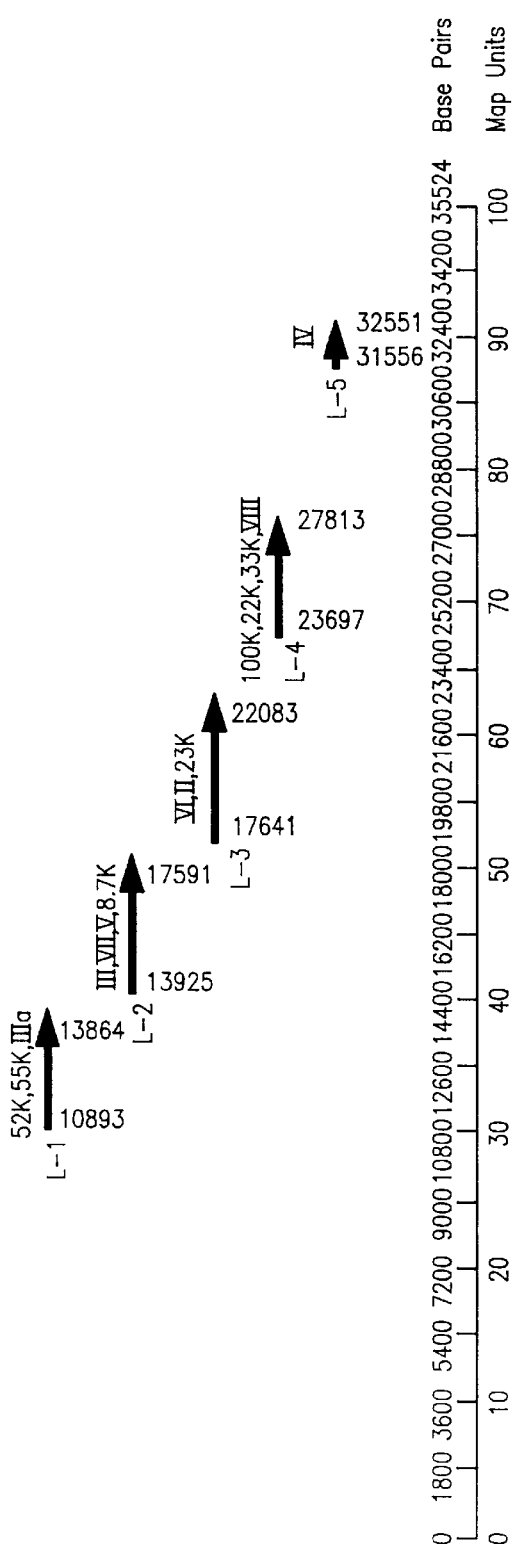
FIG. IA
FIG. IB

| Human Serotype<br>Sub-group<br>Chimp Virus | | C1 vs C68 | Ad-4<br>E<br>C1 | C68 | Ad-5<br>C<br>C1 | C68 | Ad-7<br>B<br>C1 | C68 | Ad-12<br>A<br>C1 | C68 | Ad-40<br>F<br>C1 | C68 |
|---|---|---|---|---|---|---|---|---|---|---|---|---|
| PROTEIN | C1/C68 aa | | | | | | | | | | | |
| E1 AND pIX regions | | | | | | | | | | | | |
| E1A 6/11K | 58/101 | 26[a] | 41 | 52[a] | 29 | 14[a] | 81 | 26[a] | 12 | NH[a] | NH | NH[a] |
| E1A 25K | 231/226 | 55 | 56 | 91 | 33 | 26 | 82 | 60 | 36 | 37 | 36 | 39 |
| E1A 28K | 262/257 | 57 | 57 | 92 | 34 | 34 | 83 | 61 | 37 | 40 | 34 | 40 |
| E1B 21K | 181/186 | 60 | 49 | 68[b] | 48 | 46 | 94 | 61 | 39 | 38 | 43 | 42 |
| E1B 55K | 495/498 | 74 | | | 53 | 57 | 88 | 73 | 46 | 46 | 46 | 47 |
| E1B 8.3K | 91/102 | 54 | | | 21 | 29 | 85 | 53 | 21 | 25 | 27 | 30 |
| pIX | 139/143 | 80 | | | 52 | 48 | 96 | 80 | 56 | 51 | 52 | 53 |
| E2 AND IVa2 regions | | | | | | | | | | | | |
| E2A DBP | 516/513 | 78 | 76 | 93 | 53 | 53 | 86 | 76 | 45 | 49 | 46 | 47 |
| E2B pTP | 643/628 | 91 | 90 | 94 | 81 | 80 | 96 | 90 | 75 | 76 | 73 | 73 |
| E2B pol | 1121/1125 | 90 | 83 | 92 | 75 | 76 | 96 | 90 | 72 | 72 | 68 | 69 |
| IVa2 | 448/448 | 93 | | | 82 | 82 | 96 | 92 | 76 | 77 | 80 | 80 |
| E3 region | | | | | | | | | | | | |
| E3A#1 | 106/106 | 78 | | | 52 | 58 | 96 | 78 | 66 | 70 | NH | NH |
| E3A#2 | 146/209 | 33[a] | | | NH | NH | 80 | 34 | NH | NH | NH | NH |
| E3A#3 | 172/176 | 60 | | | 38 | 32 | 75 | 60 | NH | NH | NH | NH |
| E3Hyp | 184/204 | 26 | | | NH | NH | 73 | 34 | NH | NH | NH | NH |
| E3Hyp | 188/204 | 31 | | | NH | NH | 82 | 31 | NH | NH | NH | NH |
| E3Hyp | 103/295 | NH | | | NH | NH | 48[a] | NH | NH | NH | NH | NH |
| E3B#4 | 91/91 | 71 | | | 47 | 48 | 92 | 77 | 44 | 41 | 37 | 36 |
| E3B#5 | 134/143 | 54 | | | 34 | 32 | 75 | 49 | 27 | 25 | 26 | 22 |
| E3B#6 | 135/135 | 79 | | | 52 | 54 | 91 | 80 | 52 | 52 | 46 | 48 |
| E4 region | | | | | | | | | | | | |
| E4 123/124 orf-1 | | 70 | | | 42 | 45 | | | 44 | 50 | NH | NH |
| E4 129/129 orf-2 | | 64 | | | 32[c] | 31[c] | | | 30 | 31 | 32 | 35 |
| E4 117/117 orf-3 | | 84 | | | 49 | 52 | | | 65 | 67 | 60 | 59 |
| E4 124/121 orf-4 | | 62 | | | 45 | 56 | | | 40 | 45 | 39 | 38 |
| E4 303/301 orf-6 | | 76 | | | 57 | 63 | | | 50 | 51 | 47 | 47 |
| E4 83/64 orf-7 | | 60 | | | 42 | 55 | | | 49 | 42 | 36 | 31 |
| LATE region | | | | | | | | | | | | |
| L1 16.6K 139/139 AngnoP | | 76 | | | 45 | 47 | 88 | 74 | 28 | 25 | 38 | 36 |
| L1 52/55K 389/391 | | 85 | | | 69 | 69 | | | 71 | 70 | 77 | 75 |
| L1 IIIa 586/592 | | 85 | | | 76 | 79 | | | 75 | 66 | 73 | 65 |
| L2 III 564/534 Penton | | 82 | | | 70 | 72 | 85 | 83[d] | 72 | 76 | 72 | 76 |
| L2 pVII 192/193 | | 91 | 87 | 96 | 73 | 70 | | | 76 | 74 | 73 | 72 |
| L2 pV 353/343 M.Core | | 84 | | | 58 | 61 | | | 63 | 67 | 60 | 61 |
| L2pMU 76/77 | | 91 | | | 69 | 73 | | | 65 | 64 | 72 | 65 |
| L3pVI 250/242 | | 79 | | | 65 | 68 | | | 66 | 58 | 57 | 49 |
| L3 II 956/933 Hexon | | 86 | 85 | 88 | 79 | 78 | 86 | 85 | 76 | 79 | 77 | 79 |
| L3 23K 207/206 EndoPr | | 89 | 78 | 88 | 75 | 76 | 93 | 87 | 79 | 80 | 78 | 82 |
| L4 100K 828/804 | | 80 | | | 62 | 65 | | | 61 | 64 | 59 | 62 |
| L4 22K 197/188 Mcrph | | 72 | | | 43 | 40 | | | 36 | 38 | 39 | 44 |
| L4 33K 231/222 | | 76 | | | 44 | 44 | | | NH | NH | 41 | 41 |
| L4 pVIII 227/227 Hex As | | 92 | 95 | 90[e] | 79 | 79 | 86 | 78[f] | 78 | 79 | 80 | 80 |
| L5 IV 322/425 Fiber | | 24[a] | 27[a] | 90 | 19[a] | 36[a] | 66 | 26[a] | 18[a] | 28[a] | 17[a] | 23[a] |

FIG. 2

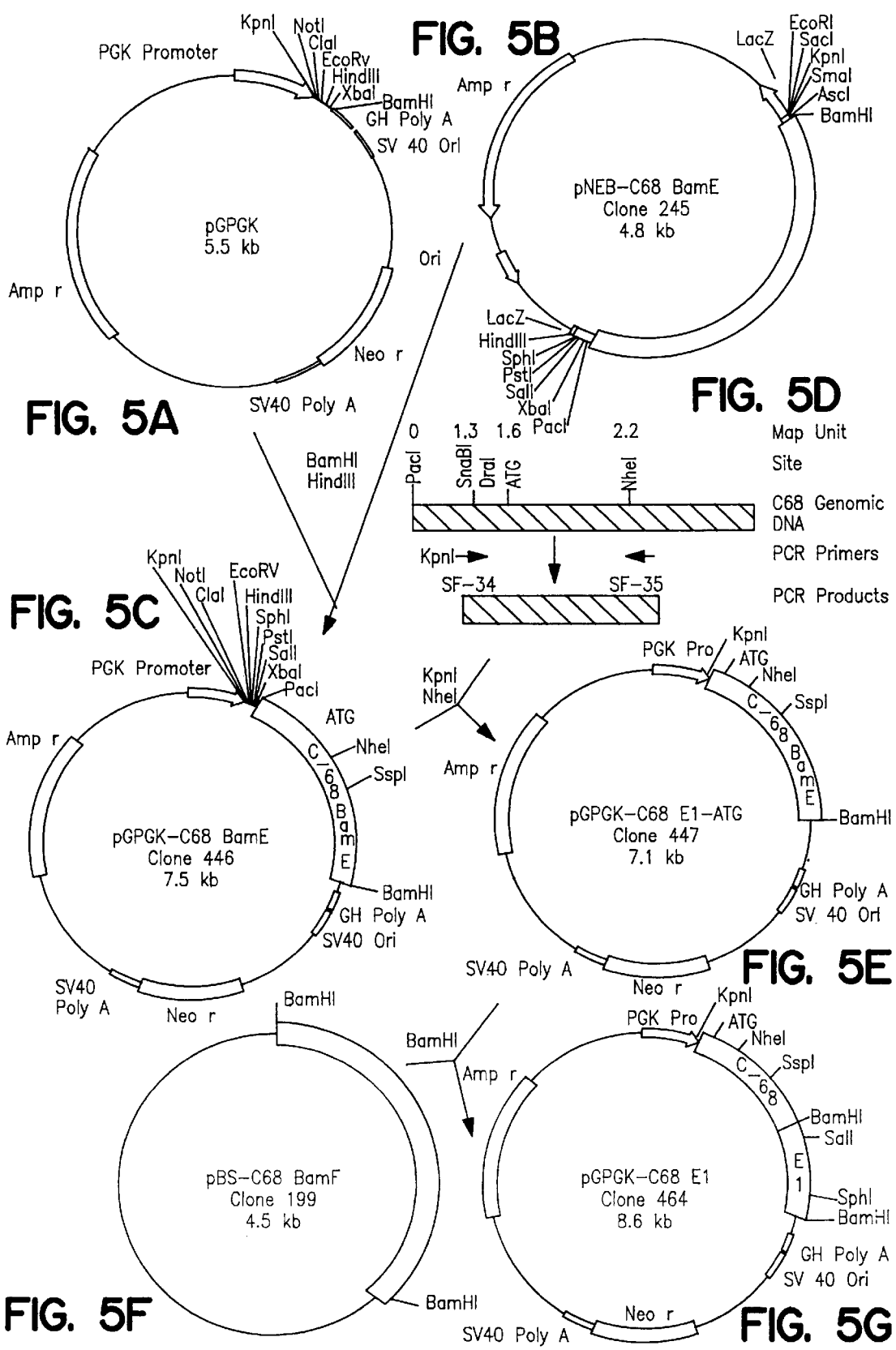

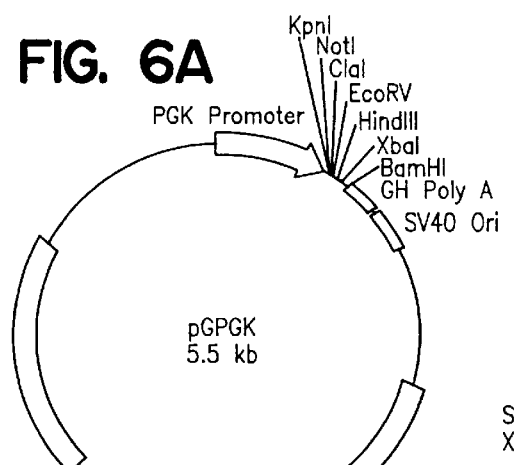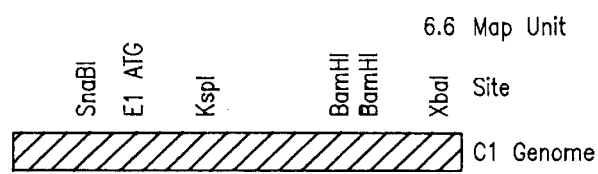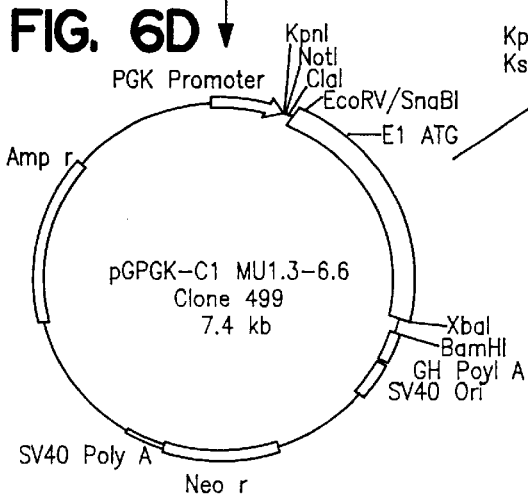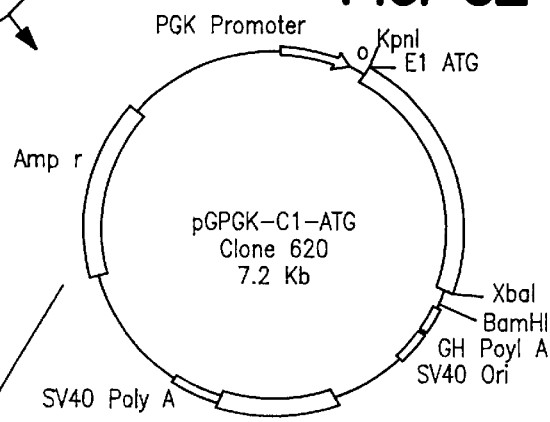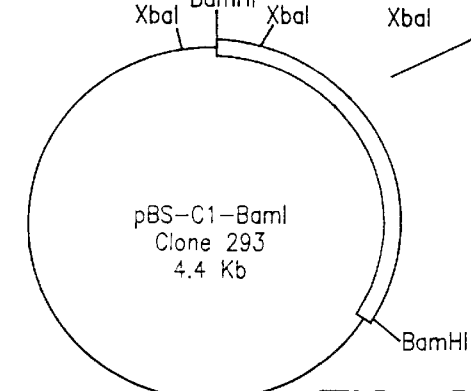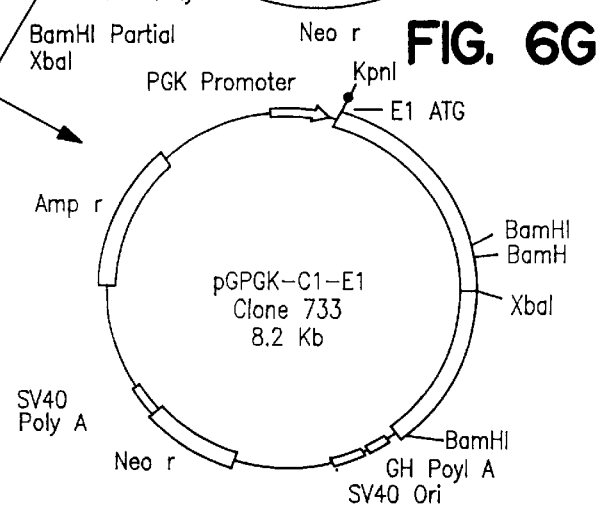

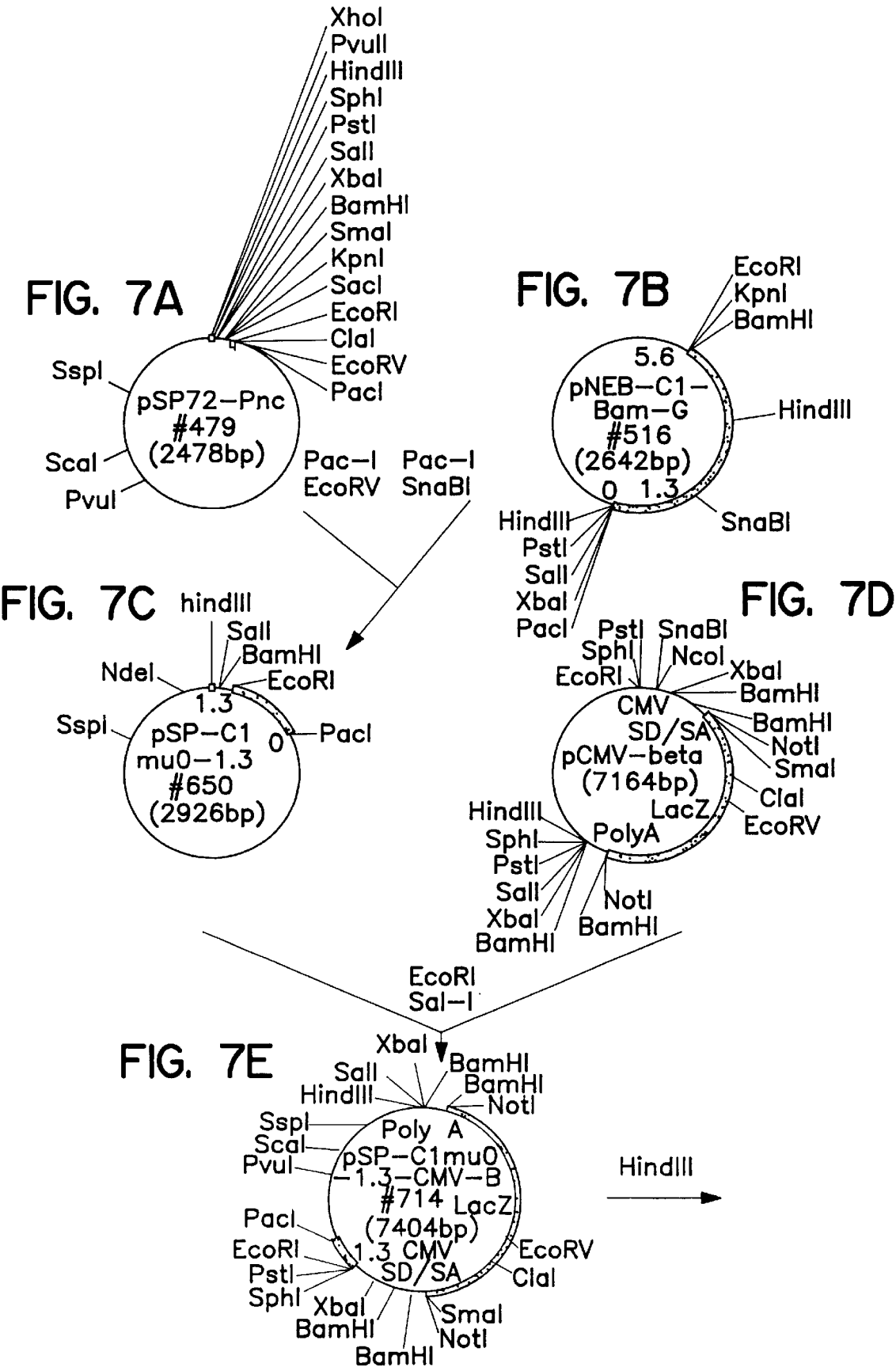

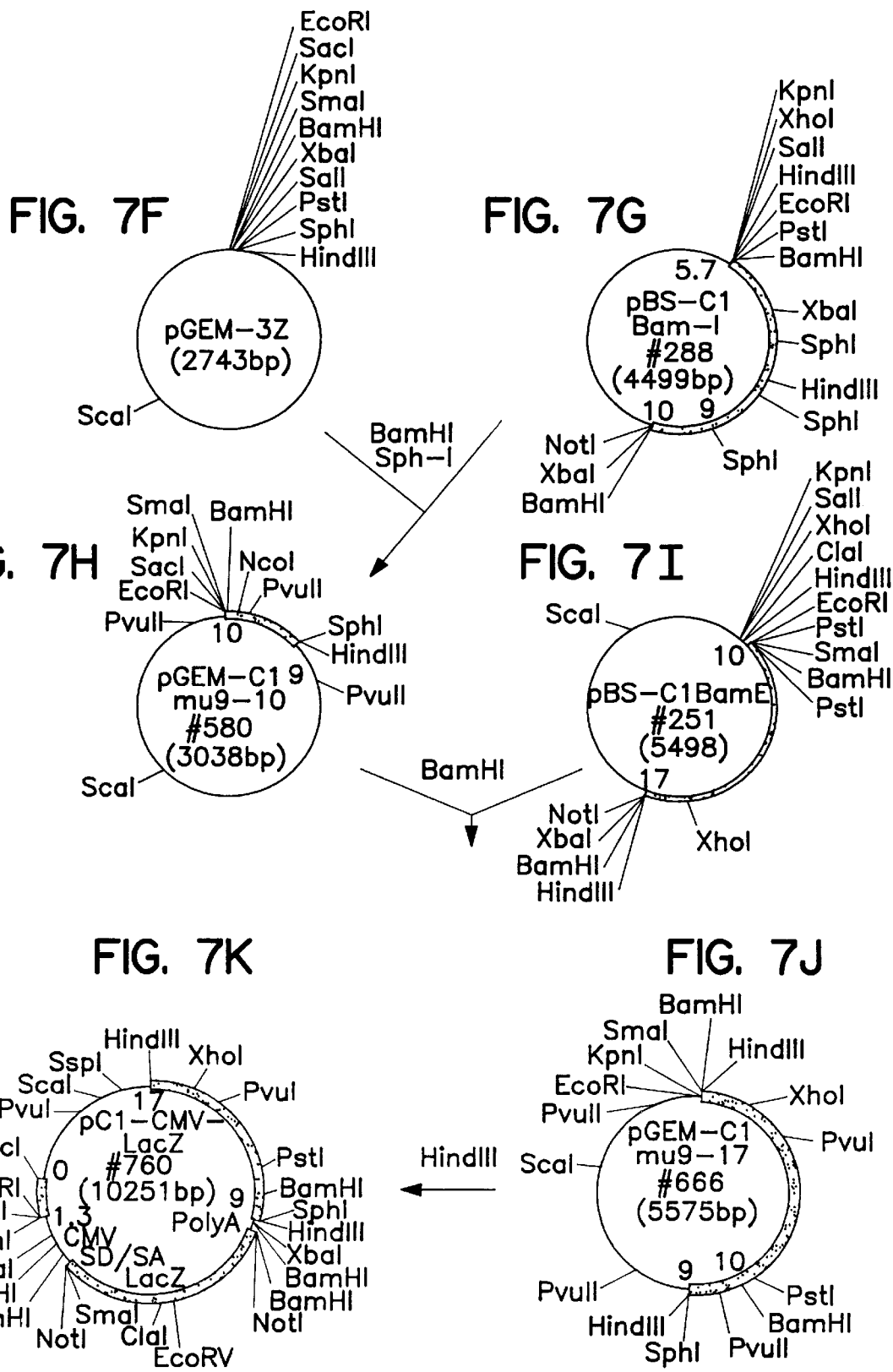

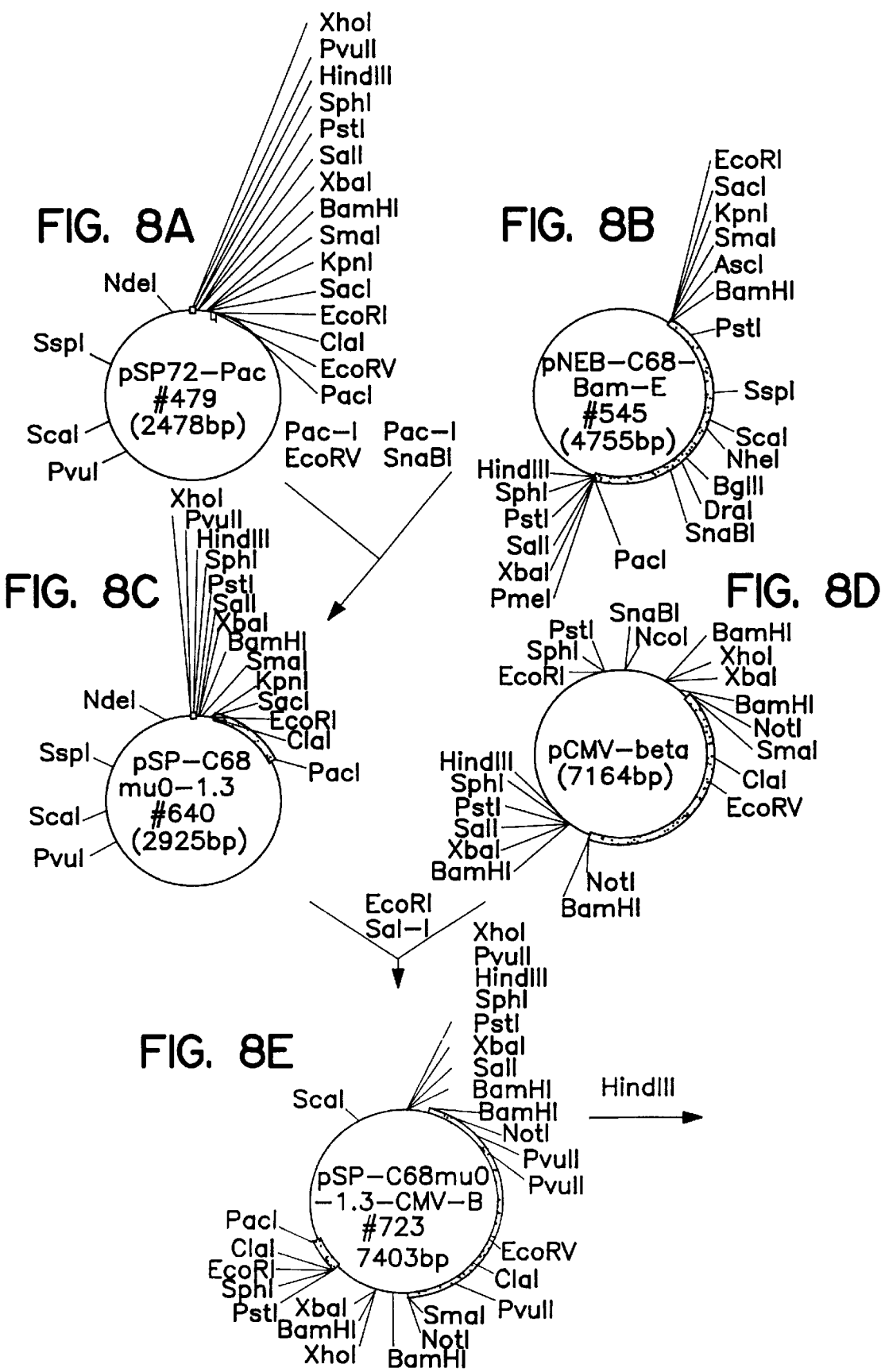

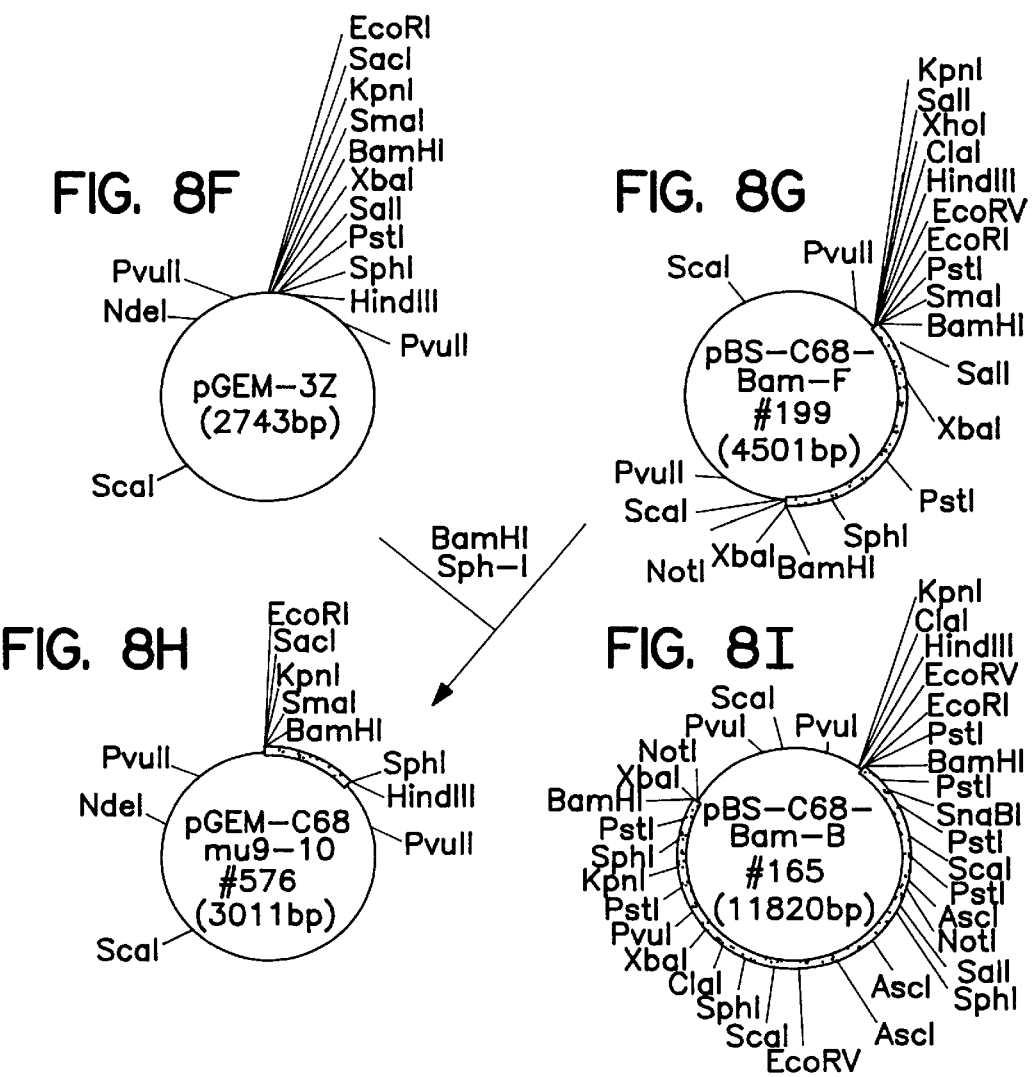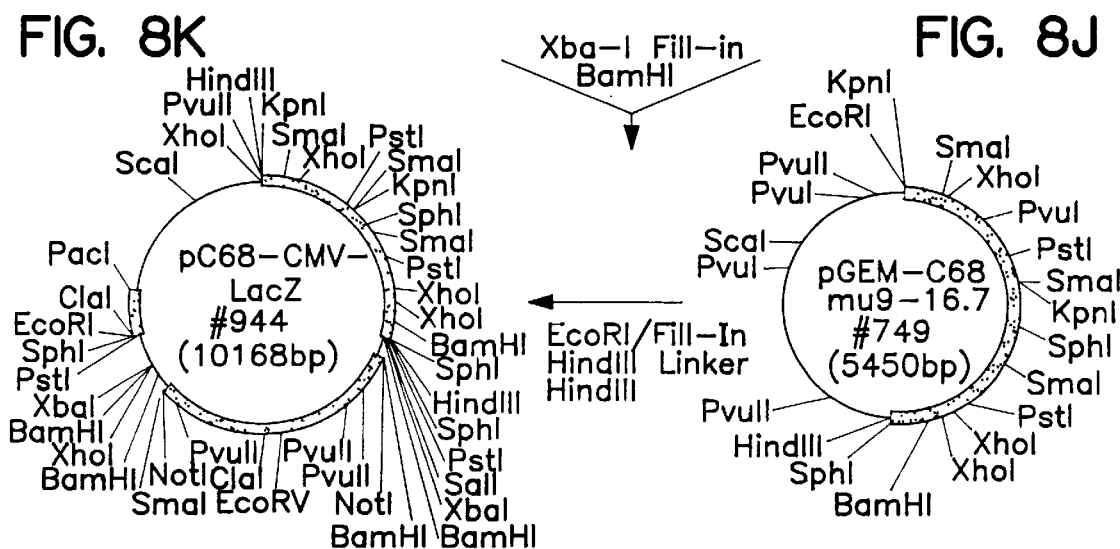

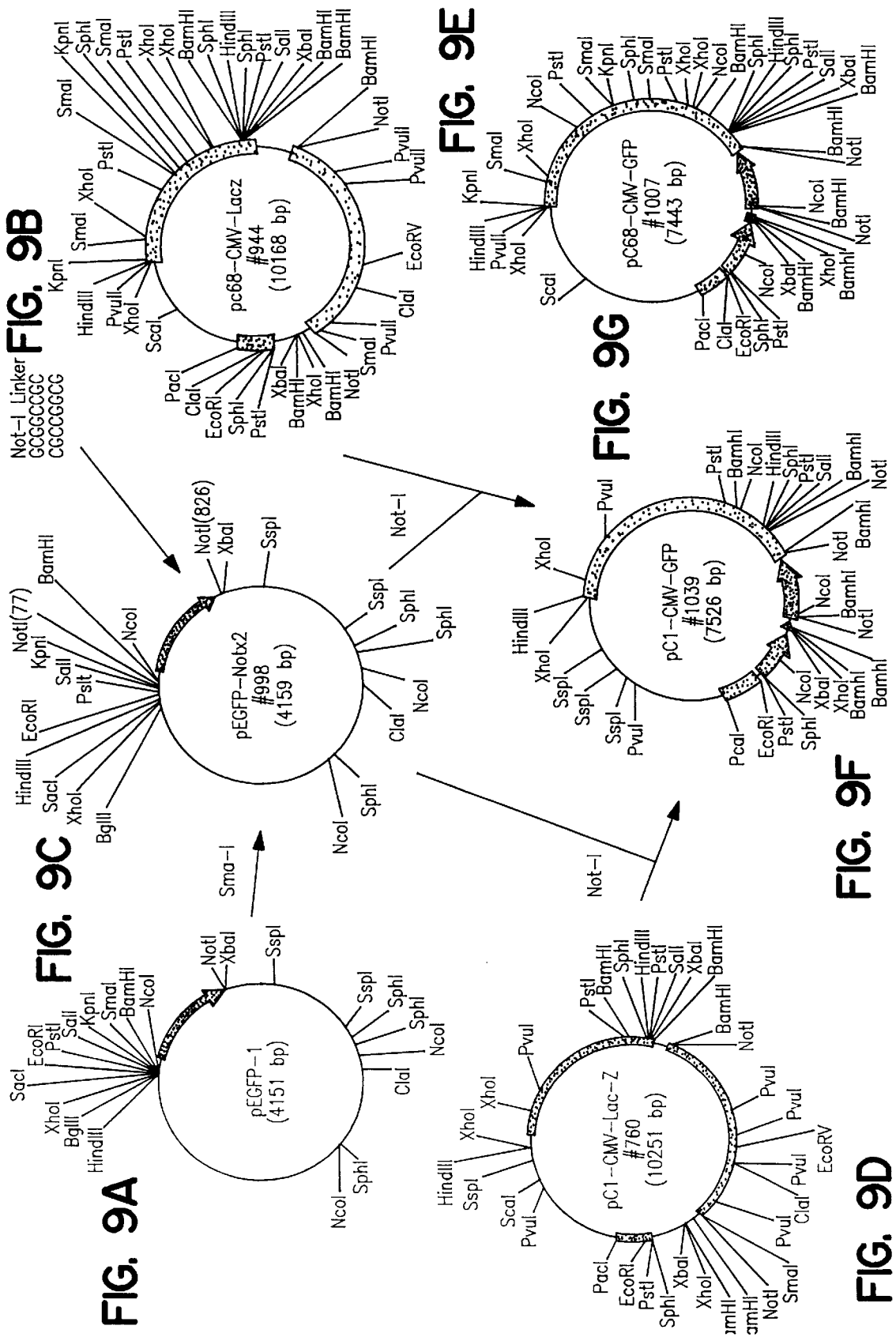

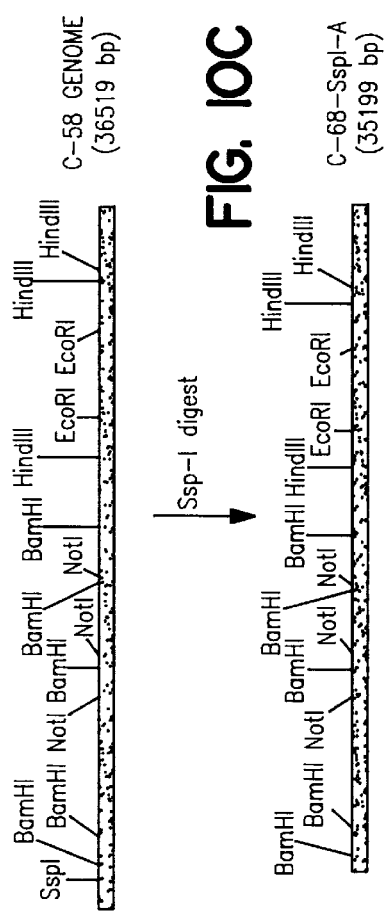
FIG. 10A
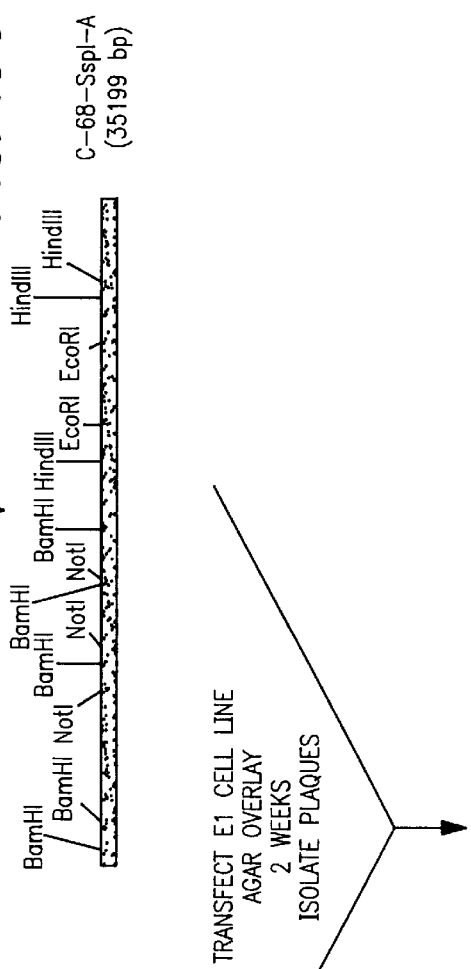
FIG. 10B
FIG. 10C
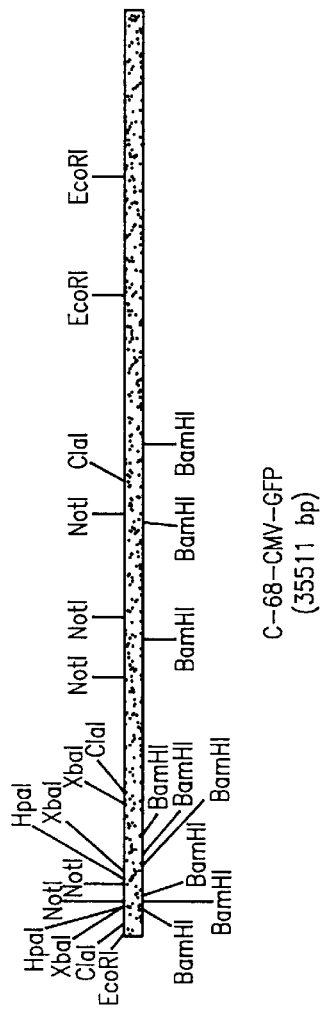
FIG. 10D

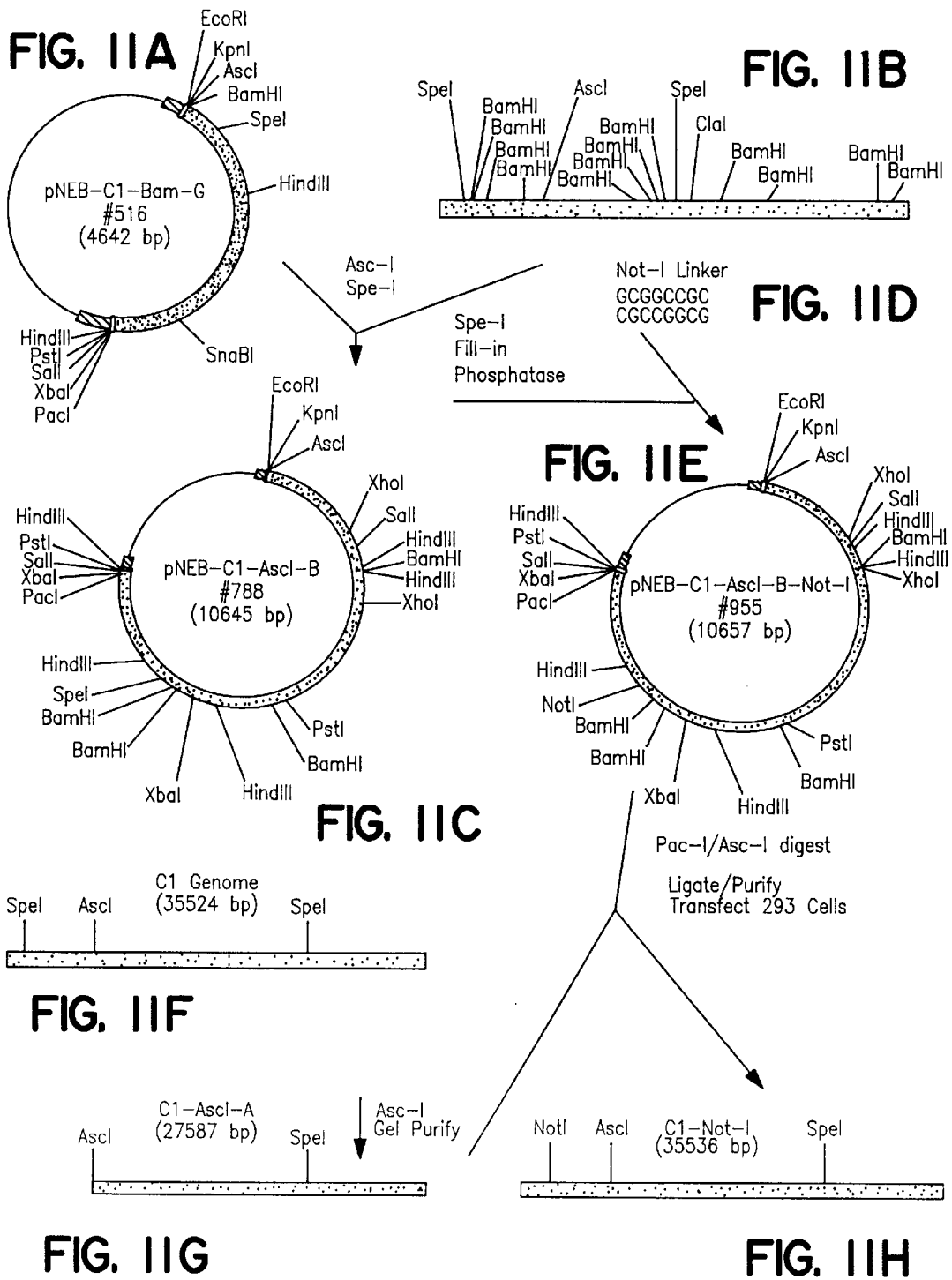

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
        (A) LENGTH: 35524 base pairs
        (B) TYPE: nucleic acid
        (C) STRANDEDNESS: double
        (D) TOPOLOGY: unknown (ii) MOLECULE TYPE: cDNA (xi) SEQUENCE DESCRIPTION: SEQ ID NO:1:

```
CCATCATCAA TAATATACCT TAAACTTTTG GTGCGTGTTA ATATGCAAAT GAGGCGTTTG      60

AATTTGGGGA GGGTGAAAGG TGATTGGCTG TGGGGACGGC GACCGTTAGG GGCGGGGCGG     120

GTGACGTTTT GATGACGTGG TCGTGAGGCG GAGTTGGTTT GCAAGTTCTC GTGGGAAAAG     180

TGACGTCAAA CGAGGTGTGG TTTGAACACG GAAATACTCA ATTTTCCCGC GCTCTCTGAC     240

AGGAAATGAT GTGTTTTTGG GCGGATGCAA GTGAAAATTC CTCATTTTCG CGCGAAAACT     300

AAATGAGGAA GTGAATTTCT GAGTAATTTC GTGTTTATGA CAGGGTGGAG TATTTACCGA     360

GGGCCGAGTA GACTTTGACC GATTACGTGG AGGTTTCGAT TACCGTGTTT TTCACCTAAA     420

TTTCCGCGTA CGGTGTCAAA GTCCTGTGTT TTTACGTAGG TGTCAGCTGA TCGCTAGAGT     480

ATTTAAACCT GACGAGTTCC GTCAAGAGGC CACTCTTGAG TGCCAGCGAG AAGAGTTTTC     540

TCCTCCGCAC TGCGAGTCAG ATCTCCACTT TGAAAATGAG ACACCTGCGC TTCCTGTCCC     600

AGGAGATAGT CTCCACTGAG ACTGGGAATG AAATACTGCA ATTTGTGGTA AATACACTGA     660

TGGGAGACGA TCCAGAGCCG CCTGAGCCAC CTTTTGATCC TCCTACGCTT CATGAATTAT     720

ATGATTTAGA GGTAGACGGA CCGGAGGACC CTAATGAAAA CGACGTGAAT GGGTTTTTTA     780

CTGATTCTAT GTTATTAGCT GCTAATGAGG GAGTGGATTT AGACCCACCT TCTGGAACTT     840

TTGATACTCC AGGGGTGATT GTGGAAAGCG ACATAGATGG GAAAAATTTA CCTGATTTGG     900

GTGCTGCTGA ATTGGACTTA TACTGCTATG AAGAGGGTTT TCCTCAGAGT GATGATGAAG     960

ATGTGGAGAA TGAGCAGTCA ATTCAGACCG CCGCGGGTGA GGGAGTGAAA GCTGCCAGTG    1020

ATGGTTTTAA GTTGGACTGT CCGGTGCTTC CTGGACATGG CTGTAAGTCT TGTGAATTTC    1080

ACAGGAAAAA TACTGGAGTA AAAGAAATAT TATGCTCGCT TTGTTATATG AGAGCGCATT    1140

GCCACTTTAT TTACAGTAAG TGTGTTTAAA GTTAAATTTA AAGGAACAGT AGCTGTTTTA    1200

ATAACTCTTG AATGGGTGAT TTATGTTTTG CTGATTTTTA TAGGTCCTGT GTCTGATGCT    1260

GATGAATCGC CTTCTCCTGA TTCAACTACC TCACCTCCTG AAATTCGGGC ACCCGTTCCT    1320

GCAAACGTAT GCAAGCCCAT TTCTGTGAAG CTTAAGCCTG GGAAACGCCC TGCTGTGAAT    1380

AAACTTGAGG ATTTGCTGGA GGGTGTGGAT GAACCTTTGG ACTTGTGTAC CCGGAAAATA    1440

CCAAGGCAAT GAGTGCTCCG CACCTGTGTT TATCTAATGT GACGTCACTG TTTTTGTGAG    1500

AGTGTCATGT AATAAAATTA TGTCAGCAGC TGAGTGTTTT ATTGTTTATT GGGTGGGACT    1560

TGGGATATAT AAGTAGGAGC AGACCTGTGT GGTTAGCTCA CAGCAGCTTG CTGCCATCCA    1620
```

```
                                   -continued

TGGAGGTTTG GGCCATATTG GAAGATCTTA GGCAGACTAG GCAACTGCTA GAAAACGCCT    1680

CGGACAGAGT CTCTGGTCTT TGGAGATTCT GGTTCGGTGG TGATCTAGCT AGACTAGTCT    1740

TTAGGATAAA GCAGGATTAC AGGCAAGAAT TTGAAAAGTT ATTGGACAAC TGTCCAGGAC    1800

TTTTTGAAGC TCTTAACTTG GGCCACCAGG CTCATTTTAA GGAGAAGGTT TTATCAGTTT    1860

TGGATTTTTC TACCCCTGGT AGAACTGCTG CTGCTGTAGC TTTCCTTACA TTTATATTTG    1920

ATAAATGGAT CCCACAGACC CACTTCAGCA AGGGATACGT TTTGGATTTC ATAGCAGCAG    1980

CTTTGTGGAA AACATGGAAG GCTCGCAGGA TGAGGACAAT CTTAGATTAC TGGCCAGTAC    2040

AGCCTCTGGG TGTAGCAGGG ATCCTGAGAC ACCCACCGAC CATGCCAGCG GTTTTGGAGG    2100

AGGTGCAACA AGAGGACAAT CCGAGAGCCG GCCTGGACCC TCCGGTGGAG GAGGCGGAGG    2160

AGTAGCTGAC TTGTTTCCTG AACTGCGACG GGTGCTTACT AGATCTACAA CCAGTGGGCG    2220

GGACAGGGGC ATTAAGAGGG AAAGGAATCC TAGTGGAACT AATCCCAGAT CTGAGTTGGC    2280

TTTAAGTTTG ATGAGTCGCA GACGTCCTGA AACTATATGG TGGCATGAGG TTCAGAATGA    2340

GGGCAGGGAT GAAGTATCAA TATTGCAAGA GAAATATTCT CTAGAACAGG TGAAAACATG    2400

TTGGTTGGAG CCTGAGGATG ATTGGGAGGT TGCCATTAGG AATTATGCCA AGATAGCTTT    2460

GAGGCCTGAT AAATTGTACA GAATTACTAA ACGGATTAAT ATTAGAAATG CATGCTATAT    2520

ATCAGGGAAT GGGGCTGAGG TAGTGATAGA CACTCAGGAC AGAACAGTTT TTAGATGCTG    2580

TATGATGGGT ATGTGGCCAG GGGTGATTGG CATGGAGGCG GTAACCTTTA TGAATGTAAA    2640

GTTTAGAGGG GATGGGTATA ATGGTGTGGT TTTTATGGCT AATACTAAAT TGATTTTGCA    2700

TGGTTGTAGC TTTTTTGGTT TTAATAATAT ATGTGTGGAA GCTTGGGGGC AGGTCAGTGT    2760

AAGAGGCTGT AGTTTCTATG CATGCTGGAT TGCAACATCA GGCAGGACCA AGAGTCAATT    2820

GTCTGTGAAG AAATGTATGT TTGAGAGATG TAACCTGGGC ATACTAAATG AAGGAGAAGC    2880

CAGAGTCAGC CACTGTGCTT CTTCCGAAAC TGGCTGTTTC ATGTTGATGA AGGGAAATGC    2940

CAATGTGAAA CATAATATGA TCTGCGGACC CTCAGATGAC AGGCCTTATC AGATGCTGAC    3000

ATGTGCTGGC GGACATTGCA ATATGCTGGC TACCGTGCAT ATTGTTTCTC ACCCACGCAA    3060

GAAATGGCCT GTTTTGGAAC ATAATGTGAT GACCAAATGT ACCATGCACG TAGGTGGACG    3120

CAGAGGAATG TTAATGCCAT ACCAGTGTAA CATGAATAAT GTGAAAGTGA TGTTGGAACC    3180

AGATGCATTT TCCAGAATGA GTTTAACAGG AATCTTTGAC ATGAATCTGC AAATATGGAA    3240

GATCCTGAGA TATGATGACA CGAAGTCGAG GGTACGCGCA TGCGAGTGCG GGGGCAAACA    3300

TGCCAGGTTC CAGCCGGTGT GTGTGGATGT GACTGAAGAA CTAAGGCCAG ATCATTTGGT    3360

GATTGCCTGC ACTGGAGCGG AGTTCGGTTC TAGTGGTGAA GAAACTGACT AAAGTGAGTA    3420

GTAGTGGGAT ACTTTGGATG GGCTCTTATG TGAATATGGT GGACAGATTG GGTAAATTTT    3480

GTTCTTTCTG TCTTGCAGCT GTCATGAGTG GAAGCGCTTC TTTTGAGGGG GGAGTCTTTA    3540

GCCCTTATCT GACGGGCCGT CTCCCACCAT GGGCAGGAGT TCGTCAGAAT GTCATGGGAT    3600

CCACTGTGGA TGGGAGACCA GTCCAGCCCG CCAATTCATC AACACTGACC TATGCCACTT    3660

TGAGCTCTTC ACCCTTGGAT GCAGCTGCAG CTGCTGCCGC TTCTGCTGCC GCCAATACCG    3720

TCCTTGGAAT TGGCTATTAT GGAAGCATCG TTGCCAATAC CAGTTCCTCA AATAACCCTT    3780

CGACCCTGGC TGAGGACAAG CTACTTGTTC TTTTGGCGCA GCTTGAGGCG TTGACCCAGC    3840

GCCTGGGTGA ACTGTCTCAG CAGGTGGCCC AGCTGCGCGA GCAAACTGAG TCTGCTGTTG    3900

CCACAGCAAA GTCTAAATAA AGATTAATCA ATAAATAAAG GAGATACTTG TTGATTTTAA    3960

ACTGTAATGA ATCTTTATTT GATTTTTCGC GCACGGTATG CCCTGGACCA CCGGTCTCGA    4020
```

```
TCATTGAGAA CTCGGTGGAT TTTTTCCAGG ACCCTGTAGA GGTGGGATTG AATGTTTAGA        4080

TACATGGGCA TTAGGCCGTC TCGGGGTGG AGATAGCTCC ATTGAAGAGC CTCATGCTCC         4140

GGGGTAGTAT TATAAATCAC CCAGTCATAA CAAGGTCGGA GTGCATGATG TTGCACAATA        4200

TCTTTAAGGA GCAGGCTGAT TGCAACTGGG AGCCCCTTGG TGTATGTGTT TACAAATCTG        4260

TTAAGCTGAG ATGGATGCAT TCTGGGTGAA ATTATATGCA TTTTTGACTG TATCTTGAGG        4320

TTGGCAATGT TGCCGCCCAG ATCCCGTCTC GGGTTCATGT TATGCAGGAC CACCAAGACG        4380

GTGTATCCGC TGCACTTAGG AAATTTATCA TGCAGCTTAG ATGGAAAAGC ATGAAAAAAT        4440

TTGGAGACGC CTTTGTGTCC GCCCAGATTC TCCATGCACT CATCCATGAT GATAGCGATG        4500

GGGCCGTGGG CGGCGGCACG GGCAAACACA TTCCGGTGGT CTGACACATC ATAGTTATGC        4560

TCCTGAGACA GGTCATCATA AGCCATTTTA ATAAACTTTG GCGGAGGGT GCCAGATTGG         4620

GGTATAAATG TACCCTCGGG CCCCGGAGCA TAGTTTCCCT CACAGATTTG CATTTCCCAG        4680

GCTTTCAATT CAGAGGGGGG GATCATGTCC ACCTGAGGGG CTATAAAAAA TACCGTTTCT        4740

GGGGCTGGGG TGATTAACTG TGATGATAGC AAATTCCTGA GCAGCTGTGA CTTGCCACAC       4800

CCAGTGGGGC CGTAAATGAC CCCGATTACG GGTTGCAGAT GGTAGTTTAG GGAGCGGCAG       4860

CTGCCGTCCT CTCGGAGCAG GGGGGCCACT TCGTTCATCA TTTCCCTTAC ATGGATATTT      4920

TCCCGCACCA AGTCCGTTAG GAGGCGCTCT CCACCTAGCG ATAAAAGTTC CTGGAGGGAG       4980

GAGAAGTTTT TGAGCGGCTT TAGCCCGTCA GACATGGGCA TTTTGGAAAG AGTCTGTTGC       5040

AAGAGCTCAA GCCGGTCCCA GAGCTCGGTA ATGTGTTCTA TGGCATCTCG ATCCAGCAGA       5100

CCTCCTCGTT TCGCGGGTTG GGACGGCTCC TGGAGTAGGG TATCAGACGA TGGGCGTCCA       5160

GCGCTGCCAG GGTCCGGTCT TTCCAGGGTC GCAGCGTCCG AGTCAGGGTT GTTTCCGTCA       5220

CAGTGAAGGG GTGCGCGCCT GGTTGGGCGC TTGCGAGGGT GCGCTTCAGG CTCATCCTGC       5280

TGGTCGAGAA CCGCTGCCGA TCGGCGCCCT GCATGTCAGC CATGTAGCAG TTTACCATGA       5340

GTTCGTAGTT GAGTGCCTCG GCTGCGTGAC CTTTGGCGCG GAGCTTACCT TTGGAAGTTT       5400

TCTGGCAGGC AGGGCAGTAC AGACACTTGA GGGCATATAG CTTGGGCGCG AGGAAGATTG       5460

ATTCGGGGGA GTATGCATCC GCGCCGCAGG AGGCGCAGAT GGTTTCGCAT TCCACGAGCC       5520

AGGTCAGATC CGGCTCATCG GGGTCAAAAA CAAGTTTACC GCCATGTTTT TTGATGCGCT       5580

TCTTACCTTT GGTCTCCATG AGTTCGTGTC CCCGCTGGGT GACAAAGAGG CTGTCCGTGT       5640

CCCCGTAGAC CGATTTTATG GGCCTGTCCT CGAGCGGAGT GCCTCGGTCC TCTTCGTAGA       5700

GGAACCCAGA CCACTCTGAT ACAAAGGCGC GCGTCCAGGC CAGTACAAAA GAGGCCACGT       5760

GGGAGGGGTA GCGGTCGTTA TCAACCAGGG GGTCCACCTT CTCCACAGTA TGTAAACACA       5820

TGTCCCCCTC CTCCACATCC AAGAAGGTGA TTGGCTTGTA AGTGTAGGCC ACGTGACCAG       5880

TTCCAGCCGG TGGGTATAA AAGGGGGCGG GTCTCTGCTC GTCCTCACTG TCTTCCGGAT         5940

CGCTGTCCAG GAGCGCCAGC TGTTGGGTA GGTATTCCCT TTCGAAGGCG GCATAACCT          6000

CTGCACTCAG GTTGTCAGTT TCTAGGAACG AGGAGGATTG GATATTGACA GTGCCAGTTG       6060

AGATGCCTTT CATGAGACTC TCGTCCATTT GGTCAGAAAA GACAATTTTC TTGTTGTCAA      6120

GCTTGGTGGC AAAGGATCCG TATAGGGCAT TGGATAAAAG CTTGGCGATG GAGCGCATGG       6180

TTTGGTTCTT ATCCTTGTCC GCACGCTCCT TGGCAGCAAT GTTGAGTTGG ACGTACTCGC       6240

GCGCCAGGCA CTTCCATTCA GGAAAGATGG TCGTCAGTTC ATCTGGCACG ATTCTGACTC       6300

GCCAGCCCCG ATTATGCAGG GTGATTAGAT CCACACTGGT GGCCACCTCG CCTCGGAGGG       6360
```

```
GCTCGTTGGT CCAGCAGAGT CGACCCCCTT TTCTTGAACA GAAAGGGGGG AGGGGGTCTA    6420

GCATGAGTTC ATCAGGGGGG TCTGCATCCA TGGTGAATAT TCCTGGGAGC AGATCTTTGT    6480

CAAAATAGCT AATGTGAGCG GGGTCATCCA AAGCCATCTG CCATTCTCGA GCTGCCAGCG    6540

CGCGTTCATA GGGATTGAGT GGGGTGCCCC ATGGCATGGG GTGGGTGAGT GCAGAGGCAT    6600

ACATGCCACA GATGTCATAG ACATACAGTG GTTCTTCGAG GATGCCGATG TAGGTGGGAT    6660

AACAGCGCCC CCCTCTGATG CTTGCTCGCA CATAGTCATA GAGTTCATGC GAGGGGGCGA    6720

GAAGACCCGG GCCCAGATTG GTACGGTTGG GTTTTTCAGC TCTGTAAACG ATCTGGCGAA    6780

AGATGGCATG GGAATTGGAA GAGATGGTAG GTCTCTGAAA GATGTTAAAA TGGGCATGAG    6840

GCAGGCCCAC AGAGTCCCTG ACGAAGTGGG CATAGGACTC TTGCAGCTTG GCCACCAGCT    6900

CGGCGGTGAC GAGCACATCC AGGGCGCAGT AGTCAAGGGT CTCTTGAATG ATGTCATAAC    6960

CTGGTTGGTT TTTCTTTTCC CACAGCTCGC GGTTGAGGAG GTATTCTTCG CGATCTTTCC    7020

AGTACTCTTC GAGGGAAAC CCGTCTTTGT CTGCACGGTA AGAGCCCAGC ATGTAGAACT    7080

GATTGACTGC CTTGTAGGGG CAGCATCCCT TCTCCACGGG GAGAGAGTAT GCTTGGGCGG    7140

CCTTGCGCAG AGAGGTATGA GTGAGGGCAA AGGTGTCCCT GACCATGACT TTAAGGAACT    7200

GATACTTGAA GTCGATGTCA TTACAGGCCC CCTGTTCCCA GAGTTGGAAG TCTACCCGCT    7260

TCTTGTAGGC GGGATTGGGC AAAGCGAAAG TAACATCGTT GAAGAGTATC TTGCCTGCCC    7320

TGGGCATGAA ATTGCGGGTG ATGCGGAAAG CTGGGCAC TTTTGCTCGG TTATTGATCA    7380

CCTGAGCGGC TAGGACGATC TCATCAAAGC CATTGATGTT GTGCCCCACT ATGTACAGTT    7440

CTATGAATCG AGGGGTGCCC TTGACATGAG GCAGCTTCTT AAGTTCTTCG AAAGTTAGGT    7500

CTGTGGGGTC AGAGAGAGCA TAGTGTTCGA GGGCCCATTC GTGCAGGTGA GGGTTCGCAT    7560

TGAGGAAGGA GGACCAAAGA TCCACTGCCA GTGCTGTTTG TAACTGGTCC CGGTACTGGC    7620

GAAAATGCTG GCCGACTGCC ATCTTTTCTG GGGTGACACA GTAGAAGGTT TTGGGGTCCT    7680

GCTGCCAGCG ATCCCACTTT AGTTTCATGG CGAGGTCGTA GGCGATGTTG ACGAGCCGCT    7740

CGTCCCCAGA GAGTTTCATG ACCAGCATGA AGGGTATGAG TTGCTTGCCA AAGGACCCCA    7800

TCCAGGTGTA GGTTTCCACA TCGTAGGTGA GGAAGAGCCT TTCCGTGCGA GGATGAGAGC    7860

CGATCGGGAA GAACTGGATC TCCTGCCACC AGTTGGAGGA ATGGCTGTTG ATGTGATGGA    7920

AGTAGAAATC CCTGCGGCGC GCCGAGCATT CATGCTTGTG CTTGTACAGA CGGCCGCAGT    7980

ACTCGCAGCG CTGCACGGGA TGCACCTCGT GAATGAGTTG TACCTGGCTT CCTTTGACGA    8040

GAAATTTCAG TGGGAAGTTG AGGCCTGGCG CTTTTACCTC GCTCTCTACT ATGTTATCTG    8100

CATCGGCCTG GCCATCTTCT GTCTCGATGG TGGTCATGCT AACAAGCCCC CGCGGGAGGC    8160

AAGTCCAGAC CTCGGCACGG GAGGGCGGA GCTCGAGGAC GAGAGCGCGC AGGCCGGAGC    8220

TGTCCAGGGT CCTGAGACGC TGCGGAGTCA GGTTAGTAGG TAGGGTGAGG AGATTGACTT    8280

GCATGATCTT TTCGAGGGCA AGCGGGAGGT TCAGATGGTA TTTGATCTCC ACGGGTCCGT    8340

TGGTGGAAAT GTCGATGGCT TGCAGGGTTC CGTGCCCTTT GGGCGCCACC ACCGTGCCCT    8400

TGTTTTTCCT TTTGGGCGGA GGCGGTGGTG TTGCTTCTTG CATGTTCAGA AGCGGTGGCG    8460

AGGGCGCGCG CCTGGCGGTA GAGGCGGCTC GGGCCCCGGC GGCATGGCTG GCAGTGGCAC    8520

GTCGGCGCCG CGCGCGGGTA GGTTCTGGTA CTGCGCCCTG AGAAGACTTG CGTGCGCGAC    8580

AACGCGGCGC TTGACGTCCT GGATCTGTCG CCTCTGGGTG AAAGCTACCG GCCCCGTGAG    8640

CTTGAACCTG AAAGAGAGTT CAACAGAATC AATCTCGGTA TCGTTGACGG CGGCTTGTCT    8700

TAGGATCTCT TGTACGTCGC CCGAGTTGTC CTGGTAGGCT ATCTCGGCCA TGAACTGCTC    8760
```

-continued

```
GATTTCTTCC TCCTGAAGAT CTCCGCGGCC TGCTCTCTCG ACGGTGGCCG CGAGGTCGTT    8820

GGAGATGCGA CCCATGAGTT GAGAGAATGC ATTCATGCCT GCCTCGTTCC AGACGCGGCT    8880

GTAGACCACG GCCCCCTCGG GATCTCTCGC GCGCATGACC ACCTGGGCGA GGTTGAGCTC    8940

CACGTGGCGG GTGAAGACCG CATAGTTGCA TAGGCGCTGG AAGAGGTAGT TGAGTGTGGT    9000

GGCGATGTGC TCGGTGACGA AGAAATACAT GATCCATCGT CTCAGCGGCA TCTCGCTGAC    9060

ATCGCCCAGG GCTTCCAAGC GTTCCATGGC CTCGTAAAAG TCCACGGCAA AGTTGAAAAA    9120

CTGGGAGTTG CGCGCGGACA CGGTCAACTC CTCCTCCAGA AGACGGATGA GTTCGGCGAT    9180

GGTGGCGCGC ACCTCGCGCT CGAAAGCTCC CGGGATTTCT TCCTCCTCTT CTTCTATCTC    9240

CTCTTCCACT AACATCTCTT CTTCCTCTTC AGGCGGGGGC GGAGGAGGAG GGGGCACGCG    9300

GCGACGCCGG CGGCGCACGG GCAAACGGTC GATGAATCTT TCAATGACCT CTCCGCGGCG    9360

GCGGCGCATG GTCTCGGTGA CGGCACGGCC GTTTTCCCTG GGTCTCAGAG TGAAGACGCC    9420

TCCGCGCATC TCCCTAAAGT GGTGACTGGG GGGCTCTCCG TTGGGCAGGG ACAGAGCGCT    9480

GATTATGCAT TTTATCAATT GCCCCGTAGG GACTCCGCGC AAGGACCTGA TCGTCTCAAG    9540

ATCCACGGGA TCGGAAAACC TTTCGACGAA AGCGTCTAAC CAGTCGCAAT CGCAAGGTAG    9600

GCTGAGCACT GTTTCTTGTA GGCGGGGGTG GCTACACGCT CGGTCGGGGT TCTCTATTTC    9660

TTCTCCTTCC TCCTCTCGGG AGGGTGAGAC GATGCTGCTG GTGATGAAAT TAAAATAGGC    9720

AGTTCTGAGA CGGCGGATGG TGGCGAGGAG CACCAGGTCT TTGGGACCGG CTTGCTGGAT    9780

GCGCAGGCGA TTGGCCATTC CCCAAGCATT ATCCTGGCAC CTGGCCAGAT CTTTGTAGTA    9840

GTCTTGCATA AGTCGCTCCA CGGGCACTTC TTCTTCGCCC GCTCTGCCAT GCATGCGCGT    9900

GAGCCCAAAC CCGCGCATGG GCTGGACAAG TGCCAGGTCC GCTACGACCC TTTCTGCGAG    9960

GATGGCTTGC TGCACCTGGG TGAGGGTGGC TTGGAAGTCG TCAAAGTCCA CAAAGCGATG   10020

GTAGGCCCCG GTGTTGATGG TGTAAGAGCA GTTGGCCATG ACTGACCAGT TGACTGTCTG   10080

GTGCCCCGGG CGCACAATCT CGGTGTACTT GAGGCGCGAG TAGGCGCGGG TGTCAAAGAT   10140

GTAATCGTTG CAGGCGCGCA CCAGGTACTG GTAGCCGATT AGAAAATGTG GTGGCGGCTG   10200

GCGGTATAGG GGCCATCGCT CTGTAGCCGG GGCGCCAGGA GCGAGGTCTT CCAGCATGAG   10260

GCGGTGATAA CCGTAGATGT ACCTGGACAT CCAGGTGATA CCGGAGGCGG TGGTGGATGC   10320

CCGAGGGAAC TCGCGTACGC GGTTCCAGAT GTTGCGCAGC GGCATGAAGT AGTTCATGGT   10380

AGGCACGGTT TGGCCCGTGA GGCGCGCACA GTCGTTGATG CTCTAGACAT ACGGGCAAAA   10440

ACGAAAGCGG TCAGCGGCTC GACTCCGTGG CCTGGAGGCT AAGCGAACGG GTTGGGCTGC   10500

GCGTGTACCC CGGTTCGAAT CTCGGATTAG GCTGGAGCCG CAGCTAACGT GGTACTGGCA   10560

CTCCCGTCTC GACCCAAGCC TGCACAAAAC CTCCAGGATA CGGAGGCGGG TCGTTTTTTT   10620

TTTTTTTGCT TTTCCTGGAT GGGAGCCAGT GCTGCGTCAA GCTTTAGAAC GCTCAGTTCT   10680

CGGGCCTGGG AGTGGCTCGC GCCCGTAGTC TGGAGAATCA ATCGCCAGGG TTGCGTTGCG   10740

GCATGCCCCG GTTCGAGTCT TAGCGCGCCG GATCGGCCGG TTTCCGCGGC AAACGAGGGT   10800

TTGGCAGCCC CGTCATTTCT AAGACCCCGC TAGCCGACTT CTCCAGTTTA CGGGAGCGAG   10860

CCCTCTTTTT TTTTTTTGTT TTTGTTGCCC AGATGCATCC CGTGCTGCGA CAGATGCGCC   10920

CCCAGCAACA GCCCCCTTCT CAGCAGCAGC CACAGCAACA GCCACAAAAG GCTCTTCCTG   10980

CTCCTGTAAC TACTGCAGCT GCAGCCGTCA GCGGCGCGGG ACAGCCCGCC TATGATCTGG   11040

ACTTGGAAGA GGGCGAGGGA CTGGCGCGTC TGGGTGCACC ATCGCCCGAG CGGCACCCGC   11100
```

```
GGGTGCAACT GAAAAAGGAT TCTCGCGAGG CGTACGTGCC GCAGCAGAAC CTGTTCAGGG    11160

ACAGGAGCGG TGAGGAGCCG GAGGAAATGC GAGCTTCCCG CTTTAACGCG GGTCGCGAGC    11220

TGCGTCATGG TCTGGACCGA AGACGGGTGC TGCGCGATGA TGATTTTGAA GTCGATGAAG    11280

TGACAGGGAT AAGTCCTGCT AGGGCACATG TGGCTGCGGC CAACCTAGTA TCAGCCTACG    11340

AGCAGACCGT GAAGGAGGAG CGCAACTTTC AAAAATCTTT CAACAATCAT GTGCGCACCC    11400

TGATTGCCCG CGAGGAGGTG ACACTGGGTC TAATGCACCT GTGGGACCTG ATGGAAGCTA    11460

TTACCCAGAA CCCCACCAGC AAACCTCTGA CCGCTCAGCT GTTTCTAGTG GTGCAACATA    11520

GCAGAGACAA TGAGGCATTT AGGGAGGCGC TGTTGAACAT CACTGAGCCC GAGGGGAGAT    11580

GGTTGTATGA TCTTATCAAT ATTCTGCAAA GTATCATAGT GCAAGAACGT AGCCTGGGTC    11640

TGGCTGAGAA GGTGGCTGCT ATTAACTACT CGGTCTTAAG CCTGGGCAAG CACTACGCTC    11700

GCAAGATCTA TAAAACCCCA TACGTACCTA TAGACAAGGA GGTTAAGATA GATGGGTTTT    11760

ATATGCGCAT GACTCTCAAG GTGCTGACCT TGAGTGACGA TCTGGGAGTG TACCGCAACG    11820

ACAGGATGCA CCGTGCAGTG AGCGCCAGCA GAAGGCGTGA GCTGAGCGAC AGAGAACTTA    11880

TGCACAGCTT GCAAAGAGCT CTGACGGGGG CTGGAACCGA GGGGAGAAC TACTTTGACA     11940

TGGGAGCGGA TTTGCAATGG CAGCCCAGTC GCAGGGCCCT GGACGCAGCA GGGTATGAGC    12000

TTCCTTACAT AGAAGAGGCG GATGAAGGCC ATGACGAGGA GGGCGAGTAC CTGGAAGACT    12060

GATGGCGCGA CCATCCATAT TTTTGTTAGA TGCAGCAACA GCCACCTCCT GATCCCGCAA    12120

TGCGGGCGGC GCTGCAGAGC CAGCCGTCCG GCATTAACTC CTCGGACGAT TGGACCCAGG    12180

CCATGCAACG CATCATGGCG CTGACGACCC GCAACCCCGA AGCCTTTAGA CAGCAACCCC    12240

AGGCCAACCG CCTTTCTGCC ATCCTGGAGG CCGTAGTGCC CTCCCGCTCC AACCCCACCC    12300

ACGAGAAGGT CCTGGCTATC GTGAACGCGC TGGTGGAGAA CAAAGCCATA CGTCCCGATG    12360

AGGCTGGACT GGTATACAAT GCCCTATTGG AGCGCGTAGC CCGTTACAAC AGCAGCAACG    12420

TGCAGACCAA CCTTGACCGG ATGGTGACCG ATGTGCGCGA GGCTGTGTCT CAGCGCGAGC    12480

GGTTCCAGCA AGACTCCAAT CTAGGGTCGC TGGTGGCGTT GAACGCCTTC CTCAGCACCC    12540

AGCCTGCCAA CGTGCCTCGC GGCCAGCAAG ACTACACAAA CTTTCTAAGT GCATTAAGAC    12600

TCATGGTGGC CGAAGTCCCT CAAAGTGAGG TGTACCAGTC CGGGCCAGAC TACTTTTTCC    12660

AGACCAGCAG ACAGGGCTTG CAGACAGTGA ACCTGAGCCA GGCTTTTAAG AACCTGAATG    12720

GTCTGTGGGG AGTGCGTGCC CCAGTAGGAG ATCGGGCAAC CGTGTCTAGC TTGCTAACCC    12780

CCAACTCCCG CCTACTACTG CTCTTGGTAG CCCCATTCAC TGACAGCGGT AGCATCGACC    12840

GCAATTCTTA CTTGGGCTAT TTGTTGAACC TGTATCGCGA GGCCATAGGG CAAACTCAGG    12900

TAGATGAGCA AACCTATCAA GAAATTACCC AAGTGAGCCG CGCTCTGGGT CAGGAAGACA    12960

CTGGCAGCTT GGAAGCCACC TTAAACTTCT TGCTGACCAA CCGGTCGCAG AAGATCCCTC    13020

CTCAGTATGC GCTTACCGCG GAGGAGGAAC GAATCCTGAG ATACGTGCAG CAGAGCGTGG    13080

GACTTTTCCT AATGCAGGAG GGGGCGACTC CTACTGCTGC GCTAGATATG ACAGCCCGAA    13140

ACATGGAGCC CAGCATGTAT GCCAGTAACA GGCCTTTTAT CAATAAACTA CTAGACTACT    13200

TACACAGGGC GGCTGCTATG AACTCTGATT ATTTCACCAA TGCTATACTG AACCCCCATT    13260

GGCTGCCCCC ACCTGGGTTC TATACGGGCG AGTATGACAT GCCCGACCCC AATGACGGGT    13320

TTTTATGGGA CGATGTGGAC AGTAGTGTTT TCTCCCCGCC TCCTGGTTAT AACACTTGGA    13380

AGAAGGAAGG GGGCGATAGA AGGCATTCTT CCGTATCGCT GTCCGGGGCA ACGGGTGCTG    13440

TCGCAGCGGT GCCCGAGGCC GCAAGTCCTT TCCCTAGTTT GCCATTTTCG CTAAACAGTG    13500
```

```
TACGCAGCAG TGAGCTGGGC AGGATCACGC GTCCGCGCTT GATGGGCGAG GAGGAGTACT   13560

TGAATGACTC GCTGTTGAGG CCAGAGCGGG AGAAGAACTT CCCCAATAAC GGGATAGAGA   13620

GCCTGGTGGA TAAGATGAGC CGCTGGAAGA CGTACGCGCA CGAGCACAGG GACGAGCCCC   13680

GAGCTAGCAG CAGCGCCGGC GCCCGTAGAC GCCAGCGGCA CGATAGGCAG CGGGGACTTG   13740

TGTGGGACGA TGAGGATTCC GCCGACGACA GCAGCGTGTT GGACTTGGGT GGGAGTGGTG   13800

GTGGTAACCC GTTTGCTCAC CTGCGCCCCC GCGTTGGGCG CCTGATGTAA AAACCGAAAA   13860

TAAATGGTAC TCACCAAGGC CATGGCGACC AGCGTGCGTT CGTTTCTTCT CTGTTGTATC   13920

TAGTATGATG AGGCGAACCG TGCTAGGAGG AGCGGTGGTG TATCCGGAGG GTCCTCCTCC   13980

TTCGTATGAA AGCGTGATGC AGCAGGCGGC GGCGGCGGCG ATGCAGCCAC CACTGGAGGC   14040

TCCCTTTGTC CCCCCTCGGT ACCTGGCACC TACGGAGGGG AGAAACAGCA TTCGTTACTC   14100

GGAGCTGGCA CCATTGTATG ATACCACCCG GTTGTATTTG GTGGACAACA AGTCGGCGGA   14160

CATCGCCTCA CTGAACTATC AGAACGACCA CAGCAACTTC CTCACCACGG TGGTGCAAAA   14220

CAATGACTTT ACCCCCACGG AGGCCAGCAC CCAGACAATC AACTTTGACG AGCGGTCGCG   14280

ATGGGGTGGT CAGCTGAAGA CTATCATGCA CACCAACATG CCCAACGTGA ACGAGTACAT   14340

GTTTAGCAAC AAGTTCAAAG CTCGGGTGAT GGTGTCCAGA AAGGCTCCTG AAGGTGTCAC   14400

AGTAGATGAC AATTATGATC ACAAGCAGGA TATTTTGGAA TATGAGTGGT TTGAGTTTAC   14460

TCTACCGGAA GGCAACTTCT CAGCCACAAT GACCATTGAC CTAATGAACA ATGCCATCAT   14520

TGATAATTAC CTTGAAGTGG GCAGACAGAA TGGAGTGTTG GAGAGTGACA TTGGTGTTAA   14580

ATTTGACACC AGGAACTTTA AACTGGGTTG GGATCCGGAA ACTAAGTTGA TTATGCCTGG   14640

GGTTTACACC TATGAGGCAT TCCATCCTGA CATTGTATTG TTGCCTGGTT GTGGGGTTGA   14700

CTTTACTGAA AGTCGCCTTA GTAACTTGCT TGGTATCAGG AAAAGACACC CATTCCAGGA   14760

GGGTTTTAAG ATCTTGTATG AGGATCTTGA AGGGGGTAAT ATCCCAGCCC TTTTGGATGT   14820

AGAAGCCTAT GAGAACAGTA AGAAAGAACA AGAAGCCAAA ACAGAAGCCG CTAAAGCTGC   14880

TGCTATTGCT AAAGCCAATA TAGTTGTCAG CGACCCTGTC AGGGTGGCTA ATGCCGAAGA   14940

AGTCAGAGGA GACAACTATA CAGCTACATC TGTTGCAACT GAAGAATCGC TATTGACTAC   15000

TGCTGCGACT GGAACCAAAA ATACAGAGAC AGGACTCACT ATCAAACCTG TAGAAAAAGA   15060

TAGCAAGAGT AGAAGTTACA ATGTCTTGGA AGATAAAGTT AATACAGCCT ACCGCAGCTG   15120

GTATCTGTCC TACAACTATG GCGACCCTGA AAAAGGAGTC CGTTCCTGGA CACTGCTCAC   15180

CACCTCGGAT GTCACCTGTG GAGCAGAGCA GGTGTACTGG TCACTTCCAG ACATGATGCA   15240

GGACCCTGTC ACATTCCGTT CCACGAGACA AGTCAGCAAC TATCCAGTGG TAGGTGCAGA   15300

GCTCATGCCA GTCTTCTCAA AAAGTTTCTA CAACGAGCAA GCCGTGTACT CCCAGCAGCT   15360

TCGCCAGTCC ACCTCGCTCA CGCACGTCTT CAACCGCTTC CCTGAGAACC AGATCCTCAT   15420

CCGCCCGCCA GCGCCCACCA TTACCACCGT CAGTGAAAAC GTTCCTGCTC TCACAGATCA   15480

CGGGACCCTG CCGTTGCGCA GCAGTATCCG GGGAGTCCAG CGCGTGACCG TTACTGACGC   15540

CAGACGCCGC ACCTGCCCCT ACGTCTACAA GGCCCTGGGC ATAGTCGCGC CGCGCGTCCT   15600

TTCAAGCCGC ACTTTCTAAA AAAAAAAAAA TGTCCATTCT TATCTCACCT AGTAATAACA   15660

CCGGTTGGGG CCTGCGCGCG CCAAGCAAGA TGTACGGAGG TGCTCGCAAA CGCTCTACAC   15720

AGCACCCTGT GCGAGTGCGC GGACACTTCC GCGCTCCATG GGGCGCCCTC AAGGGCCGTA   15780

TCCGCACTAG AACCACCGTC GATGATGTGA TCGACCAGGT GGTGGCCGAT GCTCGTAATT   15840
```

```
ATACTCCTAC TGCACCTACA TCTACTGTGG ATGCAGTTAT TGACAGCGTA GTAGCTGACG    15900

CCCGCGCCTA TGCTCGCCGG AAGAGCAGGC GGAGACGCAT CGCCAGGCGC CACCGGGCTA    15960

CTCCCGCTAT GCGAGCAGCA AGAGCTTTGC TACGGAGAGC CAAACGCGTG GGGCGAAGAG    16020

CTATGCTTAG AGCAGCCAGA CGCGCGGCTT CAGGTGCCAG TGCTGGCAGG TCCCGCAGGC    16080

GCGCAGCCAC TGCAGCAGCA GCGGCCATTG CCAACATGGC CCAACCGCGA AGAGGCAATG    16140

TGTACTGGGT GCGCGACGCC ACCACCGGCC AGCGCGTGCC CGTGCGCACC CGTCCCCCTC    16200

GCTCTTAGAA GATACTGAGC AGTCTCCGAT GTTGTGTCCC AGCGAGGATG TCCAAGCGCA    16260

AATACAAGGA AGAGATGCTC CAGGTCATCG CGCCTGAAAT CTACGGTCCG CCGGTGAAGG    16320

ATGAAAAAAA GCCCCGCAAA ATCAAGCGGG TCAAAAAGGA CAAAAAGGAA GAAGATGGCG    16380

ATGATGGTCT GGTGGAGTTT GTGCGCGAGT TCGCCCCAAG GCGGCGTGTG CAGTGGCGTG    16440

GACGCAAAGT GCGGCCTGTG CTGAGACCTG GAACCACGGT GGTCTTTACG CCCGGCGAGC    16500

GCTCCAGCAC TGCTTTTAAG CGGTCCTATG ATGAGGTGTA TGGGGATGAT GATATTCTGG    16560

AGCAGGCGGC TGACCGCCTG GGCGAGTTTG CTTATGGCAA GCGCTCCCGC TCCAGTCCCA    16620

AGGAGGAGGC GGTGTCCATT CCCTTGGACA ATGGGAATCC CACCCCTAGC CTCAAGCCAG    16680

TCACCCTGCA GCAAGTGCTG CCCGTGCCTC CACGCAGAGG CATCAAGCGA GAGGGTGAGG    16740

ATCTGTATCC CACTATGCAA TTGATGGTGC CCAAGCGCCA GCGGCTGGAG GACGTGCTGG    16800

AGAAAATGAA AGTGGATCCC GATATACAAC CTGAGGTCAA AGTGAGACCC ATCAAGCAGG    16860

TGGCGCCAGG TTTGGGAGTA CAAACCGTAG ACATCAAGAT TCCAACCGAG TCCATGGAAG    16920

TCCAAACCGA ACCTGCAAAG CCCACAACCA CCTCCATTGA GGTACAAACG GATCCCTGGA    16980

TGTCAGCACC CGTTACAACT CCAGCTGCCG TCAACACCAC TCGAAGATCC CGGCGACAGT    17040

ACGGTCCAGC AAGTTTGCTG ATGCCAAATT ATGCTCTGCA CCCATCTATT ATTCCAACTC    17100

CGGGTTACCG AGGCACTCGC TACTACCGCA GCCGGAGCAG TACTTCCCGC CGTCGCCGCA    17160

AAACACCTAC AAGTCGTAGT CACCGTCGTC GCCGTCGCCC CACCAGCAAT CTGACTCCCG    17220

CTGCTCTGGT GCGGAGAGTG TATCGCGATG GCCGCGCGGA TCCCATGACG TTGCCACGCG    17280

TACGCTACCA CCCAAGCATC ACAACTTAAC GACTGTTGCC GCTGCCTCCT TGCAGATATG    17340

GCCCTCACTT GCCGCCTTCG TGTCCCCATT ACTGGCTACC GAGGAAGAAA CTCGCGCCGT    17400

AGAAGAGGGA TGTTGGGGCG CGGGATGCGA CGCCACAGGC GGCGGCGCGC TATCAGCAAG    17460

AGGCTGGGGG GTGGCTTTCT GCCTGCTCTG ATCCCCATCA TAGCCGCGGC GATCGGGGCG    17520

ATACCAGGCA TAGCTTCCGT GGCGGTTCAG GCCTCGCAGC GCCACTGACA TTGGAAAAAC    17580

TTATAAATAA AACAGAATGG ACTCTGATGC TCCTGGTCCT GTGACTATGT TTTTGTAGAG    17640

ATGGAAGACA TCAATTTTTC ATCCCTGGCT CCGCGACACG GCACGAGGCC GTACATGGGC    17700

ACCTGGAGCG ACATCGGCAC CAGCCAACTG AACGGGGGCG CCTTCAATTG GAGCAGTATC    17760

TGGAGCGGGC TTAAAAATTT TGGCTCTACC ATAAAAACCT ATGGGAACAA AGCTTGGAAC    17820

AGCAGCACAG GGCAGGCACT GAGAAATAAG CTTAAAGAAC AAAACTTCCA ACAGAAGGTG    17880

GTTGATGGGA TCGCCTCTGG TATTAATGGG GTGGTGGATC TGGCCAACCA GGCCGTGCAG    17940

AAACAGATAA ACAGCCGCCT GGACCCGCCG CCGTCAGCCC CGGGTGAAAT GGAAGTGGAG    18000

GAAGATCTCC CTCCCCTTGA AAAACGGGGC GACAAGCGTC CGCGCCCCGA TCTGGAGGAG    18060

ACACTAGTCA CACGCTCAGA CGACCCGCCC TCCTACGAGG AGGCAGTGAA GCTTGGAATG    18120

CCCACCACCA GGCCTGTAGC CCCCATGGCT ACCGGGGTGA TGAAACCTTC TCAGTCACAC    18180

CGACCCGCTA CCTTGGACTT GCCTCCTCCC CCTGCTGCTG CAGCGCCTGC TCGCAAGCCT    18240
```

```
GTCGCTACCC CGAAGCCCAC CACCGTACAG CCCGTCGCCG TAGCCAGACC GCGTCCTGGG   18300

GGCGGCCCAC GACCGAATTC AAACTGGCAG AGTACTCTGA ACAGCATCGT TGGTCTGGGC   18360

GTGCAAAGTG TAAAACGCCG TCGCTGCTTT TAAATTAAAT ATGGAGTAGC GCTTAACTTG   18420

CCTGTCTGTG TGTATGTGTC ATCATCACGC CGCTGCCGCA GCAACAGCAG AGGAGAAAGG   18480

AAGAGGTCGC GCGCCGAGGC TGAGTTGCTT TCAAGATGGC CACCCCATCG ATGCTGCCCC   18540

AGTGGGCATA CATGCACATC GCCGGACAGG ATGCTTCGGA GTACCTGAGT CCGGGTCTGG   18600

TGCAGTTCGC CCGCGCCACA GACACCTACT TCAATCTGGG GAACAAGTTT AGGAACCCCA   18660

CCGTGGCGCC CACCCATGAT GTGACCACCG ACCGCAGTCA GCGGCTGATG CTGCGCTTTG   18720

TACCCGTTGA CCGGGAGGAC AATACCTACT CATACAAAGT TCGATACACC TTGGCTGTGG   18780

GCGACAACAG AGTGCTGGAT ATGGCCAGCA CTTTCTTTGA CATTCGGGGT GTGTTGGATA   18840

GAGGCCCTAG CTTCAAGCCA TATTCTGGCT CTGCTTACAA CTCATTGGCC CCTAAGGGCG   18900

CTCCCAATAC ATCTCAGTGG CTTGATAAGG GAGTCACAAC CACTGATAAT AATACTGAAA   18960

ACGGAGATGA AGAAGATGAA GTTGCCGAGG AAGGGGAAGA AGAAAAACAA GCTACATACA   19020

CTTTTGGCAA TGCGCCAGTA AAAGCCGAAG CTGAAATTAC AAAAGAAGGA CTGCCAATAG   19080

GTTTGGAAGT TCCATCTGAA GGTGACCCTA AACCCATTTA TGCTGATAAA CTGTATCAGC   19140

CAGAACCTCA GGTGGGAGAG GAATCTTGGA CTGATACGGA TGGCACAGAT GAAAAATATG   19200

GAGGCAGAGC ACTTAAACCT GAAACTAAAA TGAAACCCTG CTACGGGTCT TTTGCTAAAC   19260

CTACTAATGT TAAAGGCGGC AAGCAAAAG TGAAGAAAGT AGAAGAAGGC AAGGTTGAAT   19320

ATGACATTGA CATGAACTTT TTCGACCTAA GATCACAAAA GACTGGTCTC AAGCCTAAAA   19380

TTGTAATGTA TGCAGAAAAT GTGGATCTAG AAACTCCAGA CACTCATGTG GTGTACAAAC   19440

CTGGAGCTTC AGATGCTAGT TCTCATGCAA ACCTTGGTCA ACAGTCCATG CCCAATAGAC   19500

CTAACTATAT TGGCTTCAGG GACAACTTCA TCGGACTCAT GTACTATAAC AGTACTGGCA   19560

ACATGGGAGT GCTGGCTGGA CAAGCGTCTC AGCTAAATGC AGTGGTTGAC TTGCAAGACA   19620

GAAACACAGA ATTGTCATAT CAACTCTTGC TTGATTCTCT GGGAGACAGA ACCAGATATT   19680

TCAGCATGTG GAATCAAGCA GTGGATAGCT ATGACCCAGA TGTGCGTGTT ATTGAAAACC   19740

ATGGTGTGGA AGATGAACTT CCCAACTATT GTTTTCCATT GGACGGTGTA GGTCCGCGAA   19800

CAGACAGTTA CAAGGGAATT GAGACAAATG GTGACGAAAA CACTACTTGG AAAGATTTAG   19860

ATCCAAATGG CATAAGTGAA CTTGCTAAGG GAAATCCATT TGCCATGGAA ATCAACATCC   19920

AAGCTAATCT CTGGAGAAGT TTCCTTTATT CCAACGTGGC CCTCTATCTC CCAGACTCGT   19980

ACAAATACAC TCCAACCAAT GTTACTCTCC CAGAAAACAA AAACACCTAT GACTACATGA   20040

ATGGGCGGGT GGTTCCCCCC TCCCTGGTGG ATACCTACGT AAACATTGGC GCCAGATGGT   20100

CTTTGGATGC CATGGACAAC GTCAACCCCT TCAACCATCA CCGCAACGCT GGCCTGCGAT   20160

ACCGGTCCAT GCTTCTGGGC AATGGTCGCT ACGTGCCTTT CCACATTCAA GTGCCTCAGA   20220

AATTCTTTGC TGTGAAAAAC CTGCTGCTTC TACCTGGTTC TTACACCTAC GAGTGGAACT   20280

TCAGAAAGGA TGTGAACATG GTCCTGCAGA GTTCCCTTGG CAATGATCTC GAGTTGATG   20340

GCGCCAGCAT CAGTTTTACC AGCATCAATC TCTATGCCAC CTTCTTCCCC ATGGCCCACA   20400

ACACTGCCTC CACCCTTGAA GCCATGCTGC GCAACGACAC CAATGATCAA TCATTCAATG   20460

ACTACCTTTC TGCAGCTAAC ATGCTCTACC CCATCCCTGC CAATGCTACC AACGTTCCCA   20520

TCTCCATTCC CTCTCGCAAC TGGGCCGCCT TCAGGGGCTG GTCCTTTACC AGACTGAAAA   20580
```

```
CCAAGGAGAC TCCCTCTTTG GGATCAGGGT TCGATCCCTA CTTTGTTTAC TCTGGTTCTA    20640

TACCCTACCT GGATGGTACC TTCTACCTCA ACCACACTTT CAAGAAAGTC TCTATCATGT    20700

TTGACTCTTC AGTCAGCTGG CCTGGTAATG ACAGATTGCT AACTCCAAAC GAGTTCGAAA    20760

TCAAGCGCAC AGTTGATGGG GAAGGCTACA ATGTGGCCCA ATGTAACATG ACCAAAGACT    20820

GGTTTCTGGT CCAGATGCTT GCCAACTACA ACATTGGATA CCAGGGTTTC TATGTTCCTG    20880

AGGGTTACAA GGATCGCATG TATTCCTTCT TCAGAAACTT CCAGCCCATG AGTAGACAGG    20940

TGGTTGATGA GATTAACTAC AAAGACTATA AAGCTGTCGC CGTACCCTAC CAGCATAATA    21000

ACTCTGGCTT TGTGGGTTAC ATGGCTCCTA CCATGCGTCA GGGTCAAGCG TACCCTGCTA    21060

ACTACCCATA CCCCCTAATT GGAACCACTG CAGTAACCAG TGTCACCCAG AAAAAATTCC    21120

TGTGTGACAG GACCATGTGG CGCATCCCAT TCTCTAGCAA CTTCATGTCC ATGGGTGCCC    21180

TTACAGACCT GGGACAGAAC TTGCTGTACG CCAACTCAGC CCATGCGCTG GACATGACTT    21240

TTGAGGTGGA TCCCATGGAT GAGCCCACCC TGCTTTATCT TCTTTTCGAA GTATTCGACG    21300

TGGTCAGAGT GCACCAACCA CATCGCGGCG TCATCGAGGC CGTCTACCTG CGCACACCGT    21360

TCTCGGCTGG TAACGCCACC ACATAAGAAA CCTGCTTCTT GCAAGGGGCA GCCATGACCT    21420

GCGTGACCGG AAACGGCTCC AGCGAGCAAG AGCTCAGAGC CATCGTCCGA GACCTTGGCT    21480

GTGGACCCTA TTTTCTGGGA ACCTTTGACA AACGCTTCCC GGGGTTTATG GCTCCAGACA    21540

AGCTGGCCTG CGCCATTGTC AACACAGCCG GTCGCGAGAC GGGGGGAGAG CACTGGTTGG    21600

CTTTTGGTTG GAACCCGCGC TCCAACACAT GCTACCTTTT TGATCCATTT GGATTCTCGG    21660

ATGACCGTCT TAAGCAGATC TACCAGTTTG AATACGAGGG GTTGCTGCGC CGTAGCGCCC    21720

TTGCTACTAA GGATCGCTGC ATTACCCTGG AAAAGTCCAC CCAAACAGTG CAGGGTCCGC    21780

GCTCCGCCGC TTGTGGACTT TTTTGCTGCA TGTTTCTCCA TGCCTTTGTA CACTGGCCAG    21840

ACCGTCCCAT GGACGGTAAC CCCACCATGA AGTTGCTTAC GGGAGTGCCC AACAACATGC    21900

TCCAGTCACC CCAAGTCCAG CCCACCCTGC GCAGGAACCA GGAGGCGCTC TACCATTTCC    21960

TCAACACACA TTCATCTTAC TTTCGTTCTC ACCGCGCACG TATCGAAAGG GCTACTGCGT    22020

TCGATCGTAT GGGATAATAT AAGTCATGTA AAACCGTGTT CAATAAACAG AACTTTATTT    22080

TTTACATACA CTGGTGGTTT GCTCATTTAT TCGCTCAGAA GTCGAAGGGG TTTTGGCGGG    22140

AATCAGAGTG ACCCGCGGGC AGGGATACGT TTCGGAACTG GAACTGAGCT TGCCACTTGA    22200

ATTCGGGGAT CACCAGCTTG GGAACTGGCA GGTCAGGCAG GATGTCGCTC CACAGCTTCC    22260

GGGTTAGTTG CAGGGCTCCC AACAGGTCAG GGGCTGAAAT CTTAAAATCG CAATTGGGAC    22320

CCGTGCTCTG AGCGCGGGAG TTGCGATACA CAGGGTTGCA ACACTGGAAC ACCATAAGCG    22380

ACGGGTATTT CACACTCGCC AGCACAGTGG GGTCGGTGAT AATTCCCACA TCCAGGTCTT    22440

CGGCATTGGC CATGCTAAAG GGGTCATCT TGCAAGTCTG TCTGCCCATA GTCGGTACCC    22500

AGCCTGGCTT GTGGTTGCAA TCGCAGCGCA GAGGGATTAG CATCATCTTG GCCTGGTCGG    22560

ATCTCATACC TGGATACACA GCTTTCATGA AAGCTTCATA TTGTTTGAAA GCCTGTTGGG    22620

CCTTGCTACC CTCAGTGTAG AACATCCCAC ATGACTTGCT AGAGAACTGG TTGGCAGCAC    22680

ACCCGGCATC ATTCACACAA CAGCGAGCGT CGTTGTTGGC TATTTGTACC ACACTCCTGC    22740

CCCAGCGGTT CTGGGTGATC TTGGTTCGCT CAGGGTTCTC CTTCAGCGCC CGTTGACCGT    22800

TTTCGCTTGC CACATCCATT TCTATGATAT GCTCCTTCTG GATCATGATG TTGCCATGCA    22860

AACACTTTAG CTTGCCTTCA TAATCATTAC ATCCATGTGA CCACAACGCG CATCCCGTAC    22920

ACTCCCAGTT ATTGTGAGCG ATCTCAGAAT AGGAGTGCAC CAACCCCTGC AGGAATCTTC    22980
```

```
CCATCATGGT TGAGAGGGTC TTGTTACTGG TGAAAGTCAA CGGGACGCCT CGATGCTCCT    23040

CATTCACATA CTGGTGGCAA ATTCGCTTGT ACTGTTCATG CTGCTCTGGC ATAAGCTTGA    23100

AAGAGGTTCT TAGGTCATTC TCCAGCCTGT ACTTCTCCAT CAGCACAGCC ATTACTTCCA    23160

TGCCCTTTTC CCAGGCAGAA ACCAGGGGTA GGCTCATGGC ATTTCTAACA GAAATAGCAG    23220

CTACTTTAGC CAGAGGGTCA TCCTTGTCGA TCTTCTCAAC ACTTCTTTTG CCATCCTTCT    23280

CAGTGATGCG CACGGGTGGG TAGCTGAAGC CCACAGCCAC CAGCTCCGCC TCTTCTCTTT    23340

CTTCTTCGCT GTCCTGACTG ATGTCTTGTA AAGGGACATG CTTGGTCTTC CTGGACTTCT    23400

TTTTGGGGGG TATTGGCGGA GGGCTGCTGC TCCGCTCCGG AGACATGGAG GACCGCGAAG    23460

TTTCGCTCAC CAGTACCACC TGGCTCTCGG TAGAAGAACC GGACCCCACA CGGCGGTAGG    23520

TGTTCCTCTT CGGGGGCAGA GGCGGAGGTG ACTGCGATGG GCTGCGGTCT GGCCTGGGAG    23580

GCGGATGACT GGCAGAGCCC CTTCCGCGTT CGGGGGTGTG CTCCCGGTGG CGGTCGCTTG    23640

ACTGATTTCC TCCGCGGCTG GCCATTGTGT TCTCCTAGGC AGAGAAAACA ACAGACATGG    23700

AGACTCAGCC ATCGCTGCCA ACACCGCTGC AAGCACCATC ACACCTCGCC TCCAGCGACG    23760

AGGAGGAGGA ACAAAGCTTA ACCGCCCCAC CACCCAGTCC CGCCACCACC ACCTCTACCC    23820

TCGAGGATGA GGAGGTCGAC GCACCCCAGG AGATACAGGC GCAGGATATG AAGGATGAGA    23880

AAGCGGAAGA GATTGAGGCA GATATCGAGC AGGACCCAGG CTATGTGACA CCGGCCGAGC    23940

ACGAGGAAGA GCTGAGACGC TTTCTAGAGA AAGATGATGA CAACCGTCCA GAACAGCAAG    24000

CAGATGGCGA TCAACAGAAG GCTGGGCTCG GTGGTCATGT TGCCGACTAC CTCACCGGCC    24060

TTGGTGGGGA GGATGTGCTC CTCAAACACC TAGCAAGGCA GTCGATCATA ATCAAAGACG    24120

CACTGCTTGA TCGCAGCGAA GTGCCCATCA GTGTGGAAGA GCTCAGCCGC GCCTACGAGC    24180

TCAATCTGTT CTCGCCTCGG GTACCCCCCA AGCGTCAGCC AAACGGCACC TGCGAGCCCA    24240

ACCCTCGCCT CAACTTCTAT CCCGCATTCA CCGTCCCCGA AGTGCTGGCC ACCTACCACA    24300

TATTTTTAA AAACCAAAAA ATCCCAATTT CCTGCCGCGC CAACCGAACT CGCGCCGATG    24360

CCCTGTTCAA CTTGGGACCT GGCGCTTGCT TACCTGATAT AACTTCCTTG GAAGAGGTCC    24420

CAAAGATCTT CGAAGGTCTG GGCAGTGATG AGACTCGGGC CGCAAATGCT CTGCAACAGG    24480

GAGAGAGTGG CATTGATGAA CATCACAGCG CTCTGGTGGA GTTGGAGGGC GATAATGCCC    24540

GACTTGCAGT ACTCAAGCGC AGTATCGAAG TGACCCATTT TGCATACCCC GCTGTCAACC    24600

TGCCTCCCAA AGTCATGAGC GCTGTCATGG ATCAGATACT CATTAAACGC GCAAGTCCCC    24660

TATCAGAAAA CATGCAGGAT CCAGACGCCT CGGATGAGGG CAAACCAGTG GTCAGTGATG    24720

AACAGCTATC TCGCTGGCTG GGCACCAACT CCCCACTAGA CTTGGAAGAG CGGCGCAAGC    24780

TCATGATGGC CGTGGTGCTA GTTACTGTGG AAATGGAGTG TCTTCGCCGC TTCTTCACTG    24840

ACCCCGAGAC ATTGCGCAAG CTCGAGGAGA ACCTGCACTA CACTTTTAGA CATGGATTTG    24900

TGCGACAGGC ATGCAAGATC TCCAACGTGG AGCTTACGAA CCTGGTTTCC TACATGGGCA    24960

TTTTGCATGA AAACAGACTC GGACAGAGCG TGTTGCACAC CACCCTGAAG GGTGAAGCCC    25020

GTCGCGACTA CATCCGCGAC ACTGTCTACC TCTACCTCTG CCATACCTGG CAGACTGGTA    25080

TGGGTGTGTG GCAGCAGTGT TTGGAAGAAC AGAACCTGAA AGAGCTTGAC AAGCTCTTAC    25140

AAAGATCCCT CAAATCCTTG TGGACGGGTT TTGACGAGCG CACAGTCGCC TCTGATCTGG    25200

CAGATCTCAT CTTCCCCGAG CGTCTCAGGA CCACTCTGCG CAACGGGCTG CCTGACTTCA    25260

TGAGCCAGAG CATGCTTAAC AACTTTCGCT CTTTCATCCT GGAACGCTCC GGTATCCTGC    25320
```

```
CCGCCACCTG CTGTGCGCTA CCATCCGACT TTGTGCCTCT GACCTACCGC GAGTGCCCAC     25380

CACCGCTATG GAGCCACTGC TACCTGTTCC GCCTGGCCAA CTACCTATCA TACCACTCGG     25440

ATGTGATCGA GGATGTGAGC GGAGATGGCC TGCTTGAGTG CCACTGCCGC TGTAATCTCT     25500

GCTCACCACA TCGCTCCCTC GTCTGTAACC CCCAGCTGCT TAGTGAAACC CAAATTATCG     25560

GCACCTTCGA ATTGCAGGGT CCCAGCGGCG AAGGCGATGG GTCTTCTCCT GGGCAAAGTT     25620

TGAAACTGAC CCCGGGACTG TGGACCTCCG CCTACCTGCG CAAGTTCTCC CCCGAGGACT     25680

ACCACCCCTA TGAGATCAGG TTCTATGAGG ACCAATCACA GCCGCCCAAA GCCGAGCTAT     25740

CAGCATGCGT CATCACCCAG GGGGCAATTT TGGCCCAATT GCAAGCCATC CAAAAATCCC     25800

GCCAAGAATT TTTGCTGAAA AAGGGTAACG GAGTCTACCT CGACCCCCAG ACTGGTGAGG     25860

AGCTCAACAC AAGGTTTTCT CAGGATGTCT CAGCGCCGAG GAAGCAAGAA GTTGAAAGTG     25920

CAGCTGCCGC CCCCAGAGGA TATGGAGGAA GACTGGGACA GTCAGACAGA GGAGATGGAA     25980

GATTGGGACA GCCAGGCAGA GGAGGAGGAG GACAGCCTGG AGGAAGACAG TTTGGAGGAG     26040

GAAGACGAGG AGGCAGAGGA GGTGGAAGAA GCAACCGCCG CCAAACAGTT GTCCTCGGCA     26100

GCGGAGACAA GCAAGGCCAC AGACAGTACC ACAGCTACCA TCTCCGCTCC GGGTCGGGGG     26160

GCCCAGCACC GTCCCAACAG TAGATGGGAT GAGACCGGGC GACTCCCGAA TGCGACCACC     26220

GCTTCTAAGA CTGGTAAGGA GCGGCAGGGA TACAAGTCCT GGCGGGGGCA TAAGAACGCT     26280

ATCATATCCT GCTTGCATGA ATGCGGGGGC AACATATCCT TCACCCGCCG CTACCTGCTC     26340

TTCCACCACG GGGTGAACTT CCCCCGCAAT GTCTTGCATT ACTACCGTCA CCTCCACAGC     26400

CCCTATTACA GCCCGCAAGT CTCGGCAGAA AAAGACAACA GCAGCAAGGA CCTCCAGCAG     26460

AAAACCAGCA GCAGTTAGAA AACCCACAGC AGGTGCAGGA GGACTGAGAA TCACAGCGAA     26520

CGAGCCAGCG CAGACCCGAG AGCTGAGAAA CCGGATTTTT CCAACCCTCT ATGCCATCTT     26580

CCAACAGAGT CGGGGGCAAG AGCAGGAACT GAAAGTAAAA AACCGATCTT TGCGCTCGCT     26640

CACCCGAAGT TGTTTGTATC ACAAGAGCGA AGACCAACTT CAGCGCACTC TCGAGGACGC     26700

CGAGGCTCTC TTCAACAAGT ACTGCGCGCT CACTCTTAAA GAGTAGCCCG CGCCCGCGCT     26760

ATCTCGAAAA AGGCGGGAAT TACGTCACCC TTGGCGCCCG TCCTTTGCCC TCGTCATGAG     26820

TAAAGAAATT CCCACGCCTT ACATGTGGAG TTATCAGCCC CAAATGGGAC TGGCAGCAGG     26880

CGCCTCCCAG GACTACTCCA CCCGTATGAA TTGGCTCAGC GCCGGTCCCT CGATGATCTC     26940

ACGGGTTAAT GATATACGAG CTTATCGAAA CCAATTACTC CTAGAACAGT CAGCACTTAC     27000

CACCACCCCC AGACAACACC TTAATCCCCG AAATTGGCCC GCCGCCCTGG TGTACCAGGA     27060

AACCCCCGCT CCCACCACCG TACTACTTCC TCGAGACGCC CAGGCCGAAG TTCAGATGAC     27120

TAACGCAGGT GTACAGCTGG CGGGCGGTTC CGCCCTTTGT CGTCACCGGC CTCAACAGAG     27180

TATAAAACGC CTGGTGATCA GAGGCCGAGG TATCCAGCTC AACGACGAGT CGGTGAGCTC     27240

TTCGCTTGGT CTGCGACCAG ACGGAGTCTT CCAAATTGCC GGCTGCGGGA GATCTTCCTT     27300

CACTCCTCGT CAGGCTGTAC TGACTTTGGA GAGTTCGTCC TCACAGCCCC GCTCGGGTGG     27360

CATCGGGACT CTCCAGTTTG TGGAGGAGTT TACTCCCTCT GTCTACTTCA ACCCCTTCTC     27420

CGGATCTCCT GGGCATTACC CGGACGAGTT CATACCAAAT TTCGACGCAA TCAGCGAGTC     27480

AGTGGATGGT TATGATTGAT GTCTAATGGT GGCGCGGCTG AGCTAGCTCG ACTGCGACAT     27540

CTAGACCACT GCCGCCGCTT TCGCTGCTTT GCCAGAGAAC TCACCGAGTT CATCTACTTC     27600

GAAATACCCG AGGAGCACCC TCAGGGACCG GCCCACGGAG TGCGTATTAC CATCGAAGGG     27660

GGTATAGACT CTCGCCTGCA TCGAATCTTC TGCCAGCGGC CCGTGCTAAT CGAGCGCGAC     27720
```

```
CAGGGAAACA CCACAGTCTC CATCTACTGC ATCTGTAACC ACCCCGGATT GCATGAAAGC    27780

CTTTGCTGTC TTATTTGTGC TGAGTTTAAT AAAAACTGAG TTAAGACTCT CCTACGGACT    27840

ACCAATTCTT CAACCCGGAC TTTATAACAA TCAGACCCTC CTACCAAGTC AGAAGACCCC    27900

AACCCTTCCT CTGATCCAGG ACTCTAATTC TACCTCCCCA GCACCATACT TTACTAGCCT    27960

TCCCGAAACT AACAACCTCG GAGCTAAACT GCACCGCTTT TCCAGAAGCC TTCTCTCTGC    28020

CAATACTACC ACTCCCAGAA CCGGAGGTGA GCTCCGTAGT CTTCCTAATA CAACCCCTG    28080

GGTGGTAACT GGGTTTGTAA CATTAGGTGT AGTTGCGGGT GGGCTTGTGC TTATCCTTTG    28140

CTACCTATAC ACACCTTGCT GTGCTTATTT AGTAATCTTG TGTTGCTGGT TTAAGAAATG    28200

GGGGCCCTAC TAGCCGCGCT TGCTTTACTT TCACTTTTTG AGCCTGGCTC TACTATGCTA    28260

GTTCAGCCTG TACTATTTGA TCCATGCCTC AATTTTGATC CAGACAACTG CACACTCACT    28320

TTTGCTCCAG AGGCTGGACG CTGTGGAGTT CTTATTAGGT GCGGACGGGA ATGCAGTCCC    28380

ATTGAAATAC ACCACAATAA CAAACTTTGG AACAATACCT TATTCACCAC ATGGCAGCCA    28440

GGAGACCCTG AGTGGTATAC TGTCTCTGTC CGTGGTCCTG ACGGTTCCAT CCGCACTGCT    28500

AATAACACTT TTATTTTTGC TGAGATGTGC GATCTGACCA TGTTCATGAG CAAACAGTAT    28560

AACCTATGGC CTCCAAGCAA GGAGAACATT GTGGCATTCT CCCTTGCTTA TTGCTTGTGT    28620

ACGTGTCTCA TTACTGCTAT TCTGTGTATC TGCATACACT TGCTTATTGC CACTCGCCAC    28680

AGAAACAGCA ATAAGGAAAA AGAGAAAATG CCTTGAGCTT TTTCTCATCT ATGTTTTTTT    28740

TTTTTGTTAC AGACATGGCT TCAGTTATAG CTCTAATTAT TGCCAGCATT CTCACTGCCG    28800

CACACGGACA AACAATTGTC TATATTACCT TAGGTCATAA CCACACTCTT ATAGGACCCC    28860

AAATTAGTTC ACAGGTTATA TGGACCAAAC TTGGAAGTGT TGATTATTTT GACATAATCT    28920

GCAACAGAAC TAAACCAATA TTTGTAACCT GTAACAAACA AAATCTCACC TTAATCAATG    28980

TTAGCGAAAT TTACAACGGT TACTATTATG GTTATGACAG ACACAGCAGT GAATATAAAA    29040

ATTACTTAGT TCGCATAACT CAACCCAAAA CTACAAAAAT GCCAAATATG GCAAAAATTC    29100

AAATGGTTAG CACATTAGAA AATCTTTCAT ATCCCACCAC ACCCGATGAG AAAAACATTC    29160

CAAATTCAAT GATTGCCATT ATTGCGGCGG TGGCAGTGGG AATGGCACTA ATAATAATTT    29220

GTATGTTCCT ATATGCTTGT TACTGTAGAA AGTTTCACAA ACAGGACCCC CTACTAAATT    29280

TTTGACATTT AATTTTTTAT ACAGCTATGG TTTCCACTAC AGCCTTTTTT ATTATCAGTA    29340

GCCTTGCAGC TGTCACTTAT GGTCGCTCAC ACCTCACTGT AACTGTTGGC TCAACTTGTA    29400

CACTACAAGG ACCCCAAGAA GGGCATGTCA GTTGGTGGAG AATATATGAT AGTGGATGGT    29460

TCATTAGGCC ATGTGACCAG CCTGGTAACA AATTTCTCTG CAACGGGAGA GACCTGACCA    29520

TTATTAACAT AACAGTAAAT GACCAGGGCT TCTATTATGG AACTAACTAT AAAAATAACT    29580

TAGATTACAA CATTATCGTA GTGCCAGCCA CCACTCCAGC TCCCCGCAAA ACCACTTTCT    29640

TTAGCAGCAG TGCCAGTATT TCTAAAACAG CTTCTGCAAT CTTAAAGCTT CAAAAAATCG    29700

CTTTAAGTAA TTCCACAACC TCTTCCACTA ACACAACGTC TAAATCAGTA GTCGGCATCG    29760

CTGTTGCCGC GGTAATGGGA TTAATGATTA TAACTTTGTG CATAATCTAC TACGCCTGCT    29820

GCTATAGAAA ACATGAACAA AAAAGCGATC CCTTGCTGAA TTTTGATATT TAATTTTTTT    29880

TTATAGAATC ATGAAAAAAC TAATTATCCT AGCTTTTATT TTGTTTCAAT CATATACCAC    29940

TAACACTACC AATGTGCAGA CTACTTTAAA TCATAGTATG GAAAACCACA CTACCTCTTA    30000

TAAGCACACA AACATCACTA CCCATCAGCC TAAATATGCT ATGCAACTAG AAATCACAAT    30060
```

```
ACTAATTGTG ATTGCAATAC TTATCATATC TATCATTTTC TATTTTACCC TATGCCGCCA    30120

AATACCCAAT ATTCATAGAA AAAGACGTCC CATTTATTGC CCCATGATTA GTCAACCCCA    30180

TATGACTCTA AATGAAATCT AAGATCTATT CTTTCTCTTT TTTACAGTAT GGTGAACACC    30240

AATCATGATT CCTAGAAATT TCTTCTTCAC CATACTCATC TGTGCTTTTA ATGTCTGTGC    30300

CACCTTTACA GCAGTAGCCA CTACAAGCCC CGACTGTATA GGACCATTTG CCTCATACAC    30360

ACTTTTTGCT TTTGTCGCTT GCACCTGCGT GTGTAGCGTA GTCTGCCTGG TTATTAATTT    30420

TTTTCAACTT GTAGACTGGA TCTTTGTGAG ACTTGCCTAT CTGCGTCACC ATCCCGAATA    30480

CCGCAATCAA CATGTTGCGG CACTTCTCAG ACTTATTTAA AACCATGCAG GCTATACTAC    30540

CAGTCATTCT GCTTCTGTTG CTCCCCTGCG ATGCCTTAAC CCCCGTCGCT AATCGTACCC    30600

CACCTGAACA ACTTAGAAAA TGCAAATTCC AACAACCATG GACATTCCTT GATTGCTATC    30660

GAGAAAAATC TGATTTCCCC ACATACTGGA TTATGATCAT TGGAATTGTT AATCTAGTTT    30720

CTTGCACACT ATTCTCTTTC CTTGTTTATC ATTTTTTTGA TTTTGGATGG AATGCCCCCA    30780

ATGCACTCAC TTACCCACAA GAACCAGAGG AACATATCCC ACTACAGAAC ATGCAACAGC    30840

CAATAGCTTT AATAGATTAT GACAATGAGC CACAGCCCTC GCTGCTTCCT GCTATTAGTT    30900

ACTTCAACCT AACCGGTGGA GATGACTGAC CCACTCGCCG CCTCCACTGC TGCCGAGGAA    30960

CTGCTTGATA TGGACGGCCG CACCTCAGAA CAGCGACTCG CCCAACTACG CATACGCCAG    31020

CAGCAGGAAC GTGCCGCCAA GGAGCTCAGG GATGCTATTG AAATTCACCA GTGCAAAAAA    31080

GGCATATTCT GTCTGGTGAA ACAAGCCAAG ATTTCCTACG AGATCACCAC TACTGACCAT    31140

CGCCTCTCAT ACGAGCTCGG TCCGCAGCGG CAAAAATTCA CGTGTATGGT GGGAATCAAC    31200

CCCATAGTCA TTACCCAGCA GGCTGGAGAT ACTAAGGGTT GCATCCACTG TTCCTGCGGT    31260

TCCACCGAGT GCATCTACAC CCTACTTAAG ACCCTCTGCG GCCTTCGAGA CATCCTACCC    31320

ATGAACTGAT CAACTTTCCT TCCCCCCATT CAAAAAACAA TAATAAAAAT CACTTACTTG    31380

AAATCAGCAA TCATGTCTCC GTCCAAATTT TCTCCTAGCA GCACCTCACT TCCCTCTTCC    31440

CAACTCTGGT ACTCTAAACC CCGCCTGGCA GCATACTTTC TCCACACTTT AAATGGAATG    31500

TCAAATTTTA GTTCCTCTTT TCTACCCACA ATCTTCATCT CTTTATTCTC CCCAGATGGC    31560

CAAACGAACT CGGTTGAGCA GCTCCTTCAA CCCGGTCTAC CCCTATGAAG ATGAAAACAG    31620

CTCACACCCC TTTATAAACC CTGGTTTCAT TTCCCCTAAT GGGTTACAC AAAGCCCAGA    31680

CGGAGTTCTG ACACTAAATT GTGTTGCTCC CCTTACAACC GCTAATGGCG CCCTAGATAT    31740

CAAAGTAGGA GGAGGGCTTA AAGTGAACTC AACTGATGGA TTCTTAGAAG AAAACATAAA    31800

CATCACATCA CCACTTACAA AGTCTAACCA TTCTATAGGT TTAGAATGGA GCGATGGGTT    31860

ACAAACAAAC GAAGCCAAGC TCTGTGTCAA ACTTGGAAAA GGTCTTGTAT TTGACTCTTC    31920

CAGTGCTATT GCAATGAAAA ATAACACTTT GTGGACAGGT GCAAAACCAA GTGCCAACTG    31980

TGTAATTAAA GAGGGAGAAG ATTCCCCAGA CTGTAAGCTC ACTTTAGTTC TAGTGAAGAA    32040

TGGAGGACTG GTAAATGGAT ACATAACATT AATGGGAGAC TCAGAATATA CTAACACCTT    32100

GTTTAAAAAC AAACAAGTTA CAATAGATGT AAACCTCGCA TTTGATAATA CCGGCCAAAT    32160

TATCACTTAC CTATCATCTC TTAAAAGTAA CCTGAACTTT AAAGACAACC AAAACATGGC    32220

TACTGGAACC ATAACCAGTG CCAAAGGCTT CATGCCCAGC ACCACCGCCT ATCCATTTAT    32280

AACATACGCC ACTCAGTCCC TAAATGAAGA TTACATTTAT GGAGAGTGTT ACTACAAATC    32340

TACCAATGGA ACTCTCTTTC CACTAAAAGT TACTGTCACA CTAAACAGAC GTATGTCAGC    32400

TTCTGGAATG GCCTATGCTA TGAACTTTTC ATGGTCTCTA AATGCAGAGG AAGCCCCTGA    32460
```

```
AACTACCGAA GTCACTCTCA TTACCTCCCC CTTCTTTTTT TCTTATATCA GAGAAGACGA    32520

CTGACAACAA AAAATAAAGA TTAACTTTTT TATTGAAATC AGTTTACAAG ATTCGAGTAG    32580

TTATTTTGCC CCCCTCTTCC CATTTTATAG AATACACAAT CCTCTCCCCA CGCACAGCTT    32640

TGAACATTTG AATTCCATTA GAGATAGACA TAGTTTTAGA TTCCACATTC CACACAGTTT    32700

CAGAGCGGGC CAATCTTGGA TCAGTGATAG ATATAAAGCC ATCGAACAG  TCTTTCAAGG    32760

TGGTTTCACA GTCCAACTGC TGCGGCTGCG GCTCCGGAGT TTGGATTAGA GTCATCTGGA    32820

AGAAGAACGA TGGGAGTCAT AATCCGAGAA CGGGATCGGA CGGTTGTGTC TCAAACCTCG    32880

AAGCAGTCGC TGTCTGCGCC GCTCCGTGCG ACTGCTGCTG ATGGGATCAG GATCCACAGT    32940

CTCTCTAAGC ATGATTTTAA TAGCCCTCAA CATTAACATC CTGGTGCGAT GTGCACAACA    33000

ACGCATTCTA ATCTCGCTTA GCTCACTGCA GTAGGTACAA CACATTACCA CAATGTTGTT    33060

TAACAGGCCA TAATTAAAGG TGCTCCAGCC AAAACTCATC TCAGGGATAA TCATGCCCGC    33120

GTGACCATCA TACCAGATCT TAATGTAAAT CAAATGGCGC CCCCTCCAGA ACACACTGCC    33180

CACATACATA ATCTCCTTGG GCATATGCAT GTTCACAATC TCTCTGTACC ATGGACAGCG    33240

CTGGTTAATC ATACAGCCCC TAATAACCTT CCGGAACCAA ATAGCCAGCA CTGCTCCCCC    33300

AGCAATACAT TGAAGAGAAC CCGGCTGTTT ACAGTGACAA TGAAGAACCC ACTTCTCTCG    33360

CCCATGGATC ACTTGAGAAT GAAATATATC TATAGTGGCA CAACACAAAC ATAAATGCAT    33420

GCATCTTTTC ATAACCCTTA ACTCTTCGGG GGTTAGAAAC ATATCCCAGG GAATGGGAAG    33480

CTCTTGCAAA ACAGTAAAGC TGGCAGAACA AGGAAGACCG CGAACATAAC TTACACTGTG    33540

CATGGTCAGG GTATTACAAT CTGGTAACAG TGGATGGTCT TCAGTCATAG AAGCTCTGGT    33600

TTCATTTTCC TCACAGCGTG GTAAAGGGGC CCTCAAATGA GGGTCCATGA TGTACGGATG    33660

ATGTCTGTGG CATGACGTCG ATCGTGCACG CGACCTCGTT GTAATGGAGC TGCTTCCTGA    33720

CATTCTCGTA TTTTGCATGA CAAAACCTAG CCTTAGCACA ACACACTTCT CTTCGCCTTC    33780

TATCCCGTCG CCTAACGCAT TCAGTGTGGT AATTGAAGTA CAGCCATTCC CGTAGATTGG    33840

TCAAAAGTTC CTCGGCTTCA GTTGTTATGA AAACTCCATC ATGTCTGATC GCTCTGATAA    33900

AATCATTCAC TGTAGAATGG GCAATACCCA ACCATGCAAT ACAATTAGCT TGAGTTTTAA    33960

TCAAAGGAGG GGGAGGAAGA CATGGAAGAA CCATAATTAA TTTTTTATTC CAGACGATCT    34020

CGCAGTATTT CTAAATGAAG ATCACGAAGA TGGCACCTCT CGCCCCCACT GTGTTGATGA    34080

AAAATAACAG CTAAGTCAAA CACGATGCGA TTCTCAAGAT GCTCAATGGT GGCTTCAAGC    34140

AAAGCCTCCA CGCGCACATC CAAAAACAAA AGAACAGCAA AAGAAGGGGC ATGTTCTAAT    34200

TCCTCAATCA TCATATTACA TTCCTGTACC ATTCCCAGAT AATTTTCATC TTTCCAGCCT    34260

TGAATTAATC GTGTCATTTC TTCTTGTAAA TCCAATCCAC ACATGAAAAA CAGCTCTCGG    34320

AGGGCACCCT CCACCACCAT CCTTAAGCAC ACCCTCATAA TGACAAAATA TCTTGCTCCT    34380

GTGTCACCTG CAGCAAATTG AGAATGGCAA CATCAAACGA CATGCCATTG TCTCTAAGCT    34440

CTTCTCTAAG TTCAAGTTGT AAAAACTCCT TCAAATCATC GCCAAACTGC TTGGCCATAG    34500

GTCCGCCAGG AATAAGAGCG GGGACGCTA  CTGTACAGAA CAAACGGAGA CCGCCCAAT    34560

GGGATCCAGC AAAAGTGAGG TTACAATAAG CATACTGAGA ACCTCCAGTG ATATCATCCA    34620

GAGTGCTGGA AACATAATCA GGCAGAGTTT CTCGTATAAA ATTAATAAAA GAAAATTCTG    34680

CCAGATGAAC ATTTAAAATT TCTGGAATAC AGATGCAATA AGTTACCGCG CTGCGCTCCA    34740

ACATTGTTAG TACGATTAGT CTGTAAAAAA ACAGCACAAA AGTTATTACA TCATGCTAGC    34800
```

-continued

```
CTGGCGAACG GATGGATAAA TCACTCTCTC CAACACCAGG CAGGCTACAG GGTCTCCAAC    34860

ACGACCCTCG TAAAACCTGT CAGTATGATT AAAAAGCATC ACCGAAAGAG GCTGTTGATG    34920

AGCAGCAAAT ATTATTTGCG ATGAAGCATA CAATCCAGAA GTGTTAGTAT CAGTTAAAGA    34980

AAAAAAACGT CCAATATAGC ATCTGGGAAC AATTATGCTC AATCTCAAAT GCAGCAAAGC    35040

GACACCTCTG GGATGCAAAG TAAAATCCAC AGGAGCATAA AAAATGTAAT TATTCCCCTC    35100

TTGCACAGGC AGCCTAGCTC CCGGCCCCTC CAAAATCACA TACAAAACTT CAGCCATAGC    35160

TTACCGCACA ATCAGGCAG AGCAGACAGG AGAACTATAA ACTGACTGCC GCCTGTGCGC    35220

AATATATAGT CAACCTATAC ACTGACGTAA TCGGATAAAG TCTAAAAAAT CCCGCCAAAA    35280

CCAGCACACG CCCAGAAACT GTGTCATCCG CGAGAAAATT TCACTTCCGC ATTTTATTCC    35340

GGAAAAACGT CACTTCCTCT TTCCCACGAA TCGTCACTTC CGGTAATCTT GTAACGTCAC    35400

CTTCCCGCCC CGCCCCTAAC GGTCGCCGTC CCCACAGCCA ATCACCTTTC ACCCTCCCCA    35460

AATTCAAACG CCTCATTTGC ATATTAACAC GCACCAAAAG TTTAAGGTAT ATTATTGATG    35520

ATGG                                                                35524
```

(2) INFORMATION FOR SEQ ID NO:2:

(i) SEQUENCE CHARACTERISTICS:
        (A) LENGTH: 36519 base pairs
        (B) TYPE: nucleic acid
        (C) STRANDEDNESS: double
        (D) TOPOLOGY: unknown (ii) MOLECULE TYPE: cDNA (xi) SEQUENCE DESCRIPTION: SEQ ID NO:2:

```
CCATCTTCAA TAATATACCT CAAACTTTTT GTGCGCGTTA ATATGCAAAT GAGGCGTTTG      60

AATTTGGGGA GGAAGGGCGG TGATTGGTCG AGGGATGAGC GACCGTTAGG GGCGGGGCGA     120

GTGACGTTTT GATGACGTGG TTGCGAGGAG GAGCCAGTTT GCAAGTTCTC GTGGGAAAAG     180

TGACGTCAAA CGAGGTGTGG TTTGAACACG GAAATACTCA ATTTTCCCGC GCTCTCTGAC     240

AGGAAATGAG GTGTTTCTGG GCGGATGCAA GTGAAAACGG GCCATTTTCG CGCGAAAACT     300

GAATGAGGAA GTGAAAATCT GAGTAATTTC GCGTTTATGG CAGGGAGGAG TATTTGCCGA     360

GGGCCGAGTA GACTTTGACC GATTACGTGG GGGTTTCGAT TACCGTGTTT TTCACCTAAA     420

TTTCCGCGTA CGGTGTCAAA GTCCGGTGTT TTTACGTAGG TGTCAGCTGA TCGCCAGGGT     480

ATTTAAACCT GCGCTCTCCA GTCAAGAGGC CACTCTTGAG TGCCAGCGAG AAGAGTTTTC     540

TCCTCCGCGC CGCGAGTCAG ATCTACACTT TGAAAGATGA GGCACCTGAG AGACCTGCCC     600

GATGAGAAAA TCATCATCGC TTCCGGGAAC GAGATTCTGG AACTGGTGGT AAATGCCATG     660

ATGGGCGACG ACCCTCCGGA GCCCCCCACC CCATTTGAGA CACCTTCGCT GCACGATTTG     720

TATGATCTGG AGGTGGATGT GCCCGAGGAC GATCCCAATG AGGAGGCGGT AAATGATTTT     780

TTTAGCGATG CCGCGCTGCT AGCTGCCGAG GAGGCTTCGA GCTCTAGCTC AGACAGCGAC     840

TCTTCACTGC ATACCCCTAG ACCCGGCAGA GGTGAGAAAA AGATCCCCGA GCTTAAAGGG     900

GAAGAGATGG ACTTGCGCTG CTATGAGGAA TGCTTGCCCC CGAGCGATGA TGAGGACGAG     960

CAGGCGATCC AGAACGCAGC GAGCCAGGGA GTGCAAGCCG CCAGCGAGAG CTTTGCGCTG    1020

GACTGCCCGC CTCTGCCCGG ACACGGCTGT AAGTCTTGTG AATTTCATCG CATGAATACT    1080

GGAGATAAAG CTGTGTTGTG TGCACTTTGC TATATGAGAG CTTACAACCA TTGTGTTTAC    1140

AGTAAGTGTG ATTAAGTTGA ACTTTAGAGG GAGGCAGAGA GCAGGGTGAC TGGGCGATGA    1200
```

```
CTGGTTTATT TATGTATATA TGTTCTTTAT ATAGGTCCCG TCTCTGACGC AGATGATGAG    1260

ACCCCCACTA CAAAGTCCAC TTCGTCACCC CCAGAAATTG GCACATCTCC ACCTGAGAAT    1320

ATTGTTAGAC CAGTTCCTGT TAGAGCCACT GGGAGGAGAG CAGCTGTGGA ATGTTTGGAT    1380

GACTTGCTAC AGGGTGGGGT TGAACCTTTG GACTTGTGTA CCCGGAAACG CCCCAGGCAC    1440

TAAGTGCCAC ACATGTGTGT TTACTTGAGG TGATGTCAGT ATTTATAGGG TGTGGAGTGC    1500

AATAAAAAAT GTGTTGACTT TAAGTGCGTG GTTTATGACT CAGGGGTGGG GACTGTGAGT    1560

ATATAAGCAG GTGCAGACCT GTGTGGTTAG CTCAGAGCGG CATGGAGATT TGGACGGTCT    1620

TGGAAGACTT TCACAAGACT AGACAGCTGC TAGAGAACGC CTCGAACGGA GTCTCTTACC    1680

TGTGGAGATT CTGCTTCGGT GGCGACCTAG CTAGGCTAGT CTACAGGGCC AAACAGGATT    1740

ATAGTGAACA ATTTGAGGTT ATTTTGAGAG AGTGTTCTGG TCTTTTTGAC GCTCTTAACT    1800

TGGGCCATCA GTCTCACTTT AACCAGAGGA TTTCGAGAGC CCTTGATTTT ACTACTCCTG    1860

GCAGAACCAC TGCAGCAGTA GCCTTTTTTG CTTTTATTCT TGACAAATGG AGTCAAGAAA    1920

CCCATTTCAG CAGGGATTAC CAGCTGGATT TCTTAGCAGT AGCTTTGTGG AGAACATGGA    1980

AGTGCCAGCG CCTGAATGCA ATCTCCGGCT ACTTGCCGGT ACAGCCGCTA GACACTCTGA    2040

GGATCCTGAA TCTCCAGGAG AGTCCCAGGG CACGCCAACG TCGCCAGCAG CAGCAGCAGG    2100

AGGAGGATCA AGAAGAGAAC CCGAGAGCCG GCCTGGACCC TCCGGCGGAG GAGGAGGAGT    2160

AGCTGACCTG TTTCCTGAAC TGCGCCGGGT GCTGACTAGG TCTTCGAGTG GTCGGGAGAG    2220

GGGGATTAAG CGGGAGAGGC ATGATGAGAC TAATCACAGA ACTGAACTGA CTGTGGGTCT    2280

GATGAGTCGC AAGCGCCCAG AAACAGTGTG GTGGCATGAG GTGCAGTCGA CTGGCACAGA    2340

TGAGGTGTCG GTGATGCATG AGAGGTTTTC TCTAGAACAA GTCAAGACTT GTTGGTTAGA    2400

GCCTGAGGAT GATTGGGAGG TAGCCATCAG GAATTATGCC AAGCTGGCTC TGAGGCCAGA    2460

CAAGAAGTAC AAGATTACTA AGCTGATAAA TATCAGAAAT GCCTGCTACA TCTCAGGGAA    2520

TGGGGCTGAA GTGGAGATCT GTCTCCAGGA AAGGGTGGCT TTCAGATGCT GCATGATGAA    2580

TATGTACCCG GGAGTGGTGG GCATGGATGG GGTTACCTTT ATGAACATGA GGTTCAGGGG    2640

AGATGGGTAT AATGGCACGG TCTTTATGGC CAATACCAAG CTGACAGTCC ATGGCTGCTC    2700

CTTCTTTGGG TTTAATAACA CCTGCATCGA GGCCTGGGGT CAGGTCGGTG TGAGGGGCTG    2760

CAGTTTTTCA GCCAACTGGA TGGGGGTCGT GGGCAGGACC AAGAGTATGC TGTCCGTGAA    2820

GAAATGCTTG TTTGAGAGGT GCCACCTGGG GGTGATGAGC GAGGGCGAAG CCAGAATCCG    2880

CCACTGCGCC TCTACCGAGA CGGGCTGCTT TGTGCTGTGC AAGGGCAATG CTAAGATCAA    2940

GCATAATATG ATCTGTGGAG CCTCGGACGA GCGCGGCTAC CAGATGCTGA CCTGCGCCGG    3000

CGGGAACAGC CATATGCTGG CCACCGTACA TGTGGCTTCC CATGCTCGCA AGCCCTGGCC    3060

CGAGTTCGAG CACAATGTCA TGACCAGGTG CAATATGCAT CTGGGGTCCC GCCGAGGCAT    3120

GTTCATGCCC TACCAGTGCA ACCTGAATTA TGTGAAGGTG CTGCTGGAGC CCGATGCCAT    3180

GTCCAGAGTG AGCCTGACGG GGGTGTTTGA CATGAATGTG GAGGTGTGGA AGATTCTGAG    3240

ATATGATGAA TCCAAGACCA GGTGCCGAGC CTGCGAGTGC GGAGGGAAGC ATGCCAGGTT    3300

CCAGCCCGTG TGTGTGGATG TGACGGAGGA CCTGCGACCC GATCATTTGG TGTTGCCCTG    3360

CACCGGGACG GAGTTCGGTT CCAGCGGGGA AGAATCTGAC TAGAGTGAGT AGTGTTCTGG    3420

GGCGGGGGAG GACCTGCATG AGGGCCAGAA TAACTGAAAT CTGTGCTTTT CTGTGTGTTG    3480

CAGCAGCATG AGCGGAAGCG GCTCCTTTGA GGGAGGGGTA TTCAGCCCTT ATCTGACGGG    3540

GCGTCTCCCC TCCTGGGCGG GAGTGCGTCA GAATGTGATG GGATCCACGG TGGACGGCCG    3600
```

-continued

```
GCCCGTGCAG CCCGCGAACT CTTCAACCCT GACCTATGCA ACCCTGAGCT CTTCGTCGTT    3660

GGACGCAGCT GCCGCCGCAG CTGCTGCATC TGCCGCCAGC GCCGTGCGCG GAATGGCCAT    3720

GGGCGCCGGC TACTACGGCA CTCTGGTGGC CAACTCGAGT TCCACCAATA ATCCCGCCAG    3780

CCTGAACGAG GAGAAGCTGT TGCTGCTGAT GGCCCAGCTC GAGGCCTTGA CCCAGCGCCT    3840

GGGCGAGCTG ACCCAGCAGG TGGCTCAGCT GCAGGAGCAG ACGCGGGCCG CGGTTGCCAC    3900

GGTGAAATCC AAATAAAAAA TGAATCAATA AATAAACGGA GACGGTTGTT GATTTTAACA    3960

CAGAGTCTGA ATCTTTATTT GATTTTTCGC GCGCGGTAGG CCCTGGACCA CCGGTCTCGA    4020

TCATTGAGCA CCCGGTGGAT CTTTTCCAGG ACCCGGTAGA GGTGGGCTTG GATGTTGAGG    4080

TACATGGGCA TGAGCCCGTC CCGGGGGTGG AGGTAGCTCC ATTGCAGGGC CTCGTGCTCG    4140

GGGGTGGTGT TGTAAATCAC CCAGTCATAG CAGGGGCGCA GGGCATGGTG TTGCACAATA    4200

TCTTTGAGGA GGAGACTGAT GGCCACGGGC AGCCCTTTGG TGTAGGTGTT TACAAATCTG    4260

TTGAGCTGGG AGGGATGCAT GCGGGGGGAG ATGAGGTGCA TCTTGGCCTG GATCTTGAGA    4320

TTGGCGATGT TACCGCCCAG ATCCCGCCTG GGGTTCATGT TGTGCAGGAC CACCAGCACG    4380

GTGTATCCGG TGCACTTGGG GAATTTATCA TGCAACTTGG AAGGGAAGGC GTGAAAGAAT    4440

TTGGCGACGC CTTTGTGCCC GCCCAGGTTT TCCATGCACT CATCCATGAT GATGGCGATG    4500

GGCCCGTGGG CGGCGGCCTG GGCAAAGACG TTTCGGGGGT CGGACACATC ATAGTTGTGG    4560

TCCTGGGTGA GGTCATCATA GGCCATTTTA ATGAATTTGG GGCGGAGGGT GCCGGACTGG    4620

GGGACAAAGG TACCCTCGAT CCCGGGGCG TAGTTCCCCT CACAGATCTG CATCTCCCAG    4680

GCTTTGAGCT CGGAGGGGGG GATCATGTCC ACCTGCGGGG CGATAAAGAA CACGGTTTCC    4740

GGGGCGGGGG AGATGAGCTG GGCCGAAAGC AAGTTCCGGA GCAGCTGGGA CTTGCCGCAG    4800

CCGGTGGGGC CGTAGATGAC CCCGATGACC GGCTGCAGGT GGTAGTTGAG GGAGAGACAG    4860

CTGCCGTCCT CCCGGAGGAG GGGGGCCACC TCGTTCATCA TCTCGCGCAC GTGCATGTTC    4920

TCGCGCACCA GTTCCGCCAG GAGGCGCTCT CCCCCCAGGG ATAGGAGCTC CTGGAGCGAG    4980

GCGAAGTTTT TCAGCGGCTT GAGTCCGTCG GCCATGGGCA TTTTGGAGAG GGTTTGTTGC    5040

AAGAGTTCCA GGCGGTCCCA GAGCTCGGTG ATGTGCTCTA CGGCATCTCG ATCCAGCAGA    5100

CCTCCTCGTT TCGCGGGTTG GACGGCTGC GGGAGTAGGG CACCAGACGA TGGGCGTCCA    5160

GCGCAGCCAG GGTCCGGTCC TTCCAGGGTC GCAGCGTCCG CGTCAGGGTG GTCTCCGTCA    5220

CGGTGAAGGG GTGCGCGCCG GGCTGGGCGC TTGCGAGGGT GCGCTTCAGG CTCATCCGGC    5280

TGGTCGAAAA CCGCTCCCGA TCGGCGCCCT GCGCGTCGGC CAGGTAGCAA TTGACCATGA    5340

GTTCGTAGTT GAGCGCCTCG GCCGCGTGGC CTTTGGCGCG GAGCTTACCT TTGGAAGTCT    5400

GCCCGCAGGC GGGACAGAGG AGGGACTTGA GGGCGTAGAG CTTGGGGGCG AGGAAGACGG    5460

ACTCGGGGGC GTAGGCGTCC GCGCCGCAGT GGGCGCAGAC GGTCTCGCAC TCCACGAGCC    5520

AGGTGAGGTC GGGCTGGTCG GGGTCAAAAA CCAGTTTCCC GCCGTTCTTT TTGATGCGTT    5580

TCTTACCTTT GGTCTCCATG AGCTCGTGTC CCCGCTGGGT GACAAAGAGG CTGTCCGTGT    5640

CCCCGTAGAC CGACTTTATG GGCCGGTCCT CGAGCGGTGT GCCGCGGTCC TCCTCGTAGA    5700

GGAACCCCGC CCACTCCGAG ACGAAAGCCC GGGTCCAGGC CAGCACGAAG GAGGCCACGT    5760

GGGACGGGTA GCGGTCGTTG TCCACCAGCG GGTCCACCTT TTCCAGGGTA TGCAAACACA    5820

TGTCCCCCTC GTCCACATCC AGGAAGGTGA TTGGCTTGTA AGTGTAGGCC ACGTGACCGG    5880

GGGTCCCGGC CGGGGGGGTA TAAAAGGGTG CGGGTCCCTG CTCGTCCTCA CTGTCTTCCG    5940
```

-continued

```
GATCGCTGTC CAGGAGCGCC AGCTGTTGGG GTAGGTATTC CCTCTCGAAG GCGGGCATGA    6000

CCTCGGCACT CAGGTTGTCA GTTTCTAGAA ACGAGGAGGA TTTGATATTG ACGGTGCCGG    6060

CGGAGATGCC TTTCAAGAGC CCCTCGTCCA TCTGGTCAGA AAAGACGATC TTTTTGTTGT    6120

CGAGCTTGGT GGCGAAGGAG CCGTAGAGGG CGTTGGAGAG GAGCTTGGCG ATGGAGCGCA    6180

TGGTCTGGTT TTTTTCCTTG TCGGCGCGCT CCTTGGCGGC GATGTTGAGC TGCACGTACT    6240

CGCGCGCCAC GCACTTCCAT TCGGGAAGA CGGTGGTCAG CTCGTCGGGC ACGATTCTGA     6300

CCTGCCAGCC CCGATTATGC AGGGTGATGA GGTCCACACT GGTGGCCACC TCGCCGCGCA    6360

GGGGCTCATT AGTCCAGCAG AGGCGTCCGC CCTTGCGCGA GCAGAAGGGG GGCAGGGGGT    6420

CCAGCATGAC CTCGTCGGGG GGGTCGGCAT CGATGGTGAA GATGCCGGGC AGGAGGTCGG    6480

GGTCAAAGTA GCTGATGGAA GTGGCCAGAT CGTCCAGGGC AGCTTGCCAT TCGCGCACGG    6540

CCAGCGCGCG CTCGTAGGGA CTGAGGGGCG TGCCCCAGGG CATGGGATGG GTAAGCGCGG    6600

AGGCGTACAT GCCGCAGATG TCGTAGACGT AGAGGGGCTC CTCGAGGATG CCGATGTAGG    6660

TGGGGTAGCA GCGCCCCCCG CGGATGCTGG CGCGCACGTA GTCATACAGC TCGTGCGAGG    6720

GGGCGAGGAG CCCCGGGCCC AGGTTGGTGC GACTGGGCTT TTCGGCGCGG TAGACGATCT    6780

GGCGGAAAAT GGCATGCGAG TTGGAGGAGA TGGTGGGCCT TTGGAAGATG TTGAAGTGGG    6840

CGTGGGGCAG TCCGACCGAG TCGCGGATGA AGTGGGCGTA GGAGTCTTGC AGCTTGGCGA    6900

CGAGCTCGGC GGTGACTAGG ACGTCCAGAG CGCAGTAGTC GAGGGTCTCC TGGATGATGT    6960

CATACTTGAG CTGTCCCTTT TGTTTCCACA GCTCGCGGTT GAGAAGGAAC TCTTCGCGGT    7020

CCTTCCAGTA CTCTTCGAGG GGGAACCCGT CCTGATCTGC ACGGTAAGAG CCTAGCATGT    7080

AGAACTGGTT GACGGCCTTG TAGGCGCAGC AGCCCTTCTC CACGGGGAGG GCGTAGGCCT    7140

GGGCGGCCTT GCGCAGGGAG GTGTGCGTGA GGGCGAAAGT GTCCCTGACC ATGACCTTGA    7200

GGAACTGGTG CTTGAAGTCG ATATCGTCGC AGCCCCCCTG CTCCCAGAGC TGGAAGTCCG    7260

TGCGCTTCTT GTAGGCGGGG TTGGGCAAAG CGAAAGTAAC ATCGTTGAAG AGGATCTTGC    7320

CCGCGCGGGG CATAAAGTTG CGAGTGATGC GGAAAGGTTG GGGCACCTCG GCCCGGTTGT    7380

TGATGACCTG GGCGGCGAGC ACGATCTCGT CGAAGCCGTT GATGTTGTGG CCCACGATGT    7440

AGAGTTCCAC GAATCGCGGA CGGCCCTTGA CGTGGGGCAG TTTCTTGAGC TCCTCGTAGG    7500

TGAGCTCGTC GGGGTCGCTG AGCCCGTGCT GCTCGAGCGC CCAGTCGGCG AGATGGGGGT    7560

TGGCGCGGAG GAAGGAAGTC CAGAGATCCA CGGCCAGGGC GGTTTGCAGA CGGTCCCGGT    7620

ACTGACGGAA CTGCTGCCCG ACGGCCATTT TTTCGGGGGT GACGCAGTAG AAGGTGCGGG    7680

GGTCCCCGTG CCAGCGATCC CATTTGAGCT GGAGGGCGAG ATCGAGGGCG AGCTCGACGA    7740

GCCGGTCGTC CCCGGAGAGT TTCATGACCA GCATGAAGGG GACGAGCTGC TTGCCGAAGG    7800

ACCCCATCCA GGTGTAGGTT TCCACATCGT AGGTGAGGAA GAGCCTTTCG GTGCGAGGAT    7860

GCGAGCCGAT GGGGAAGAAC TGGATCTCCT GCCACCAATT GGAGGAATGG CTGTTGATGT    7920

GATGGAAGTA GAAATGCCGA CGGCGCGCCG AACACTCGTG CTTGTGTTTA TACAAGCGGC    7980

CACAGTGCTC GCAACGCTGC ACGGGATGCA CGTGCTGCAC GAGCTGTACC TGAGTTCCTT    8040

TGACGAGGAA TTTCAGTGGG AAGTGGAGTC GTGGCGCCTG CATCTCGTGC TGTACTACGT    8100

CGTGGTGGTC GGCCTGGCCC TCTTCTGCCT CGATGGTGGT CATGCTGACG AGCCCGCGCG    8160

GGAGGCAGGT CCAGACCTCG GCGCGAGCGG GTCGGAGAGC GAGGACGAGG GCGCGCAGGC    8220

CGGAGCTGTC CAGGGTCCTG AGACGCTGCG GAGTCAGGTC AGTGGGCAGC GGCGGCGCGC    8280

GGTTGACTTG CAGGAGTTTT TCCAGGGCGC GCGGGAGGTC CAGATGGTAC TTGATCTCCA    8340
```

```
CCGCGCCATT GGTGGCGACG TCGATGGCTT GCAGGGTCCC GTGCCCCTGG GGTGTGACCA   8400

CCGTCCCCCG TTTCTTCTTG GGCGGCTGGG GCGACGGGGG CGGTGCCTCT TCCATGGTTA   8460

GAAGCGGCGG CGAGGACGCG CGCCGGGCGG CAGGGCGGC TCGGGCCCG GAGGCAGGGG     8520

CGGCAGGGGC ACGTCGGCGC CGCGCGCGGG TAGGTTCTGG TACTGCGCCC GGAGAAGACT   8580

GGCGTGAGCG ACGACGCGAC GGTTGACGTC CTGGATCTGA CGCCTCTGGG TGAAGGCCAC   8640

GGGACCCGTG AGTTTGAACC TGAAAGAGAG TTCGACAGAA TCAATCTCGG TATCGTTGAC   8700

GGCGGCCTGC CGCAGGATCT CTTGCACGTC GCCCGAGTTG TCCTGGTAGG CGATCTCGGT   8760

CATGAACTGC TCGATCTCCT CCTCTTGAAG GTCTCCGCGG CCGGCGCGCT CCACGGTGGC   8820

CGCGAGGTCG TTGGAGATGC GGCCCATGAG CTGCGAGAAG GCGTTCATGC CCGCCTCGTT   8880

CCAGACGCGG CTGTAGACCA CGACGCCCTC GGGATCGCCG GCGCGCATGA CCACCTGGGC   8940

GAGGTTGAGC TCCACGTGGC GCGTGAAGAC CGCGTAGTTG CAGAGGCGCT GGTAGAGGTA   9000

GTTGAGCGTG GTGGCGATGT GCTCGGTGAC GAAGAAATAC ATGATCCAGC GGCGGAGCGG   9060

CATCTCGCTG ACGTCGCCCA GCGCCTCCAA ACGTTCCATG GCCTCGTAAA AGTCCACGGC   9120

GAAGTTGAAA AACTGGGAGT TGCGCGCCGA GACGGTCAAC TCCTCCTCCA GAAGACGGAT   9180

GAGCTCGGCG ATGGTGGCGC GCACCTCGCG CTCGAAGGCC CCCGGGAGTT CCTCCACTTC   9240

CTCTTCTTCC TCCTCCACTA ACATCTCTTC TACTTCCTCC TCAGGCGGCA GTGGTGGCGG   9300

GGGAGGGGGC CTGCGTCGCC GGCGGCGCAC GGGCAGACGG TCGATGAAGC GCTCGATGGT   9360

CTCGCCGCGC CGGCGTCGCA TGGTCTCGGT GACGGCGCGC CCGTCCTCGC GGGGCCGCAG   9420

CGTGAAGACG CCGCCGCGCA TCTCCAGGTG GCCGGGGGGG TCCCCGTTGG GCAGGGAGAG   9480

GGCGCTGACG ATGCATCTTA TCAATTGCCC CGTAGGGACT CCGCGCAAGG ACCTGAGCGT   9540

CTCGAGATCC ACGGGATCTG AAAACCGCTG AACGAAGGCT TCGAGCCAGT CGCAGTCGCA   9600

AGGTAGGCTG AGCACGGTTT CTTCTGGCGG GTCATGTTGG TTGGGAGCGG GGCGGGCGAT   9660

GCTGCTGGTA ATGAAGTTGA AATAGGCGGT TCTGAGACGG CGGATGGTGG CGAGGAGCAC   9720

CAGGTCTTTG GGCCCGGCTT GCTGGATGCG CAGACGGTCG GCCATGCCCC AGGCGTGGTC   9780

CTGCACACCTG GCCAGGTCCT TGTAGTAGTC CTGCATGAGC CGCTCCACGG GCACCTCCTC   9840

CTCGCCCGCG CGGCCGTGCA TGCGCGTGAG CCCGAAGCCG CGCTGGGGCT GGACGAGCGC   9900

CAGGTCGGCG ACGACGCGCT CGGCGAGGAT GGCTTGCTGG ATCTGGGTGA GGGTGGTCTG   9960

GAAGTCATCA AAGTCGACGA AGCGGTGGTA GGCTCCGGTG TTGATGGTGT AGGAGCAGTT  10020

GGCCATGACG GACCAGTTGA CGGTCTGGTG GCCCGGACGC ACGAGCTCGT GGTACTTGAG  10080

GCGCGAGTAG GCGCGCGTGT CGAAGATGTA GTCGTTGCAG GTGCGCACCA GGTACTGGTA  10140

GCCGATGAGG AAGTCGGCGC GCGGCTGGCG GTAGAGCGGC CATCGCTCGG TGGCGGGGGC  10200

GCCGGGCGCG AGGTCCTCGA GCATGGTGCG GTGGTAGCCG TAGATGTACC TGGACATCCA  10260

GGTGATGCCG GCGGCGGTGG TGGAGGCGCG CGGGAACTCG CGGACGCGGT TCCAGATGTT  10320

GCGCAGCGGC AGGAAGTAGT TCATGGTGGG CACGGTCTGG CCCGTGAGGC GCGCGCAGTC  10380

GTGGATGCTC TATACGGGCA AAAACGAAAG CGGTCAGCGG CTCGACTCCG TGGCCTGGAG  10440

GCTAAGCGAA CGGGTTGGGC TGCGCGTGTA CCCCGGTTCG AATCTCGAAT CAGGCTGGAG  10500

CCGCAGCTAA CGTGGTATTG GCACTCCCGT CTCGACCCAA GCCTGCACCA ACCCTCCAGG  10560

ATACGGAGGC GGGTCGTTTT GCAACTTTTT TTTGGAGGCC GGATGAGACT AGTAAGCGCG  10620

GAAAGCGGCC GACCGCGATG GCTCGCTGCC GTAGTCTGGA GAAGAATCGC CAGGGTTGCG  10680
```

-continued

```
TTGCGGTGTG CCCCGGTTCG AGGCCGGCCG GATTCCGCGG CTAACGAGGG CGTGGCTGCC    10740

CCGTCGTTTC CAAGACCCCA TAGCCAGCCG ACTTCTCCAG TTACGGAGCG AGCCCCTCTT    10800

TTGTTTTGTT TGTTTTTGCC AGATGCATCC CGTACTGCGG CAGATGCGCC CCCACCACCC    10860

TCCACCGCAA CAACAGCCCC CTCCACAGCC GGCGCTTCTG CCCCCGCCCC AGCAGCAACT    10920

TCCAGCCACG ACCGCCGCGG CCGCCGTGAG CGGGGCTGGA CAGAGTTATG ATCACCAGCT    10980

GGCCTTGGAA GAGGGCGAGG GGCTGGCGCG CCTGGGGGCG TCGTCGCCGG AGCGGCACCC    11040

GCGCGTGCAG ATGAAAAGGG ACGCTCGCGA GGCCTACGTG CCCAAGCAGA ACCTGTTCAG    11100

AGACAGGAGC GGCGAGGAGC CCGAGGAGAT GCGCGCGGCC CGGTTCCACG CGGGGCGGGA    11160

GCTGCGGCGC GGCCTGGACC GAAAGAGGGT GCTGAGGGAC GAGGATTTCG AGGCGGACGA    11220

GCTGACGGGG ATCAGCCCCG CGCGCGCGCA CGTGGCCGCG GCCAACCTGG TCACGGCGTA    11280

CGAGCAGACC GTGAAGGAGG AGAGCAACTT CCAAAAATCC TTCAACAACC ACGTGCGCAC    11340

CCTGATCGCG CGCGAGGAGG TGACCCTGGG CCTGATGCAC CTGTGGGACC TGCTGGAGGC    11400

CATCGTGCAG AACCCCACCA GCAAGCCGCT GACGGCGCAG CTGTTCCTGG TGGTGCAGCA    11460

TAGTCGGGAC AACGAAGCGT TCAGGGAGGC GCTGCTGAAT ATCACCGAGC CCGAGGGCCG    11520

CTGGCTCCTG GACCTGGTGA ACATTCTGCA GAGCATCGTG GTGCAGGAGC GCGGGCTGCC    11580

GCTGTCCGAG AAGCTGGCGG CCATCAACTT CTCGGTGCTG AGTTTGGGCA AGTACTACGC    11640

TAGGAAGATC TACAAGACCC CGTACGTGCC CATAGACAAG GAGGTGAAGA TCGACGGGTT    11700

TTACATGCGC ATGACCCTGA AAGTGCTGAC CCTGAGCGAC GATCTGGGGG TGTACCGCAA    11760

CGACAGGATG CACCGTGCGG TGAGCGCCAG CAGGCGGCGC GAGCTGAGCG ACCAGGAGCT    11820

GATGCATAGT CTGCAGCGGG CCCTGACCGG GGCCGGGACC GAGGGGGAGA GCTACTTTGA    11880

CATGGGCGCG GACCTGCACT GGCAGCCCAG CCGCCGGGCC TTGGAGGCGG CGGCAGGACC    11940

CTACGTAGAA GAGGTGGACG ATGAGGTGGA CGAGGAGGGC GAGTACCTGG AAGACTGATG    12000

GCGCGACCGT ATTTTTGCTA GATGCAACAA CAACAGCCAC CTCCTGATCC CGCGATGCGG    12060

GCGGCGCTGC AGAGCCAGCC GTCCGGCATT AACTCCTCGG ACGATTGGAC CCAGGCCATG    12120

CAACGCATCA TGGCGCTGAC GACCCGCAAC CCCGAAGCCT TTAGACAGCA GCCCCAGGCC    12180

AACCGGCTCT CGGCCATCCT GGAGGCCGTG GTGCCCTCGC GCTCCAACCC CACGCACGAG    12240

AAGGTCCTGG CCATCGTGAA CGCGCTGGTG GAGAACAAGG CCATCCGCGG CGACGAGGCC    12300

GGCCTGGTGT ACAACGCGCT GCTGGAGCGC GTGGCCCGCT ACAACAGCAC CAACGTGCAG    12360

ACCAACCTGG ACCGCATGGT GACCGACGTG CGCGAGGCCG TGGCCCAGCG CGAGCGGTTC    12420

CACCGCGAGT CCAACCTGGG ATCCATGGTG GCGCTGAACG CCTTCCTCAG CACCCAGCCC    12480

GCCAACGTGC CCCGGGGCCA GGAGGACTAC ACCAACTTCA TCAGCGCCCT GCGCCTGATG    12540

GTGACCGAGG TGCCCCAGAG CGAGGTGTAC CAGTCCGGGC CGGACTACTT CTTCCAGACC    12600

AGTCGCCAGG GCTTGCAGAC CGTGAACCTG AGCCAGGCTT TCAAGAACTT GCAGGGCCTG    12660

TGGGGCGTGC AGGCCCCGGT CGGGGACCGC GCGACGGTGT CGAGCCTGCT GACGCCGAAC    12720

TCGCGCCTGC TGCTGCTGCT GGTGGCCCCC TTCACGGACA GCGGCAGCAT CAACCGCAAC    12780

TCGTACCTGG GCTACCTGAT TAACCTGTAC CGCGAGGCCA TCGGCCAGGC GCACGTGGAC    12840

GAGCAGACCT ACCAGGAGAT CACCCACGTG AGCCGCGCCC TGGGCCAGGA CGACCCGGGC    12900

AACCTGGAAG CCACCCTGAA CTTTTTGCTG ACCAACCGGT CGCAGAAGAT CCCGCCCCAG    12960

TACGCGCTCA GCACCGAGGA GGAGCGCATC CTGCGTTACG TGCAGCAGAG CGTGGGCCTG    13020

TTCCTGATGC AGGAGGGGGC CACCCCCAGC GCCGCGCTCG ACATGACCGC GCGCAACATG    13080
```

-continued

```
GAGCCCAGCA TGTACGCCAG CAACCGCCCG TTCATCAATA AACTGATGGA CTACTTGCAT    13140

CGGGCGGCCG CCATGAACTC TGACTATTTC ACCAACGCCA TCCTGAATCC CCACTGGCTC    13200

CCGCCGCCGG GGTTCTACAC GGGCGAGTAC GACATGCCCG ACCCCAATGA CGGGTTCCTG    13260

TGGGACGATG TGGACAGCAG CGTGTTCTCC CCCCGACCGG GTGCTAACGA GCGCCCCTTG    13320

TGGAAGAAGG AAGGCAGCGA CCGACGCCCG TCCTCGGCGC TGTCCGGCCG CGAGGGTGCT    13380

GCCGCGGCGG TGCCCGAGGC CGCCAGTCCT TTCCCGAGCT TGCCCTTCTC GCTGAACAGT    13440

ATCCGCAGCA GCGAGCTGGG CAGGATCACG CGCCCGCGCT TGCTGGGCGA AGAGGAGTAC    13500

TTGAATGACT CGCTGTTGAG ACCCGAGCGG GAGAAGAACT TCCCCAATAA CGGGATAGAA    13560

AGCCTGGTGG ACAAGATGAG CCGCTGGAAG ACGTATGCGC AGGAGCACAG GGACGATCCC    13620

CGGGCGTCGC AGGGGCCAC GAGCCGGGGC AGCGCCGCCC GTAAACGCCG GTGGCACGAC    13680

AGGCAGCGGG GACAGATGTG GGACGATGAG GACTCCGCCG ACGACAGCAG CGTGTTGGAC    13740

TTGGGTGGGA GTGGTAACCC GTTCGCTCAC CTGCGCCCCC GTATCGGGCG CATGATGTAA    13800

GAGAAACCGA AAATAAATGA TACTCACCAA GGCCATGGCG ACCAGCGTGC GTTCGTTTCT    13860

TCTCTGTTGT TGTTGTATCT AGTATGATGA GGCGTGCGTA CCCGGAGGGT CCTCCTCCCT    13920

CGTACGAGAG CGTGATGCAG CAGGCGATGG CGGCGGCGGC GATGCAGCCC CCGCTGGAGG    13980

CTCCTTACGT GCCCCCGCGG TACCTGGCGC CTACGGAGGG GCGGAACAGC ATTCGTTACT    14040

CGGAGCTGGC ACCCTTGTAC GATACCACCC GGTTGTACCT GGTGGACAAC AAGTCGGCGG    14100

ACATCGCCTC GCTGAACTAC CAGAACGACC ACAGCAACTT CCTGACCACC GTGGTGCAGA    14160

ACAATGACTT CACCCCCACG GAGGCCAGCA CCCAGACCAT CAACTTTGAC GAGCGCTCGC    14220

GGTGGGGCGG CCAGCTGAAA ACCATCATGC ACACCAACAT GCCCAACGTG AACGAGTTCA    14280

TGTACAGCAA CAAGTTCAAG GCGCGGGTGA TGGTCTCCCG CAAGACCCCC AATGGGGTGA    14340

CAGTGACAGA GGATTATGAT GGTAGTCAGG ATGAGCTGAA GTATGAATGG GTGGAATTTG    14400

AGCTGCCCGA AGGCAACTTC TCGGTGACCA TGACCATCGA CCTGATGAAC AACGCCATCA    14460

TCGACAATTA CTTGGCGGTG GGGCGGCAGA ACGGGGTGCT GGAGAGCGAC ATCGGCGTGA    14520

AGTTCGACAC TAGGAACTTC AGGCTGGGCT GGGACCCCGT GACCGAGCTG GTCATGCCCG    14580

GGGTGTACAC CAACGAGGCT TTCCATCCCG ATATTGTCTT GCTGCCCGGC TGCGGGGTGG    14640

ACTTCACCGA GAGCCGCCTC AGCAACCTGC TGGGCATTCG CAAGAGGCAG CCCTTCCAGG    14700

AAGGCTTCCA GATCATGTAC GAGGATCTGG AGGGGGGCAA CATCCCCGCG CTCCTGGATG    14760

TCGACGCCTA TGAGAAAAGC AAGGAGGATG CAGCAGCTGA AGCAACTGCA GCCGTAGCTA    14820

CCGCCTCTAC CGAGGTCAGG GGCGATAATT TTGCAAGCGC CGCAGCAGTG GCAGCGGCCG    14880

AGGCGGCTGA AACCGAAAGT AAGATAGTCA TTCAGCCGGT GGAGAAGGAT AGCAAGAACA    14940

GGAGCTACAA CGTACTACCG GACAAGATAA ACACCGCCTA CCGCAGCTGG TACCTAGCCT    15000

ACAACTATGG CGACCCCGAG AAGGGCGTGC GCTCCTGGAC GCTGCTCACC ACCTCGGACG    15060

TCACCTGCGG CGTGGAGCAA GTCTACTGGT CGCTGCCCGA CATGATGCAA GACCCGGTCA    15120

CCTTCCGCTC CACGCGTCAA GTTAGCAACT ACCCGGTGGT GGGCGCCGAG CTCCTGCCCG    15180

TCTACTCCAA GAGCTTCTTC AACGAGCAGG CCGTCTACTC GCAGCAGCTG CGCGCCTTCA    15240

CCTCGCTTAC GCACGTCTTC AACCGCTTCC CCGAGAACCA GATCCTCGTC CGCCCGCCCG    15300

CGCCCACCAT TACCACCGTC AGTGAAAACG TTCCTGCTCT CACAGATCAC GGGACCCTGC    15360

CGCTGCGCAG CAGTATCCGG GGAGTCCAGC GCGTGACCGT TACTGACGCC AGACGCCGCA    15420
```

-continued

```
CCTGCCCCTA CGTCTACAAG GCCCTGGGCA TAGTCGCGCC GCGCGTCCTC TCGAGCCGCA    15480

CCTTCTAAAT GTCCATTCTC ATCTCGCCCA GTAATAACAC CGGTTGGGGC CTGCGCGCGC    15540

CCAGCAAGAT GTACGGAGGC GCTCGCCAAC GCTCCACGCA ACACCCCGTG CGCGTGCGCG    15600

GGCACTTCCG CGCTCCCTGG GGCGCCCTCA AGGGCCGCGT GCGGTCGCGC ACCACCGTCG    15660

ACGACGTGAT CGACCAGGTG GTGGCCGACG CGCGCAACTA CACCCCCGCC GCCGCGCCCG    15720

TCTCCACCGT GGACGCCGTC ATCGACAGCG TGGTGGCGGA CGCGCGCCGG TACGCCCGCG    15780

CCAAGAGCCG GCGGCGGCGC ATCGCCCGGC GGCACCGGAG CACCCCCGCC ATGCGCGCGG    15840

CGCGAGCCTT GCTGCGCAGG GCCAGGCGCA CGGGACGCAG GGCCATGCTC AGGGCGGCCA    15900

GACGCGCGGC TTCAGGCGCC AGCGCCGGCA GGACCCGGAG ACGCGCGGCC ACGGCGGCGG    15960

CAGCGGCCAT CGCCAGCATG TCCCGCCCGC GGCGAGGGAA CGTGTACTGG GTGCGCGACG    16020

CCGCCACCGG TGTGCGCGTG CCCGTGCGCA CCCGCCCCCC TCGCACTTGA AGATGTTCAC    16080

TTCGCGATGT TGATGTGTCC CAGCGGCGAG GAGGATGTCC AAGCGCAAAT TCAAGGAAGA    16140

GATGCTCCAG GTCATCGCGC CTGAGATCTA CGGCCCTGCG GTGGTGAAGG AGGAAAGAAA    16200

GCCCCGCAAA ATCAAGCGGG TCAAAAAGGA CAAAAAGGAA GAAGAAAGTG ATGTGGACGG    16260

ATTGGTGGAG TTTGTGCGCG AGTTCGCCCC CCGGCGGCGC GTGCAGTGGC GCGGGCGGAA    16320

GGTGCAACCG GTGCTGAGAC CCGGCACCAC CGTGGTCTTC ACGCCCGGCG AGCGCTCCGG    16380

CACCGCTTCC AAGCGCTCCT ACGACGAGGT GTACGGGGAT GATGATATTC TGGAGCAGGC    16440

GGCCGAGCGC CTGGGCGAGT TTGCTTACGG CAAGCGCAGC CGTTCCGCAC CGAAGGAAGA    16500

GGCGGTGTCC ATCCCGCTGG ACCACGGCAA CCCCACGCCG AGCCTCAAGC CCGTGACCTT    16560

GCAGCAGGTG CTGCCGACCG CGGCGCCGCG CCGGGGGTTC AAGCGCGAGG GCGAGGATCT    16620

GTACCCCACC ATGCAGCTGA TGGTGCCCAA GCGCCAGAAG CTGGAAGACG TGCTGGAGAC    16680

CATGAAGGTG GACCCGGACG TGCAGCCCGA GGTCAAGGTG CGGCCCATCA AGCAGGTGGC    16740

CCCGGGCCTG GGCGTGCAGA CCGTGGACAT CAAGATTCCC ACGGAGCCCA TGGAAACGCA    16800

GACCGAGCCC ATGATCAAGC CCAGCACCAG CACCATGGAG GTGCAGACGG ATCCCTGGAT    16860

GCCATCGGCT CCTAGTCGAA GACCCCGGCG CAAGTACGGC GCGGCCAGCC TGCTGATGCC    16920

CAACTACGCG CTGCATCCTT CCATCATCCC CACGCCGGGC TACCGCGGCA CGCGCTTCTA    16980

CCGCGGTCAT ACCAGCAGCC GCCGCCGCAA GACCACCACT CGCCGCCGCC GTCGCCGCAC    17040

CGCCGCTGCA ACCACCCCTG CCGCCCTGGT GCGGAGAGTG TACCGCCGCG GCCGCGCACC    17100

TCTGACCCTG CCGCGCGCGC GCTACCACCC GAGCATCGCC ATTTAAACTT CGCCAGCTT    17160

TGCAGATCAA TGGCCCTCAC ATGCCGCCTT CGCGTTCCCA TTACGGGCTA CCGAGGAAGA    17220

AAACCGCGCC GTAGAAGGCT GGCGGGGAAC GGGATGCGTC GCCACCACCA CCGGCGGCGG    17280

CGCGCCATCA GCAAGCGGTT GGGGGGAGGC TTCCTGCCCG CGCTGATCCC CATCATCGCC    17340

GCGGCGATCG GGGCGATCCC CGGCATTGCT TCCGTGGCGG TGCAGGCCTC TCAGCGCCAC    17400

TGAGACACAC TTGAAACAT CTTGTAATAA ACCCATGGAC TCTGACGCTC CTGGTCCTGT    17460

GATGTGTTTT CGTAGACAGA TGGAAGACAT CAATTTTTCG TCCCTGGCTC CGCGACACGG    17520

CACGCGGCCG TTCATGGGCA CCTGGAGCGA CATCGGCACC AGCCAACTGA ACGGGGCGC    17580

CTTCAATTGG AGCAGTCTCT GGAGCGGGCT TAAGAATTTC GGGTCCACGC TTAAAACCTA    17640

TGGCAGCAAG GCGTGGAACA GCACCACAGG GCAGGCGCTG AGGGATAAGC TGAAAGAGCA    17700

GAACTTCCAG CAGAAGGTGG TCGATGGGCT CGCCTCGGGC ATCAACGGGG TGGTGGACCT    17760

GGCCAACCAG GCCGTGCAGC GGCAGATCAA CAGCCGCCTG GACCCGGTGC CGCCCGCCGG    17820
```

```
CTCCGTGGAG ATGCCGCAGG TGGAGGAGGA GCTGCCTCCC CTGGACAAGC GGGGCGAGAA   17880

GCGACCCCGC CCCGATGCGG AGGAGACGCT GCTGACGCAC ACGGACGAGC CGCCCCCGTA   17940

CGAGGAGGCG GTGAAACTGG GTCTGCCCAC CACGCGGCCC ATCGCGCCCC TGGCCACCGG   18000

GGTGCTGAAA CCCGAAAAGC CGCGACCCT GGACTTGCCT CCTCCCCAGC CTTCCCGCCC   18060

CTCTACAGTG GCTAAGCCCC TGCCGCCGGT GGCCGTGGCC CGCGCGCGAC CCGGGGGCAC   18120

CGCCCGCCCT CATGCGAACT GGCAGAGCAC TCTGAACAGC ATCGTGGGTC TGGGAGTGCA   18180

GAGTGTGAAG CGCCGCCGCT GCTATTAAAC CTACCGTAGC GCTTAACTTG CTTGTCTGTG   18240

TGTGTATGTA TTATGTCGCC GCCGCCGCTG TCCACCAGAA GGAGGAGTGA AGAGGCGCGT   18300

CGCCGAGTTG CAAGATGGCC ACCCCATCGA TGCTGCCCCA GTGGGCGTAC ATGCACATCG   18360

CCGGACAGGA CGCTTCGGAG TACCTGAGTC CGGGTCTGGT GCAGTTTGCC CGCGCCACAG   18420

ACACCTACTT CAGTCTGGGG AACAAGTTTA GGAACCCCAC GGTGGCGCCC ACGCACGATG   18480

TGACCACCGA CCGCAGCCAG CGGCTGACGC TGCGCTTCGT GCCCGTGGAC CGCGAGGACA   18540

ACACCTACTC GTACAAAGTG CGCTACACGC TGGCCGTGGG CGACAACCGC GTGCTGGACA   18600

TGGCCAGCAC CTACTTTGAC ATCCGCGGCG TGCTGGATCG GGGCCCTAGC TTCAAACCCT   18660

ACTCCGGCAC CGCCTACAAC AGTCTGGCCC CCAAGGGAGC ACCCAACACT TGTCAGTGGA   18720

CATATAAAGC CGATGGTGAA ACTGCCACAG AAAAAACCTA TACATATGGA AATGCACCCG   18780

TGCAGGGCAT TAACATCACA AAAGATGGTA TTCAACTTGG AACTGACACC GATGATCAGC   18840

CAATCTACGC AGATAAAACC TATCAGCCTG AACCTCAAGT GGGTGATGCT GAATGGCATG   18900

ACATCACTGG TACTGATGAA AAGTATGGAG GCAGAGCTCT TAAGCCTGAT ACCAAAATGA   18960

AGCCTTGTTA TGGTTCTTTT GCCAAGCCTA CTAATAAAGA AGGAGGTCAG GCAAATGTGA   19020

AAACAGGAAC AGGCACTACT AAAGAATATG ACATAGACAT GGCTTTCTTT GACAACAGAA   19080

GTGCGGCTGC TGCTGGCCTA GCTCCAGAAA TTGTTTTGTA TACTGAAAAT GTGGATTTGG   19140

AAACTCCAGA TACCCATATT GTATACAAAG CAGGCACAGA TGACAGCAGC TCTTCTATTA   19200

ATTTGGGTCA GCAAGCCATG CCCAACAGAC CTAACTACAT TGGTTTCAGA GACAACTTTA   19260

TCGGGCTCAT GTACTACAAC AGCACTGGCA ATATGGGGGT GCTGGCCGGT CAGGCTTCTC   19320

AGCTGAATGC TGTGGTTGAC TTGCAAGACA GAAACACCGA GCTGTCCTAC CAGCTCTTGC   19380

TTGACTCTCT GGGTGACAGA ACCCGGTATT TCAGTATGTG GAATCAGGCG GTGGACAGCT   19440

ATGATCCTGA TGTGCGCATT ATTGAAAATC ATGGTGTGGA GGATGAACTT CCCAACTATT   19500

GTTTCCCTCT GGATGCTGTT GGCAGAACAG ATACTTATCA GGGAATTAAG CTAATGGAA   19560

CTGATCAAAC CACATGGACC AAAGATGACA GTGTCAATGA TGCTAATGAG ATAGGCAAGG   19620

GTAATCCATT CGCCATGGAA ATCAACATCC AAGCCAACCT GTGGAGGAAC TTCCTCTACG   19680

CCAACGTGGC CCTGTACCTG CCCGACTCTT ACAAGTACAC GCCGGCCAAT GTTACCCTGC   19740

CCACCAACAC CAACACCTAC GATTACATGA ACGGCCGGGT GGTGGCGCCC TCGCTGGTGG   19800

ACTCCTACAT CAACATCGGG GCGCGCTGGT CGCTGGATCC CATGGACAAC GTGAACCCCT   19860

TCAACCACCA CCGCAATGCG GGGCTGCGCT ACCGCTCCAT GCTCCTGGGC AACGGGCGCT   19920

ACGTGCCCTT CCACATCCAG GTGCCCCAGA AATTTTTCGC CATCAAGAGC CTCCTGCTCC   19980

TGCCCGGGTC CTACACCTAC GAGTGGAACT TCCGCAAGGA CGTCAACATG ATCCTGCAGA   20040

GCTCCCTCGG CAACGACCTG CGCACGGACG GGGCCTCCAT CTCCTTCACC AGCATCAACC   20100

TCTACGCCAC CTTCTTCCCC ATGGCGCACA ACACGGCCTC CACGCTCGAG GCCATGCTGC   20160
```

```
GCAACGACAC CAACGACCAG TCCTTCAACG ACTACCTCTC GGCGGCCAAC ATGCTCTACC    20220

CCATCCCGGC CAACGCCACC AACGTGCCCA TCTCCATCCC CTCGCGCAAC TGGGCCGCCT    20280

TCCGCGGCTG GTCCTTCACG CGTCTCAAGA CCAAGGAGAC GCCCTCGCTG GGCTCCGGGT    20340

TCGACCCCTA CTTCGTCTAC TCGGGCTCCA TCCCCTACCT CGACGGCACC TTCTACCTCA    20400

ACCACACCTT CAAGAAGGTC TCCATCACCT TCGACTCCTC CGTCAGCTGG CCCGGCAACG    20460

ACCGGCTCCT GACGCCCAAC GAGTTCGAAA TCAAGCGCAC CGTCGACGGC GAGGGCTACA    20520

ACGTGGCCCA GTGCAACATG ACCAAGGACT GGTTCCTGGT CCAGATGCTG GCCCACTACA    20580

ACATCGGCTA CCAGGGCTTC TACGTGCCCG AGGGCTACAA GGACCGCATG TACTCCTTCT    20640

TCCGCAACTT CCAGCCCATG AGCCGCCAGG TGGTGGACGA GGTCAACTAC AAGGACTACC    20700

AGGCCGTCAC CCTGGCCTAC CAGCACAACA ACTCGGGCTT CGTCGGCTAC CTCGCGCCCA    20760

CCATGCGCCA GGGCCAGCCC TACCCCGCCA ACTACCCCTA CCCGCTCATC GGCAAGAGCG    20820

CCGTCACCAG CGTCACCCAG AAAAAGTTCC TCTGCGACAG GGTCATGTGG CGCATCCCCT    20880

TCTCCAGCAA CTTCATGTCC ATGGGCGCGC TCACCGACCT CGGCCAGAAC ATGCTCTATG    20940

CCAACTCCGC CCACGCGCTA GACATGAATT TCGAAGTCGA CCCCATGGAT GAGTCCACCC    21000

TTCTCTATGT TGTCTTCGAA GTCTTCGACG TCGTCCGAGT GCACCAGCCC CACCGCGGCG    21060

TCATCGAGGC CGTCTACCTG CGCACCCCCT TCTCGGCCGG TAACGCCACC ACCTAAGCTC    21120

TTGCTTCTTG CAAGCCATGG CCGCGGGCTC CGGCGAGCAG GAGCTCAGGG CCATCATCCG    21180

CGACCTGGGC TGCGGGCCCT ACTTCCTGGG CACCTTCGAT AAGCGCTTCC CGGGATTCAT    21240

GGCCCCGCAC AAGCTGGCCT GCGCCATCGT CAACACGGCC GGCCGCGAGA CCGGGGGCGA    21300

GCACTGGCTG GCCTTCGCCT GGAACCCGCG CTCGAACACC TGCTACCTCT TCGACCCCTT    21360

CGGGTTCTCG GACGAGCGCC TCAAGCAGAT CTACCAGTTC GAGTACGAGG GCCTGCTGCG    21420

CCGCAGCGCC CTGGCCACCG AGGACCGCTG CGTCACCCTG GAAAAGTCCA CCCAGACCGT    21480

GCAGGGTCCG CGCTCGGCCG CCTGCGGGCT CTTCTGCTGC ATGTTCCTGC ACGCCTTCGT    21540

GCACTGGCCC GACCGCCCCA TGGACAAGAA CCCCACCATG AACTTGCTGA CGGGGGTGCC    21600

CAACGGCATG CTCCAGTCGC CCCAGGTGGA ACCCACCCTG CGCCGCAACC AGGAGGCGCT    21660

CTACCGCTTC CTCAACTCCC ACTCCGCCTA CTTTCGCTCC CACCGCGCGC GCATCGAGAA    21720

GGCCACCGCC TTCGACCGCA TGAATCAAGA CATGTAAACC GTGTGTGTAT GTTAAATGTC    21780

TTTAATAAAC AGCACTTTCA TGTTACACAT GCATCTGAGA TGATTTATTT AGAAATCGAA    21840

AGGGTTCTGC CGGGTCTCGG CATGGCCCGC GGGCAGGGAC ACGTTGCGGA ACTGGTACTT    21900

GGCCAGCCAC TTGAACTCGG GGATCAGCAG TTTGGGCAGC GGGGTGTCGG GGAAGGAGTC    21960

GGTCCACAGC TTCCGCGTCA GTTGCAGGGC GCCCAGCAGG TCGGGCGCGG AGATCTTGAA    22020

ATCGCAGTTG GGACCCGCGT TCTGCGCGCG GGAGTTGCGG TACACGGGGT TGCAGCACTG    22080

GAACACCATC AGGGCCGGGT GCTTCACGCT CGCCAGCACC GTCGCGTCGG TGATGCTCTC    22140

CACGTCGAGG TCCTCGGCGT TGGCCATCCC GAAGGGGGTC ATCTTGCAGG TCTGCCTTCC    22200

CATGGTGGGC ACGCACCCGG GCTTGTGGTT GCAATCGCAG TGCAGGGGA TCAGCATCAT    22260

CTGGGCCTGG TCGGCGTTCA TCCCCGGGTA CATGGCCTTC ATGAAAGCCT CCAATTGCCT    22320

GAACGCCTGC TGGGCCTTGG CTCCCTCGGT GAAGAAGACC CCGCAGGACT TGCTAGAGAA    22380

CTGGTTGGTG GCGCACCCGG CGTCGTGCAC GCAGCAGCGC GCGTCGTTGT TGGCCAGCTG    22440

CACCACGCTG CGCCCCCAGC GGTTCTGGGT GATCTTGGCC GGTCGGGGT TCTCCTTCAG    22500

CGCGCGCTGC CCGTTCTCGC TCGCCACATC CATCTCGATC ATGTGCTCCT TCTGGATCAT    22560
```

-continued

```
GGTGGTCCCG TGCAGGCACC GCAGCTTGCC CTCGGCCTCG GTGCACCCGT GCAGCCACAG    22620

CGCGCACCCG TGCACTCCC AGTTCTTGTG GGCGATCTGG GAATGCGCGT GCACGAAGCC     22680

CTGCAGGAAG CGGCCCATCA TGGTGGTCAG GGTCTTGTTG CTAGTGAAGG TCAGCGGAAT    22740

GCCGCGGTGC TCCTCGTTGA TGTACAGGTG GCAGATGCGG CGGTACACCT CGCCCTGCTC    22800

GGGCATCAGC TGGAAGTTGG CTTTCAGGTC GGTCTCCACG CGGTAGCGGT CCATCAGCAT    22860

AGTCATGATT TCCATACCCT TCTCCCAGGC CGAGACGATG GGCAGGCTCA TAGGGTTCTT    22920

CACCATCATC TTAGCGCTAG CAGCCGCGGC CAGGGGGTCG CTCTCGTCCA GGGTCTCAAA    22980

GCTCCGCTTG CCGTCCTTCT CGGTGATCCG CACCGGGGGG TAGCTGAAGC CCACGGCCGC    23040

CAGCTCCTCC TCGGCCTGTC TTTCGTCCTC GCTGTCCTGG CTGACGTCCT GCAGGACCAC    23100

ATGCTTGGTC TTGCGGGGTT TCTTCTTGGG CGGCAGCGGC GGCGGAGATG TTGGAGATGG    23160

CGAGGGGAG CGCGAGTTCT CGCTCACCAC TACTATCTCT TCCTCTTCTT GGTCCGAGGC     23220

CACGCGGCGG TAGGTATGTC TCTTCGGGGG CAGAGGCGGA GGCGACGGGC TCTCGCCGCC    23280

GCGACTTGGC GGATGGCTGG CAGAGCCCCT TCCGCGTTCG GGGGTGCGCT CCCGGCGGCG    23340

CTCTGACTGA CTTCCTCCGC GGCCGGCCAT TGTGTTCTCC TAGGGAGGAA CAACAAGCAT    23400

GGAGACTCAG CCATCGCCAA CCTCGCCATC TGCCCCCACC GCCGACGAGA AGCAGCAGCA    23460

GCAGAATGAA AGCTTAACCG CCCCGCCGCC CAGCCCCGCC ACCTCCGACG CGGCCGTCCC    23520

AGACATGCAA GAGATGGAGG AATCCATCGA GATTGACCTG GGCTATGTGA CGCCCGCGGA    23580

GCACGAGGAG GAGCTGGCAG TGCGCTTTTC ACAAGAAGAG ATACACCAAG AACAGCCAGA    23640

GCAGGAAGCA GAGAATGAGC AGAGTCAGGC TGGGCTCGAG CATGACGGCG ACTACCTCCA    23700

CCTGAGCGGG GGGAGGACG CGCTCATCAA GCATCTGGCC CGGCAGGCCA CCATCGTCAA     23760

GGATGCGCTG CTCGACCGCA CCGAGGTGCC CCTCAGCGTG GAGGAGCTCA GCCGCGCCTA    23820

CGAGTTGAAC CTCTTCTCGC CGCGCGTGCC CCCCAAGCGC CAGCCCAATG GCACCTGCGA    23880

GCCCAACCCG CGCCTCAACT TCTACCCGGT CTTCGCGGTG CCCGAGGCCC TGGCCACCTA    23940

CCACATCTTT TTCAAGAACC AAAAGATCCC CGTCTCCTGC CGCGCCAACC GCACCCGCGC    24000

CGACGCCCTT TTCAACCTGG GTCCCGGCGC CCGCCTACCT GATATCGCCT CCTTGGAAGA    24060

GGTTCCCAAG ATCTTCGAGG GTCTGGGCAG CGACGAGACT CGGGCCGCGA ACGCTCTGCA    24120

AGGAGAAGGA GGAGAGCATG AGCACCACAG CGCCCTGGTC GAGTTGGAAG GCGACAACGC    24180

GCGGCTGGCG GTGCTCAAAC GCACGGTCGA GCTGACCCAT TTCGCCTACC CGGCTCTGAA    24240

CCTGCCCCCC AAAGTCATGA GCGCGGTCAT GGACCAGGTG CTCATCAAGC GCGCGTCGCC    24300

CATCTCCGAG GACGAGGGCA TGCAAGACTC CGAGGAGGGC AAGCCCGTGG TCAGCGACGA    24360

GCAGCTGGCC CGGTGGCTGG GTCCTAATGC TAGTCCCCAG AGTTTGGAAG AGCGGCGCAA    24420

ACTCATGATG GCCGTGGTCC TGGTGACCGT GGAGCTGGAG TGCCTGCGCC GCTTCTTCGC    24480

CGACGCGGAG ACCCTGCGCA AGGTCGAGGA GAACCTGCAC TACCTCTTCA GGCACGGGTT    24540

CGTGCGCCAG GCCTGCAAGA TCTCCAACGT GGAGCTGACC AACCTGGTCT CCTACATGGG    24600

CATCTTGCAC GAGAACCGCC TGGGGCAGAA CGTGCTGCAC ACCACCCTGC GCGGGGAGGC    24660

CCGGCGCGAC TACATCCGCG ACTGCGTCTA CCTCTACCTC TGCCACACCT GGCAGACGGG    24720

CATGGGCGTG TGGCAGCAGT GTCTGGAGGA GCAGAACCTG AAAGAGCTCT GCAAGCTCCT    24780

GCAGAAGAAC CTCAAGGGTC TGTGGACCGG GTTCGACGAG CGCACCACCG CCTCGGACCT    24840

GGCCGACCTC ATTTTCCCCG AGCGCCTCAG GCTGACGCTG CGCAACGGCC TGCCCGACTT    24900
```

```
TATGAGCCAA AGCATGTTGC AAAACTTTCG CTCTTTCATC CTCGAACGCT CCGGAATCCT    24960

GCCCGCCACC TGCTCCGCGC TGCCCTCGGA CTTCGTGCCG CTGACCTTCC GCGAGTGCCC    25020

CCCGCCGCTG TGGAGCCACT GCTACCTGCT GCGCCTGGCC AACTACCTGG CCTACCACTC    25080

GGACGTGATC GAGGACGTCA GCGGCGAGGG CCTGCTCGAG TGCCACTGCC GCTGCAACCT    25140

CTGCACGCCG CACCGCTCCC TGGCCTGCAA CCCCCAGCTG CTGAGCGAGA CCCAGATCAT    25200

CGGCACCTTC GAGTTGCAAG GGCCCAGCGA AGGCGAGGGT TCAGCCGCCA AGGGGGGTCT    25260

GAAACTCACC CCGGGGCTGT GGACCTCGGC CTACTTGCGC AAGTTCGTGC CCGAGGACTA    25320

CCATCCCTTC GAGATCAGGT TCTACGAGGA CCAATCCCAT CCGCCCAAGG CCGAGCTGTC    25380

GGCCTGCGTC ATCACCCAGG GGGCGATCCT GGCCCAATTG CAAGCCATCC AGAAATCCCG    25440

CCAAGAATTC TTGCTGAAAA AGGGCCGCGG GGTCTACCTC GACCCCCAGA CCGGTGAGGA    25500

GCTCAACCCC GGCTTCCCCC AGGATGCCCC GAGGAAACAA GAAGCTGAAA GTGGAGCTGC    25560

CGCCCGTGGA GGATTTGGAG GAAGACTGGG AGAACAGCAG TCAGGCAGAG GAGGAGGAGA    25620

TGGAGGAAGA CTGGGACAGC ACTCAGGCAG AGGAGGACAG CCTGCAAGAC AGTCTGGAGG    25680

AAGACGAGGA GGAGGCAGAG GAGGAGGTGG AAGAAGCAGC CGCCGCCAGA CCGTCGTCCT    25740

CGGCGGGGGA GAAAGCAAGC AGCACGGATA CCATCTCCGC TCCGGGTCGG GGTCCCGCTC    25800

GACCACACAG TAGATGGGAC GAGACCGGAC GATTCCCGAA CCCCACCACC CAGACCGGTA    25860

AGAAGGAGCG GCAGGGATAC AAGTCCTGGC GGGGGCACAA AAACGCCATC GTCTCCTGCT    25920

TGCAGGCCTG CGGGGGCAAC ATCTCCTTCA CCCGGCGCTA CCTGCTCTTC CACCGCGGGG    25980

TGAACTTTCC CCGCAACATC TTGCATTACT ACCGTCACCT CCACAGCCCC TACTACTTCC    26040

AAGAAGAGGC AGCAGCAGCA GAAAAAGACC AGCAGAAAAC CAGCAGCTAG AAAATCCACA    26100

GCGGCGGCAG CAGGTGGACT GAGGATCGCG GCGAACGAGC CGGCGCAAAC CCGGGAGCTG    26160

AGGAACCGGA TCTTTCCCAC CCTCTATGCC ATCTTCCAGC AGAGTCGGGG GCAGGAGCAG    26220

GAACTGAAAG TCAAGAACCG TTCTCTGCGC TCGCTCACCC GCAGTTGTCT GTATCACAAG    26280

AGCGAAGACC AACTTCAGCG CACTCTCGAG GACGCCGAGG CTCTCTTCAA CAAGTACTGC    26340

GCGCTCACTC TTAAAGAGTA GCCCGCGCCC GCCCAGTCGC AGAAAAAGGC GGGAATTACG    26400

TCACCTGTGC CCTTCGCCCT AGCCGCCTCC ACCCATCATC ATGAGCAAAG AGATTCCCAC    26460

GCCTTACATG TGGAGCTACC AGCCCCAGAT GGGCCTGGCC GCCGGTGCCG CCCAGGACTA    26520

CTCCACCCGC ATGAATTGGC TCAGCGCCGG GCCCGCGATG ATCTCACGGG TGAATGACAT    26580

CCGCGCCCAC CGAAACCAGA TACTCCTAGA ACAGTCAGCG CTCACCGCCA CGCCCCGCAA    26640

TCACCTCAAT CCGCGTAATT GGCCCGCCGC CCTGGTGTAC CAGGAAATTC CCCAGCCCAC    26700

GACCGTACTA CTTCCGCGAG ACGCCCAGGC CGAAGTCCAG CTGACTAACT CAGGTGTCCA    26760

GCTGGCGGGC GGCGCCACCC TGTGTCGTCA CCGCCCCGCT CAGGGTATAA AGCGGCTGGT    26820

GATCCGGGGC AGAGGCACAC AGCTCAACGA CGAGGTGGTG AGCTCTTCGC TGGGTCTGCG    26880

ACCTGACGGA GTCTTCCAAC TCGCCGGATC GGGGAGATCT TCCTTCACGC CTCGTCAGGC    26940

CGTCCTGACT TTGGAGAGTT CGTCCTCGCA GCCCCGCTCG GGTGGCATCG GCACTCTCCA    27000

GTTCGTGGAG GAGTTCACTC CCTCGGTCTA CTTCAACCCC TTCTCCGGCT CCCCCGGCCA    27060

CTACCCGGAC GAGTTCATCC CGAACTTCGA CGCCATCAGC GAGTCGGTGG ACGGCTACGA    27120

TTGAATGTCC CATGGTGGCG CAGCTGACCT AGCTCGGCTT CGACACCTGG ACCACTGCCG    27180

CCGCTTCCGC TGCTTCGCTC GGGATCTCGC CGAGTTTGCC TACTTTGAGC TGCCCGAGGA    27240

GCACCCTCAG GGCCCGGCCC ACGGAGTGCG GATCGTCGTC GAAGGGGGCC TCGACTCCCA    27300
```

```
CCTGCTTCGG ATCTTCAGCC AGCGTCCGAT CCTGGTCGAG CGCGAGCAAG GACAGACCCT   27360

TCTGACTCTG TACTGCATCT GCAACCACCC CGGCCTGCAT GAAAGTCTTT GTTGTCTGCT   27420

GTGTACTGAG TATAATAAAA GCTGAGATCA GCGACTACTC CGGACTTCCG TGTGTTCCTG   27480

AATCCATCAA CCAGTCTTTG TTCTTCACCG GGAACGAGAC CGAGCTCCAG CTCCAGTGTA   27540

AGCCCCACAA GAAGTACCTC ACCTGGCTGT TCCAGGGCTC CCCGATCGCC GTTGTCAACC   27600

ACTGCGACAA CGACGGAGTC CTGCTGAGCG GCCCTGCCAA CCTTACTTTT TCCACCCGCA   27660

GAAGCAAGCT CCAGCTCTTC CAACCCTTCC TCCCCGGGAC CTATCAGTGC GTCTCGGGAC   27720

CCTGCCATCA CACCTTCCAC CTGATCCCGA ATACCACAGC GTCGCTCCCC GCTACTAACA   27780

ACCAAACTAA CCTCCACCAA CGCCACCGTC GCGACCTTTC TGAATCTAAT ACTACCACCC   27840

ACACCGGAGG TGAGCTCCGA GGTCAACCAA CCTCTGGGAT TTACTACGGC CCCTGGGAGG   27900

TGGTTGGGTT AATAGCGCTA GGCCTAGTTG CGGGTGGGCT TTTGGTTCTC TGCTACCTAT   27960

ACCTCCCTTG CTGTTCGTAC TTAGTGGTGC TGTGTTGCTG GTTTAAGAAA TGGGGAAGAT   28020

CACCCTAGTG AGCTGCGGTG CGCTGGTGGC GGTGTTGCTT TCGATTGTGG GACTGGGCGG   28080

TGCGGCTGTA GTGAAGGAGA AGGCCGATCC CTGCTTGCAT TTCAATCCCA ACAAATGCCA   28140

GCTGAGTTTT CAGCCCGATG GCAATCGGTG CGCGGTACTA ATCAAGTGCG GATGGGAATG   28200

CGAGAACGTG AGAATCGAGT ACAATAACAA GACTCGGAAC AATACTCTCG CGTCCGTGTG   28260

GCAGCCCGGG GACCCCGAGT GGTACACCGT CTCTGTCCCC GGTGCTGACG GCTCCCCGCG   28320

CACCGTGAAT AATACTTTCA TTTTTGCGCA CATGTGCGAC ACGGTCATGT GGATGAGCAA   28380

GCAGTACGAT ATGTGGCCCC CCACGAAGGA GAACATCGTG GTCTTCTCCA TCGCTTACAG   28440

CCTGTGCACG GCGCTAATCA CCGCTATCGT GTGCCTGAGC ATTCACATGC TCATCGCTAT   28500

TCGCCCCAGA AATAATGCCG AAAAGAAAA ACAGCCATAA CGTTTTTTTT CACACCTTTT    28560

TCAGACCATG GCCTCTGTTA AATTTTTGCT TTTATTTGCC AGTCTCATTG CCGTCATTCA   28620

TGGAATGAGT AATGAGAAAA TTACTATTTA CACTGGCACT AATCACACAT TGAAAGGTCC   28680

AGAAAAAGCC ACAGAAGTTT CATGGTATTG TTATTTTAAT GAATCAGATG TATCTACTGA   28740

ACTCTGTGGA AACAATAACA AAAAAAATGA GAGCATTACT CTCATCAAGT TTCAATGTGG   28800

ATCTGACTTA ACCCTAATTA ACATCACTAG AGACTATGTA GGTATGTATT ATGGAACTAC   28860

AGCAGGCATT TCGGACATGG AATTTTATCA AGTTTCTGTG TCTGAACCCA CCACGCCTAG   28920

AATGACCACA ACCACAAAAA CTACACCTGT TACCACTATG CAGCTCACTA CCAATAACAT   28980

TTTTGCCATG CGTCAAATGG TCAACAATAG CACTCAACCC ACCCCACCCA GTGAGGAAAT   29040

TCCCAAATCC ATGATTGGCA TTATTGTTGC TGTAGTGGTG TGCATGTTGA TCATCGCCTT   29100

GTGCATGGTG TACTATGCCT TCTGCTACAG AAAGCACAGA CTGAACGACA AGCTGGAACA   29160

CTTACTAAGT GTTGAATTTT AATTTTTAG AACCATGAAG ATCCTAGGCC TTTTAATTTT    29220

TTCTATCATT ACCTCTGCTC TATGCAATTC TGACAATGAG GACGTTACTG TCGTTGTCGG   29280

ATCAAATTAT ACACTGAAAG GTCCAGCGAA GGGTATGCTT TCGTGGTATT GCTATTTTGG   29340

ATCTGACACT ACAGAAACTG AATTATGCAA TCTTAAGAAT GGCAAAATTC AAAATTCTAA   29400

AATTAACAAT TATATATGCA ATGGTACTGA TCTGATACTC CTCAATATCA CGAAATCATA   29460

TGCTGGCAGT TACACCTGCC CTGGAGATGA TGCTGACAGT ATGATTTTTT ACAAAGTAAC   29520

TGTTGTTGAT CCCACTACTC CACCTCCACC CACCACAACT ACTCACACCA CACACACAGA   29580

TCAAACCGCA GCAGAGGAGG CAGCAAAGTT AGCCTTGCAG GTCCAAGACA GTTCATTTGT   29640
```

```
TGGCATTACC CCTACACCTG ATCAGCGGTG TCCGGGGCTG CTAGTCAGCG GCATTGTCGG   29700

TGTGCTTTCG GGATTAGCAG TCATAATCAT CTGCATGTTC ATTTTTGCTT GCTGCTATAG   29760

AAGGCTTTAC CGACAAAAAT CAGACCCACT GCTGAACCTC TATGTTTAAT TTTTTCCAGA   29820

GTCATGAAGG CAGTTAGCGC TCTAGTTTTT TGTTCTTTGA TTGGCATTGT TTTTTGCAAT   29880

CCTATTCCTA AAGTTAGCTT TATTAAAGAT GTGAATGTTA CTGAGGGGGG CAATGTGACA   29940

CTGGTAGGTG TAGAGGGTGC TGAAAACACC ACCTGGACAA AATACCACCT CAATGGGTGG   30000

AAAGATATTT GCAATTGGAG TGTATTAGTT TATACATGTG AGGGAGTTAA TCTTACCATT   30060

GTCAATGCCA CCTCAGCTCA AAATGGTAGA ATTCAAGGAC AAAGTGTCAG TGTATCTAAT   30120

GGGTATTTTA CCCAACATAC TTTTATCTAT GACGTTAAAG TCATACCACT GCCTACGCCT   30180

AGCCCACCTA GCACTACCAC ACAGACAACC CACACTACAC AGACAACCAC ATACAGTACA   30240

TTAAATCAGC CTACCACCAC TACAGCAGCA GAGGTTGCCA GCTCGTCTGG GGTCCGAGTG   30300

GCATTTTTGA TGTGGGCCCC ATCTAGCAGT CCCACTGCTA GTACCAATGA GCAGACTACT   30360

GAATTTTTGT CCACTGTCGA GAGCCACACC ACAGCTACCT CCAGTGCCTT CTCTAGCACC   30420

GCCAATCTCT CCTCGCTTTC CTCTACACCA ATCAGTCCCG CTACTACTCC TAGCCCCGCT   30480

CCTCTTCCCA CTCCCCTGAA GCAAACAGAC GGCGGCATGC AATGGCAGAT CACCCTGCTC   30540

ATTGTGATCG GGTTGGTCAT CCTGGCCGTG TTGCTCTACT ACATCTTCTG CCGCCGCATT   30600

CCCAACGCGC ACCGCAAGCC GGTCTACAAG CCCATCATTG TCGGGCAGCC GGAGCCGCTT   30660

CAGGTGGAAG GGGGTCTAAG GAATCTTCTC TTCTCTTTTA CAGTATGGTG ATTGAACTAT   30720

GATTCCTAGA CAATTCTTGA TCACTATTCT TATCTGCCTC CTCCAAGTCT GTGCCACCCT   30780

CGCTCTGGTG GCCAACGCCA GTCCAGACTG TATTGGGCCC TTCGCCTCCT ACGTGCTCTT   30840

TGCCTTCACC ACCTGCATCT GCTGCTGTAG CATAGTCTGC CTGCTTATCA CCTTCTTCCA   30900

GTTCATTGAC TGGATCTTTG TGCGCATCGC CTACCTGCGC CACCACCCCC AGTACCGCGA   30960

CCAGCGAGTG GCGCGGCTGC TCAGGCTCCT CTGATAAGCA TGCGGGCTCT GCTACTTCTC   31020

GCGCTTCTGC TGTTAGTGCT CCCCCGTCCC GTCGACCCCC GGTCCCCCAC CCAGTCCCCC   31080

GAGGAGGTCC GCAAATGCAA ATTCCAAGAA CCCTGGAAAT TCCTCAAATG CTACCGCCAA   31140

AAATCAGACA TGCATCCCAG CTGGATCATG ATCATTGGGA TCGTGAACAT TCTGGCCTGC   31200

ACCCTCATCT CCTTTGTGAT TTACCCCTGC TTTGACTTTG GTTGGAACTC GCCAGAGGCG   31260

CTCTATCTCC CGCCTGAACC TGACACACCA CCACAGCAAC CTCAGGCACA CGCACTACCA   31320

CCACTACAGC CTAGGCCACA ATACATGCCC ATATTAGACT ATGAGGCCGA GCCACAGCGA   31380

CCCATGCTCC CCGCTATTAG TTACTTCAAT CTAACCGGCG GAGATGACTG ACCCACTGGC   31440

CAACAACAAC GTCAACGACC TTCTCCTGGA CATGGACGGC CGCGCCTCGG AGCAGCGACT   31500

CGCCCAACTT CGCATTCGCC AGCAGCAGGA GAGAGCCGTC AAGGAGCTGC AGGATGCGGT   31560

GGCCATCCAC CAGTGCAAGA GAGGCATCTT CTGCCTGGTG AAACAGGCCA AGATCTCCTA   31620

CGAGGTCACT CCAAACGACC ATCGCCTCTC CTACGAGCTC CTGCAGCAGC GCCAGAAGTT   31680

CACCTGCCTG GTCGGAGTCA ACCCCATCGT CATCACCCAG CAGTCTGGCG ATACCAAGGG   31740

GTGCATCCAC TGCTCCTGCG ACTCCCCCGA CTGCGTCCAC ACTCTGATCA AGACCCTCTG   31800

CGGCCTCCGC GACCTCCTCC CCATGAACTA ATCACCCCCT TATCCAGTGA AATAAAGATC   31860

ATATTGATGA TGATTTTACA GAAATAAAAA ATAATCATTT GATTTGAAAT AAAGATACAA   31920

TCATATTGAT GATTTGAGTT TAACAAAAAA ATAAAGAATC ACTTACTTGA AATCTGATAC   31980

CAGGTCTCTG TCCATGTTTT CTGCCAACAC CACTTCACTC CCCTCTTCCC AGCTCTGGTA   32040
```

-continued

```
CTGCAGGCCC CGGCGGGCTG CAAACTTCCT CCACACGCTG AAGGGGATGT CAAATTCCTC      32100

CTGTCCCTCA ATCTTCATTT TATCTTCTAT CAGATGTCCA AAAAGCGCGT CCGGGTGGAT      32160

GATGACTTCG ACCCCGTCTA CCCCTACGAT GCAGACAACG CACCGACCGT GCCCTTCATC      32220

AACCCCCCCT TCGTCTCTTC AGATGGATTC CAAGAGAAGC CCCTGGGGGT GTTGTCCCTG      32280

CGACTGGCCG ACCCCGTCAC CACCAAGAAC GGGGAAATCA CCCTCAAGCT GGGAGAGGGG      32340

GTGGACCTCG ATTCCTCGGG AAAACTCATC TCCAACACGG CCACCAAGGC CGCCGCCCCT      32400

CTCAGTTTTT CCAACAACAC CATTTCCCTT AACATGGATC ACCCCTTTTA CACTAAAGAT      32460

GGAAAATTAT CCTTACAAGT TTCTCCACCA TTAAATATAC TGAGAACAAG CATTCTAAAC      32520

ACACTAGCTT TAGGTTTTGG ATCAGGTTTA GGACTCCGTG GCTCTGCCTT GGCAGTACAG      32580

TTAGTCTCTC CACTTACATT TGATACTGAT GGAAACATAA AGCTTACCTT AGACAGAGGT      32640

TTGCATGTTA CAACAGGAGA TGCAATTGAA AGCAACATAA GCTGGGCTAA AGGTTTAAAA      32700

TTTGAAGATG GAGCCATAGC AACCAACATT GGAAATGGGT TAGAGTTTGG AAGCAGTAGT      32760

ACAGAAACAG GTGTTGATGA TGCTTACCCA ATCCAAGTTA AACTTGGATC TGGCCTTAGC      32820

TTTGACAGTA CAGGAGCCAT AATGGCTGGT AACAAAGAAG ACGATAAACT CACTTTGTGG      32880

ACAACACCTG ATCCATCACC AAACTGTCAA ATACTCGCAG AAAATGATGC AAAACTAACA      32940

CTTTGCTTGA CTAAATGTGG TAGTCAAATA CTGGCCACTG TGTCAGTCTT AGTTGTAGGA      33000

AGTGGAAACC TAAACCCCAT TACTGGCACC GTAAGCAGTG CTCAGGTGTT TCTACGTTTT      33060

GATGCAAACG GTGTTCTTTT AACAGAACAT TCTACACTAA AAAAATACTG GGGGTATAGG      33120

CAGGGAGATA GCATAGATGG CACTCCATAT ACCAATGCTG TAGGATTCAT GCCCAATTTA      33180

AAAGCTTATC CAAAGTCACA AAGTTCTACT ACTAAAAATA ATATAGTAGG GCAAGTATAC      33240

ATGAATGGAG ATGTTTCAAA ACCTATGCTT CTCACTATAA CCCTCAATGG TACTGATGAC      33300

AGCAACAGTA CATATTCAAT GTCATTTTCA TACACCTGGA CTAATGGAAG CTATGTTGGA      33360

GCAACATTTG GGGCTAACTC TTATACCTTC TCATACATCG CCCAAGAATG AACACTGTAT      33420

CCCACCCTGC ATGCCAACCC TTCCCACCCC ACTCTGTGGA ACAAACTCTG AAACACAAAA      33480

TAAAATAAAG TTCAAGTGTT TTATTGATTC AACAGTTTTA CAGGATTCGA GCAGTTATTT      33540

TTCCTCCACC CTCCCAGGAC ATGGAATACA CCACCCTCTC CCCCCGCACA GCCTTGAACA      33600

TCTGAATGCC ATTGGTGATG GACATGCTTT TGGTCTCCAC GTTCCACACA GTTTCAGAGC      33660

GAGCCAGTCT CGGGTCGGTC AGGGAGATGA AACCCTCCGG GCACTCCGCC ATCTGCACCT      33720

CACAGCTCAA CAGCTGAGGA TTGTCCTCGG TGGTCGGGAT CACGGTTATC TGGAAGAAGC      33780

AGAAGAGCGG CGGTGGGAAT CATAGTCCGC GAACGGGATC GGCCGGTGGT GTCGCATCAG      33840

GCCCCGCAGC AGTCGCTGCC GCCGCCGCTC CGTCAAGCTG CTGCTCAGGG GGTCCGGGTC      33900

CAGGGACTCC CTCAGCATGA TGCCCACGGC CCTCAGCATC AGTCGTCTGG TGCGGCGGGC      33960

GCAGCAGCGC ATGCGGATCT CGCTCAGGTC GCTGCAGTAC GTGCAACACA GAACCACCAG      34020

GTTGTTCAAC AGTCCATAGT TCAACACGCT CCAGCCGAAA CTCATCGCGG GAAGGATGCT      34080

ACCCACGTGG CCGTCGTACC AGATCCTCAG GTAAATCAAG TGGTGCCCCC TCCAGAACAC      34140

GCTGCCCACG TACATGATCT CCTTGGGCAT GTGGCGGTTC ACCACCTCCC GGTACCACAT      34200

CACCCTCTGG TTGAACATGC AGCCCCGGAT GATCCTGCGG AACCACAGGG CCAGCACCGC      34260

CCCGCCCGCC ATGCAGCGAA GAGACCCCGG GTCCCGGCAA TGGCAATGGA GGACCCACCG      34320

CTCGTACCCG TGGATCATCT GGGAGCTGAA CAAGTCTATG TTGGCACAGC ACAGGCATAT      34380
```

-continued

```
GCTCATGCAT CTCTTCAGCA CTCTCAACTC CTCGGGGTC AAAACCATAT CCCAGGGCAC    34440

GGGGAACTCT TGCAGGACAG CGAACCCCGC AGAACAGGGC AATCCTCGCA CAGAACTTAC    34500

ATTGTGCATG GACAGGGTAT CGCAATCAGG CAGCACCGGG TGATCCTCCA CCAGAGAAGC    34560

GCGGGTCTCG GTCTCCTCAC AGCGTGGTAA GGGGGCCGGC CGATACGGGT GATGGCGGGA    34620

CGCGGCTGAT CGTGTTCGCG ACCGTGTCAT GATGCAGTTG CTTTCGGACA TTTTCGTACT    34680

TGCTGTAGCA GAACCTGGTC CGGGCGCTGC ACACCGATCG CCGGCGGCGG TCTCGGCGCT    34740

TGGAACGCTC GGTGTTGAAA TTGTAAAACA GCCACTCTCT CAGACCGTGC AGCAGATCTA    34800

GGGCCTCAGG AGTGATGAAG ATCCCATCAT GCCTGATGGC TCTGATCACA TCGACCACCG    34860

TGGAATGGGC CAGACCCAGC CAGATGATGC AATTTTGTTG GGTTTCGGTG ACGGCGGGGG    34920

AGGGAAGAAC AGGAAGAACC ATGATTAACT TTTAATCCAA ACGGTCTCGG AGTACTTCAA    34980

AATGAAGATC GCGGAGATGG CACCTCTCGC CCCCGCTGTG TTGGTGGAAA ATAACAGCCA    35040

GGTCAAAGGT GATACGGTTC TCGAGATGTT CCACGGTGGC TTCCAGCAAA GCCTCCACGC    35100

GCACATCCAG AAACAAGACA ATAGCGAAAG CGGGAGGGTT CTCTAATTCC TCAATCATCA    35160

TGTTACACTC CTGCACCATC CCCAGATAAT TTTCATTTTT CCAGCCTTGA ATGATTCGAA    35220

CTAGTTCGTG AGGTAAATCC AAGCCAGCCA TGATAAAGAG CTCGCGCAGA GCGCCCTCCA    35280

CCGGCATTCT TAAGCACACC CTCATAATTC CAAGATATTC TGCTCCTGGT TCACCTGCAG    35340

CAGATTGACA AGCGGAATAT CAAAATCTCT GCCGCGATCC CTGAGCTCCT CCCTCAGCAA    35400

TAACTGTAAG TACTCTTTCA TATCCTCTCC GAAATTTTTA GCCATAGGAC CACCAGGAAT    35460

AAGATTAGGG CAAGCCACAG TACAGATAAA CCGAAGTCCT CCCCAGTGAG CATTGCCAAA    35520

TGCAAGACTG CTATAAGCAT GCTGGCTAGA CCCGGTGATA TCTTCCAGAT AACTGGACAG    35580

AAAATCGCCC AGGCAATTTT TAAGAAAATC AACAAAAGAA AAATCCTCCA GGTGGACGTT    35640

TAGAGCCTCG GGAACAACGA TGAAGTAAAT GCAAGCGGTG CGTTCCAGCA TGGTTAGTTA    35700

GCTGATCTGT AGAAAAAACA AAAATGAACA TTAAACCATG CTAGCCTGGC GAACAGGTGG    35760

GTAAATCGTT CTCTCCAGCA CCAGGCAGGC CACGGGTCT CCGGCGCGAC CCTCGTAAAA    35820

ATTGTCGCTA TGATTGAAAA CCATCACAGA GAGACGTTCC CGGTGGCCGG CGTGAATGAT    35880

TCGACAAGAT GAATACACCC CCGGAACATT GGCGTCCGCG AGTGAAAAAA AGCGCCCGAG    35940

GAAGCAATAA GGCACTACAA TGCTCAGTCT CAAGTCCAGC AAAGCGATGC CATGCGGATG    36000

AAGCACAAAA TTCTCAGGTG CGTACAAAAT GTAATTACTC CCCTCCTGCA CAGGCAGCAA    36060

AGCCCCCGAT CCCTCCAGGT ACACATACAA AGCCTCAGCG TCCATAGCTT ACCGAGCAGC    36120

AGCACACAAC AGGCGCAAGA GTCAGAGAAA GGCTGAGCTC TAACCTGTCC ACCCGCTCTC    36180

TGCTCAATAT ATAGCCCAGA TCTACACTGA CGTAAAGGCC AAAGTCTAAA AATACCCGCC    36240

AAATAATCAC ACACGCCCAG CACACGCCCA GAAACCGGTG ACACACTCAA AAAAATACGC    36300

GCACTTCCTC AAACGCCCAA AACTGCCGTC ATTTCCGGGT TCCCACGCTA CGTCATCAAA    36360

ACACGACTTT CAAATTCCGT CGACCGTTAA AAACGTCACC CGCCCGCCC CTAACGGTCG    36420

CCCGTCTCTC AGCCAATCAG CGCCCCGCAT CCCCAAATTC AAACACCTCA TTTGCATATT    36480

AACGCGCACA AAAGTTTGA GGTATATTAT TGATGATGG                            36519
```

(2) INFORMATION FOR SEQ ID NO:3:

(i) SEQUENCE CHARACTERISTICS:
        (A) LENGTH: 8299 base pairs
        (B) TYPE: nucleic acid
        (C) STRANDEDNESS: double (D) TOPOLOGY: unknown (ii) MOLECULE TYPE: cDNA (xi) SEQUENCE DESCRIPTION: SEQ ID NO:3:

```
GCCCAATACG CAAACCGCCT CTCCCCGCGC GTTGGCCGAT TCATTAATGC AGCTGCGCGC      60
TCGCTCGCTC ACTGAGGCCG CCCGGGCAAA GCCCGGGCGT CGGGCGACCT TTGGTCGCCC     120
GGCCTCAGTG AGCGAGCGAG CGCGCAGAGA GGGAGTGGCC AACTCCATCA CTAGGGGTTC     180
CTTGTAGTTA ATGATTAACC CGCCATGCTA CTTATCTACA TCATCGATGA ATTCGAGCTT     240
GCATGCCTGC AGGTCGTTAC ATAACTTACG GTAAATGGCC CGCCTGGCTG ACCGCCCAAC     300
GACCCCCGCC CATTGACGTC AATAATGACG TATGTTCCCA TAGTAACGCC AATAGGGACT     360
TTCCATTGAC GTCAATGGGT GGAGTATTTA CGGTAAACTG CCCACTTGGC AGTACATCAA     420
GTGTATCATA TGCCAAGTAC GCCCCCTATT GACGTCAATG ACGGTAAATG GCCCGCCTGG     480
CATTATGCCC AGTACATGAC CTTATGGGAC TTTCCTACTT GGCAGTACAT CTACGTATTA     540
GTCATCGCTA TTACCATGGT GATGCGGTTT TGGCAGTACA TCAATGGGCG TGGATAGCGG     600
TTTGACTCAC GGGGATTTCC AAGTCTCCAC CCCATTGACG TCAATGGGAG TTTGTTTTGG     660
CACCAAAATC AACGGGACTT TCCAAAATGT CGTAACAACT CCGCCCCATT GACGCAAATG     720
GGCGGTAGGC GTGTACGGTG GGAGGTCTAT ATAAGCAGAG CTCGTTTAGT GAACCGTCAG     780
ATCGCCTGGA GACGCCATCC ACGCTGTTTT GACCTCCATA GAAGACACCG GGACCGATCC     840
AGCCTCCGGA CTCTAGAGGA TCCGGTACTC GACCCGAGCT CGGATCCACT AGTAACGGCC     900
GCCAGTGTGC TGGAATTCTG CACTCCAGGC TGCCCGGGTT TGCATGCTGC TGCTGCTGCT     960
GCTGCTGGGC CTGAGGCTAC AGCTCTCCCT GGGCATCATC CTAGTTGAGG AGGAGAACCC    1020
GGACTTCTGG AACCGCGAGG CAGCCGAGGC CCTGGGTGCC GCCAAGAAGC TGCAGCCTGC    1080
ACAGACAGCC GCCAAGAACC TCATCATCTT CCTGGGCGAT GGGATGGGGG TGTCTACGGT    1140
GACAGCTGCC AGGATCCTAA AAGGGCAGAA GAAGGACAAA CTGGGGCCTG AGATACCCCT    1200
GGCCATGGAC CGCTTCCCAT ATGTGGCTCT GTCCAAGACA TACAATGTAG ACAAACATGT    1260
GCCAGACAGT GGAGCCACAG CCACGGCCTA CCTGTGCGGG GTCAAGGGCA ACTTCCAGAC    1320
CATTGGCTTG AGTGCAGCCG CCCGCTTTAA CCAGTGCAAC ACGACACGCG GCAACGAGGT    1380
CATCTCCGTG ATGAATCGGG CCAAGAAAGC AGGGAAGTCA GTGGGAGTGG TAACCACCAC    1440
ACGAGTGCAG CACGCCTCGC CAGCCGGCAC CTACGCCCAC ACGGTGAACC GCAACTGGTA    1500
CTCGGACGCC GACGTGCCTG CCTCGGCCCG CCAGGAGGGG TGCCAGGACA TCGCTACGCA    1560
GCTCATCTCC AACATGGACA TTGATGTGAT CCTAGGTGGA GGCCGAAAGT ACATGTTTCG    1620
CATGGGAACC CCAGACCCTG AGTACCCAGA TGACTACAGC CAAGGTGGGA CCAGGCTGGA    1680
CGGGAAGAAT CTGGTGCAGG AATGGCTCGG CGAACGCCAG GGTGCCCGGT ACGTGTGGAA    1740
CCGCACTGAG CTCATGCAGG CTTCCCTGGA CCCGTCTGTG ACCCATCTCA TGGGTCTCTT    1800
TGAGCCTGGA GACATGAAAT ACGAGATCCA CCGAGACTCC ACACTGGACC CTCCCTGAT     1860
GGAGATGACA GAGGCTGCCC TGCGCCTGCT GAGCAGACAC CCCCGCGGCT TCTTCCTCTT    1920
CGTGGAGGGT GGTCGCATCG ACCATGGTCA TCATGAAAGC AGGGCTTACC GGGCACTGAC    1980
TGAGACGATC ATGTTCGACG ACGCCATTGA GAGGGCGGGC CAGCTCACCA GCGAGGAGGA    2040
CACGCTGAGC CTCGTCACTG CCGACCACTC CCACGTCTTC TCCTTCGGAG CTACCCCCT     2100
GCGAGGGAGC TCCTTCATCG GGCTGGCCGC TGGCAAGGCC CGGGACAGGA AGGCCTACAC    2160
GGTCCTCCTA TACGGAAACG GTCCAGGCTA TGTGCTCAAG GACGGCGCCC GGCCGGATGT    2220
```

```
TACCGAGAGC GAGAGCGGGA GCCCCGAGTA TCGGCAGCAG TCAGCAGTGC CCCTGGACGA    2280

AGAGACCCAC GCAGGCGAGG ACGTGGCGGT GTTCGCGCGC GGCCCGCAGG CGCACCTGGT    2340

TCACGGCGTG CAGGAGCAGA CCTTCATAGC GCACGTCATG GCCTTCGCCG CCTGCCTGGA    2400

GCCCTACACC GCCTGCGACC TGGCGCCCCC CGCCGGCACC ACCGACGCCG CGCACCCGGG    2460

GCGGTCCGTG GTCCCCGCGT TGCTTCCTCT GCTGGCCGGG ACCCTGCTGC TGCTGGAGAC    2520

GGCCACTGCT CCCTGAGTGT CCCGTCCCTG GGGCTCCTGC TTCCCCATCC CGGAGTTCTC    2580

CTGCTCCCCA CCTCCTGTCG TCCTGCCTGG CCTCCAGCCC GAGTCGTCAT CCCCGGAGTC    2640

CCTATACAGA GGTCCTGCCA TGGAACCTTC CCCTCCCCGT GCGCTCTGGG GACTGAGCCC    2700

ATGACACCAA ACCTGCCCCT TGGCTGCTCT CGGACTCCCT ACCCCAACCC CAGGGACTGC    2760

AGGTTGTGCC CTGTGGCTGC CTGCACCCCA GGAAAGGAGG GGGCTCAGGC CATCCAGCCA    2820

CCACCTACAG CCCAGTGGGG TCGAGACAGA TGGTCAGTCT GGAGGATGAC GTGGCGTGAA    2880

GCTGGCCGCG GGGATCCAGA CATGATAAGA TACATTGATG AGTTTGGACA AACCACAACT    2940

AGAATGCAGT GAAAAAAATG CTTTATTTGT GAAATTTGTG ATGCTATTGC TTTATTTGTA    3000

ACCATTATAA GCTGCAATAA ACAAGTTAAC AACAACAATT GCATTCATTT TATGTTTCAG    3060

GTTCAGGGGG AGGTGTGGGA GGTTTTTTCG GATCCTCTAG AGTCGACTCT AGANNNNNNN    3120

NNNNNNNNNN NNNNNNNNNN NNNNNNNNNN NNNNNNNNNN NNNNNNNNNN NNNNNNNNNN    3180

NNNNNNNNNN NNNNNNNNNN NNNNNNNNNN NNNNNNNNNN NNNNNNNNNN NNNNNNNNNN    3240

NNNNNNNNNN NNNNNNNNNN NNNNNNNNNN NNNNNNNNNN NNNNNNNNNN NNNNNNNNNN    3300

NNNNNNNNNN NNNNNNNNNN NNNNNNNNNN NNNNNNNNNN NNNNNNNNNN NNNNNNNNNN    3360

NNNNNNNNNN NNNNNNNNNN NNNNNNNNNN NNNGGATCCC CATGACTACG TCCGGCGTTC    3420

CATTTGGCAT GACACTACGA CCAACACGAT CTCGGTTGTC TCGGCGCACT CCGTACAGTA    3480

GGGATCGTCT ACCTCCTTTT GAGACAGAAA CCCGCGCTAC CATACTGGAG GATCATCCGC    3540

TGCTGCCCGA ATGTAACACT TTGACAATGC ACAACGTGAG TTACGTGCGA GGTCTTCCCT    3600

GCAGTGTGGG ATTTACGCTG ATTCAGGAAT GGGTTGTTCC CTGGGATATG GTTCTAACGC    3660

GGGAGGAGCT TGTAATCCTG AGGAAGTGTA TGCACGTGTG CCTGTGTTGT GCCAACATTG    3720

ATATCATGAC GAGCATGATG ATCCATGGTT ACGAGTCCTG GGCTCTCCAC TGTCATTGTT    3780

CCAGTCCCGG TTCCCTGCAG TGTATAGCCG GCGGGCAGGT TTTGGCCAGC TGGTTTAGGA    3840

TGGTGGTGGA TGGCGCCATG TTTAATCAGA GGTTTATATG GTACCGGGAG GTGGTGAATT    3900

ACAACATGCC AAAAGAGGTA ATGTTTATGT CCAGCGTGTT TATGAGGGGT CGCCACTTAA    3960

TCTACCTGCG CTTGTGGTAT GATGGCCACG TGGGTTCTGT GGTCCCCGCC ATGAGCTTTG    4020

GATACAGCGC CTTGCACTGT GGGATTTTGA ACAATATTGT GGTGCTGTGC TGCAGTTACT    4080

GTGCTGATTT AAGTGAGATC AGGGTGCGCT GCTGTGCCCG GAGGACAAGG CGCCTTATGC    4140

TGCGGGCGGT GCGAATCATC GCTGAGGAGA CCACTGCCAT GTTGTATTCC TGCAGGACGG    4200

AGCGGCGGCG GCAGCAGTTT ATTCGCGCGC TGCTGCAGCA CCACCGCCCT ATCCTGATGC    4260

ACGATTATGA CTCTACCCCC ATGTAGGGAT CCCCATCACT AGTGCGGCCG CGGGGATCCA    4320

GACATGATAA GATACATTGA TGAGTTTGGA CAAACCACAA CTAGAATGCA GTGAAAAAAA    4380

TGCTTTATTT GTGAAATTTG TGATGCTATT GCTTTATTTG TAACCATTAT AAGCTGCAAT    4440

AAACAAGTTA ACAACAACAA TTGCATTCAT TTTATGTTTC AGGTTCAGGG GGAGGTGTGG    4500

GAGGTTTTTT CGGATCCTCT AGAGTCGACC TGCAGGCATG CAAGCTGTAG ATAAGTAGCA    4560
```

```
TGGCGGGTTA ATCATTAACT ACAAGGAACC CCTAGTGATG GAGTTGGCCA CTCCCTCTCT    4620

GCGCGCTCGC TCGCTCACTG AGGCCGGGCG ACCAAAGGTC GCCCGACGCC CGGGCTTTGC    4680

CCGGGCGGCC TCAGTGAGCG AGCGAGCGCG CAGCTGGCGT AATAGCGAAG AGGCCCGCAC    4740

CGATCGCCCT TCCCAACAGT TGCGCAGCCT GAATGGCGAA TGGAANTTCC AGACGATTGA    4800

GCGTCAAAAT GTAGGTATTT CCATGAGCGT TTTTCCTGTT GCAATGGCTG GCGGTAATAT    4860

TGTTCTGGAT ATTACCAGCA AGGCCGATAG TTTGAGTTCT TCTACTCAGG CAAGTGATGT    4920

TATTACTAAT CAAAGAAGTA TTGCGACAAC GGTTAATTTG CGTGATGGAC AGACTCTTTT    4980

ACTCGGTGGC CTCACTGATT ATAAAAACAC TTCTCAGGAT TCTGGCGTAC CGTTCCTGTC    5040

TAAAATCCCT TTAATCGGCC TCCTGTTTAG CTCCCGCTCT GATTCTAACG AGGAAAGCAC    5100

GTTATACGTG CTCGTCAAAG CAACCATAGT ACGCGCCCTG TAGCGGCGCA TTAAGCGCGG    5160

CGGGTGTGGT GGTTACGCGC AGCGTGACCG CTACACTTGC CAGCGCCCTA GCGCCCGCTC    5220

CTTTCGCTTT CTTCCCTTCC TTTCTCGCCA CGTTCGCCGG CTTTCCCCGT CAAGCTCTAA    5280

ATCGGGGGCT CCCTTTAGGG TTCCGATTTA GTGCTTTACG GCACCTCGAC CCCAAAAAAC    5340

TTGATTAGGG TGATGGTTCA CGTAGTGGGC CATCGCCCTG ATAGACGGTT TTTCGCCCTT    5400

TGACGTTGGA GTCCACGTTC TTTAATAGTG GACTCTTGTT CCAAACTGGA ACAACACTCA    5460

ACCCTATCTC GGTCTATTCT TTTGATTTAT AAGGGATTTT GCCGATTTCG GCCTATTGGT    5520

TAAAAAATGA GCTGATTTAA CAAAAATTTA ACGCGAATTT TAACAAAATA TTAACGTTTA    5580

CAATTTAAAT ATTTGCTTAT ACAATCTTCC TGTTTTTGGG GCTTTTCTGA TTATCAACCG    5640

GGGTACATAT GATTGACATG CTAGTTTTAC GATTACCGTT CATCGATTCT CTTGTTTGCT    5700

CCAGACTCTC AGGCAATGAC CTGATAGCCT TTGTAGAGAC CTCTCAAAAA TAGCTACCCT    5760

CTCCGGCATG AATTTATCAG CTAGAACGGT TGAATATCAT ATTGATGGTG ATTTGACTGT    5820

CTCCGGCCTT TCTCACCCGT TTGAATCTTT ACCTACACAT TACTCAGGCA TTGCATTTAA    5880

AATATATGAG GGTTCTAAAA ATTTTTATCC TTGCGTTGAA ATAAAGGCTT CTCCCGCAAA    5940

AGTATTACAG GGTCATAATG TTTTTGGTAC AACCGATTTA GCTTTATGCT CTGAGGCTTT    6000

ATTGCTTAAT TTTGCTAATT CTTTGCCTTG CCTGTATGAT TTATTGGATG TTGGAANTTC    6060

CTGATGCGGT ATTTTCTCCT TACGCATCTG TGCGGTATTC CACACCGCAT ATGGTGCACT    6120

CTCAGTACAA TCTGCTCTGA TGCCGCATAG TTAAGCCAGC CCCGACACCC GCCAACACCC    6180

GCTGACGCGC CCTGACGGGC TTGTCTGCTC CCGGCATCCG CTTACAGACA AGCTGTGACC    6240

GTCTCCGGGA GCTGCATGTG TCAGAGGTTT TCACCGTCAT CACCGAAACG CGCGAGACGA    6300

AAGGGCCTCG TGATACGCCT ATTTTTATAG GTTAATGTCA TGATAATAAT GGTTTCTTAG    6360

ACGTCAGGTG GCACTTTTCG GGGAAATGTG CGCGGAACCC CTATTTGTTT ATTTTTCTAA    6420

ATACATTCAA ATATGTATCC GCTCATGAGA CAATAACCCT GATAAATGCT TCAATAATAT    6480

TGAAAAAGGA AGAGTATGAG TATTCAACAT TTCCGTGTCG CCCTTATTCC CTTTTTTGCG    6540

GCATTTTGCC TTCCTGTTTT TGCTCACCCA GAAACGCTGG TGAAAGTAAA AGATGCTGAA    6600

GATCAGTTGG GTGCACGAGT GGGTTACATC GAACTGGATC TCAACAGCGG TAAGATCCTT    6660

GAGAGTTTTC GCCCCGAAGA ACGTTTTCCA ATGATGAGCA CTTTTAAAGT TCTGCTATGT    6720

GGCGCGGTAT TATCCCGTAT TGACGCCGGG CAAGAGCAAC TCGGTCGCCG CATACACTAT    6780

TCTCAGAATG ACTTGGTTGA GTACTCACCA GTCACAGAAA AGCATCTTAC GGATGGCATG    6840

ACAGTAAGAG AATTATGCAG TGCTGCCATA ACCATGAGTG ATAACACTGC GGCCAACTTA    6900

CTTCTGACAA CGATCGGAGG ACCGAAGGAG CTAACCGCTT TTTTGCACAA CATGGGGGAT    6960
```

-continued

```
CATGTAACTC GCCTTGATCG TTGGGAACCG GAGCTGAATG AAGCCATACC AAACGACGAG      7020

CGTGACACCA CGATGCCTGT AGCAATGGCA ACAACGTTGC GCAAACTATT AACTGGCGAA      7080

CTACTTACTC TAGCTTCCCG GCAACAATTA ATAGACTGGA TGGAGGCGGA TAAAGTTGCA      7140

GGACCACTTC TGCGCTCGGC CCTTCCGGCT GGCTGGTTTA TTGCTGATAA ATCTGGAGCC      7200

GGTGAGCGTG GGTCTCGCGG TATCATTGCA GCACTGGGGC CAGATGGTAA GCCCTCCCGT      7260

ATCGTAGTTA TCTACACGAC GGGGAGTCAG GCAACTATGG ATGAACGAAA TAGACAGATC      7320

GCTGAGATAG GTGCCTCACT GATTAAGCAT TGGTAACTGT CAGACCAAGT TTACTCATAT      7380

ATACTTTAGA TTGATTTAAA ACTTCATTTT TAATTTAAAA GGATCTAGGT GAAGATCCTT      7440

TTTGATAATC TCATGACCAA AATCCCTTAA CGTGAGTTTT CGTTCCACTG AGCGTCAGAC      7500

CCCGTAGAAA AGATCAAAGG ATCTTCTTGA GATCCTTTTT TTCTGCGCGT AATCTGCTGC      7560

TTGCAAACAA AAAAACCACC GCTACCAGCG GTGGTTTGTT TGCCGGATCA AGAGCTACCA      7620

ACTCTTTTTC CGAAGGTAAC TGGCTTCAGC AGAGCGCAGA TACCAAATAC TGTCCTTCTA      7680

GTGTAGCCGT AGTTAGGCCA CCACTTCAAG AACTCTGTAG CACCGCCTAC ATACCTCGCT      7740

CTGCTAATCC TGTTACCAGT GGCTGCTGCC AGTGGCGATA AGTCGTGTCT TACCGGGTTG      7800

GACTCAAGAC GATAGTTACC GGATAAGGCG CAGCGGTCGG GCTGAACGGG GGGTTCGTGC      7860

ACACAGCCCA GCTTGGAGCG AACGACCTAC ACCGAACTGA GATACCTACA GCGTGAGCTA      7920

TGAGAAAGCG CCACGCTTCC CGAAGGGAGA AAGGCGGACA GGTATCCGGT AAGCGGCAGG      7980

GTCGGAACAG GAGAGCGCAC GAGGGAGCTT CCAGGGGGAA ACGCCTGGTA TCTTTATAGT      8040

CCTGTCGGGT TTCGCCACCT CTGACTTGAG CGTCGATTTT TGTGATGCTC GTCAGGGGGG      8100

CGGAGCCTAT GGAAAAACGC CAGCAACGCG GCCTTTTTAC GGTTCCTGGC CTTTTGCTGG      8160

CCTTTTGCTC ACATGTTCTT TCCTGCGTTA TCCCCTGATT CTGTGGATAA CCGTATTACC      8220

GCCTTTGAGT GAGCTGATAC CGCTCGCCGC AGCCGAACGA CCGAGCGCAG CGAGTCAGTG      8280

AGCGAGGAAG CGGAAGAGC                                                   8299
```

(2) INFORMATION FOR SEQ ID NO:4:

(i) SEQUENCE CHARACTERISTICS:
        (A) LENGTH: 26 base pairs
        (B) TYPE: nucleic acid
        (C) STRANDEDNESS: single
        (D) TOPOLOGY: unknown (ii) MOLECULE TYPE: other nucleic acid (xi) SEQUENCE DESCRIPTION: SEQ ID NO:4:

```
GCAGGTACCG CGAGTCAGAT CTACAC                                             26
```

(2) INFORMATION FOR SEQ ID NO:5:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:5:

```
CTGTCTGAGC TAGAGCTC                                                      18
```

CHIMPANZEE ADENOVIRUS VECTORS

CROSS-REFERENCE TO RELATED APPLICATIONS

This is a continuation-in-part of U.S. provisional patent application No. 60/024,700, filed Sep. 6, 1996.

This invention was supported by the National Institute of Health Grant No. DK47757. The United States government has rights in this invention.

FIELD OF THE INVENTION

The present invention relates to the field of vectors useful in somatic gene therapy and the production and use thereof, and also to the field of vaccines.

BACKGROUND OF THE INVENTION

I. Gene Therapy

Gene therapy is an approach to treating disease, generally human disease, that is based on the modification of gene expression in cells of the patient. It has become apparent over the last decade that the single most outstanding barrier to the success of gene therapy as a strategy for treating inherited diseases, cancer, and other genetic dysfunctions is the development of useful gene transfer vehicles.

Eukaryotic viruses have been employed as vehicles for somatic gene therapy. Among the viral vectors that have been cited frequently in gene therapy research are adenoviruses. Adenoviruses are eukaryotic DNA viruses that can be modified to efficiently deliver a therapeutic or reporter transgene to a variety of cell types. Human adenoviruses are composed of a linear, approximately 36 kb double-stranded DNA genome, which is divided into 100 map units (m.u.), each of which is 360 bp in length. The DNA contains short inverted terminal repeats (ITR) at each end of the genome that are required for viral DNA replication. The gene products are organized into early (E1 through E4) and late (L1 through L5) regions, based on expression before or after the initiation of viral DNA synthesis [see, e.g., Horwitz, Virology, 2d edit., ed. B. N. Fields, Raven Press, Ltd., New York (1990)].

Recombinant adenoviruses types 2 and 5 (Ad2 and Ad5, respectively), which cause respiratory disease in humans, are currently being developed for gene therapy. Both Ad2 and Ad5 belong to a subclass of adenovirus and are not associated with human malignancies.

Recombinant adenoviruses are capable of providing extremely high levels of transgene delivery to virtually all cell types, regardless of the mitotic state. High titers ($10^{13}$ plaque forming units/ml) of recombinant virus can be easily generated in an adenovirus-transformed, human embryonic kidney cell line 293 [ATCC CRL1573]. The 293 cell line contains a functional adenovirus E1a gene which provides a transacting E1a protein. It can be cryo-stored for extended periods without appreciable losses.

The efficacy of this system in delivering a therapeutic transgene in vivo that complements a genetic imbalance has been demonstrated in animal models of various disorders [K. F. Kozarsky et al, Somatic Cell Mol. Genet., 19:449–458 (1993) ("Kozarsky et al I"); K. F. Kozarsky et al, J. Biol. Chem., 269:13695–13702 (1994) ("Kozarsky et al II"); Y. Watanabe, Atherosclerosis, 36:261–268 (1986); K. Tanzawa et al, FEBS Letters, 118(1):81–84 (1980); J. L. Golasten et al, New Engl. J. Med., 309:288–296 (1983); S. Ishibashi et al, J. Clin. Invest., 92:883–893 (1993); and S. Ishibashi et al, J. Clin. Invest., 93:1885–1893 (1994)]. Indeed, a recombinant replication defective adenovirus encoding a cDNA for the cystic fibrosis transmembrane regulator (CFTR) has been approved for use in at least two human CF clinical trials [see, e.g., J. Wilson, Nature, 365:691–692 (Oct. 21, 1993)]. The use of adenovirus vectors in the transduction of genes into hepatocytes in vivo has previously been demonstrated in rodents and rabbits [see, e.g., Kozarsky II, cited above, and S. Ishibashi et al, J. Clin. Invest., 92:883–893 (1993)]. Further support of the safety of recombinant adenoviruses for gene therapy is the extensive experience of live adenovirus vaccines in human populations.

However, many humans have pre-existing immunity to human adenoviruses as a result of previous natural exposure, and this immunity is a major obstacle to the use of recombinant human adenoviruses for gene therapy protocols.

II. Vaccines

Replication competent, recombinant adenovirus (Ad) containing a variety of inserted genes have been used as vaccine compositions with some success [see, e.g. Davis, U.S. Pat. No. 4,920,309]. Others have described the insertion of a foreign gene into a live [L. Prevac, J. Infect. Dis., 161:27–30 (1990)] and a replication-defective adenovirus for putative use as a vaccine [See, e.g. T. Ragot et al, J. Gen. Virol., 74:501–507 (1993); M. Eliot et al, J. Gen. Virol., 71:2425–2431 (1990); and S. C. Jacobs et al, J. Virol., 66:2086–2095 (1992)]. Jacobs et al, cited above, describes a recombinant E1-deleted, E3 intact, Ad containing encephalitis virus protein NS1 under the control of a heterologous cytomegalovirus (CMV) promoter. When mice were immunized with the recombinant Ad vaccines and challenged with virus, Jacobs et al obtained partial protection (at most a 75% protection) for an average survival of 15 days. Eliot et al, cited above, describe a recombinant E1-deleted, partially E3-deleted Ad with pseudorabies glycoprotein 50 inserted into the E1 deletion site under the control of a homologous Ad promoter. In rabbits and mice, after immunization and challenge, only partial protection was obtained (i.e., about one-third). Ragot et al, cited above, describe a recombinant E1-deleted, partially E3-deleted Ad with Epstein Barr virus glycoprotein gp340/220 inserted into the E1 deletion site under the control of a homologous Ad promoter. In marmosets (tamarins) after three high dose ($5 \times 10^9$ pfu, $1 \times 10^{10}$ pfu and $2 \times 10^{10}$ pfu), intramuscular immunizations and viral challenge, full protection was obtained.

For certain highly infectious diseases, there is a demand for an effective vaccine. Desirably, a vaccine should be effective at a low dosage to control the occurrence of side effects or to enable sufficient amounts of vaccine to be introduced into the animal or human.

There exists a need in the gene therapy art for the development of additional adenovirus vector constructs that do not stimulate immediate immune responses which quickly eliminate the recombinant virus and the therapeutic transgene from the patient. There also exists a need in the vaccine art for new vaccine carriers, which are safe and effective in humans and other mammals.

SUMMARY OF THE INVENTION

The present invention meets the need in the art by providing adenovirus nucleotide sequences of chimpanzee origin, a variety of novel vectors, and cell lines expressing chimpanzee adenovirus genes.

In one aspect the invention provides the nucleotide sequence of a chimpanzee C1 adenovirus. See SEQ ID NO: 1.

In another aspect the invention provides the nucleotide sequence of a chimpanzee C68 adenovirus. See SEQ ID NO: 2.

In a further aspect, the invention provides a recombinant adenovirus comprising the DNA sequence of a chimpanzee adenovirus and a selected heterologous gene operatively linked to regulatory sequences directing its expression. The recombinant virus is capable of infecting a mammalian, preferably a human, cell and capable of expressing the heterologous transgene product in the cell. In this vector, the native chimpanzee E1 gene, and/or E3 gene, and/or E4 gene may be deleted. A heterologous gene may be inserted into any of these sites of gene deletion. The heterologous transgene may encode a normal or therapeutic gene which, upon expression, replaces or modifies an inherited or acquired genetic defect. The heterologous gene may be an antigen against which a primed immune response is desired (i.e., a vaccine).

In another aspect, the invention provides a mammalian cell infected with the viral vector described above.

In still a further aspect of this invention, a novel mammalian cell line is provided which expresses a chimpanzee adenovirus gene or functional fragment thereof.

In still a further aspect, the invention provides a method for delivering a transgene into a mammalian cell comprising the step of introducing into the cell an effective amount of a recombinant virus described above.

Another aspect of this invention is a method for delivering to a mammalian patient having a disorder related to an inherited or acquired genetic defect a desired transgene. The method comprises the step of administering to the patient by an appropriate route an effective amount of an above-described recombinant chimpanzee adenovirus containing a normal or therapeutic transgene, wherein the transgene product is expressed in vivo.

Still another aspect of this invention provides a method for eliciting an immune response in a mammalian host to protect against an infective agent. The method comprises the step of administering to the host an effective amount of a recombinant chimpanzee adenovirus comprising a heterologous gene that encodes an antigen from the infecting organism against which the immune response is targeted.

Other aspects and advantages of the present invention are described further in the following detailed description of the preferred embodiments thereof.

BRIEF DESCRIPTION OF THE DRAWINGS

FIG. 1A is a diagrammatic bar graph illustrating the structure of the chimpanzee adenovirus C1 (also referred to as C-1) and the location of the adenovirus genes thereon by nucleotide position and by map unit numbers appearing under the bar graph. The locations of the late genes (L-1 through L-5) are represented by arrows below the graph with molecular weight indications above the arrows and nucleotide positions below the arrows. The location of the E2a region early TATA box and transcriptional start site was not determined. The E2a region is estimated to begin approximately at nucleotide 27,100. The position of the translation initiation codon for the E2a encoded DNA binding protein is indicated by an asterisk.

FIG. 1B is a line graph showing the correlation between map units and nucleotide (base) pairs of the sequence of C1 [SEQ ID NO: 1].

FIG. 2 is a tabular comparison of C1 and C68 predicted amino acid sequences examined for homology to previously described adenoviral protein sequences, Ad4, Ad5, Ad7, Ad12, and Ad40. Symbol "a" indicates that comparison of fragments of different size resulted in an underestimate of homology. Symbol "b" indicates a 95% identity from Ad-4 aa 1–95. A possible mistake in sequence apparently resulted in a frameshift and premature termination in this comparison. Symbol "c" indicates that Ad-5 has 2 small ORF's in this region encoding proteins of 64 and 67 residues with approximately 50% amino acid identity with, respectively, the amino and carboxy halfs of the chimp Ad homologs. Symbol "d" indicates that Ad-3 and Ad-7 fragments were not sequenced for this protein. Symbol "e" indicates that Ad-35 and Ad-4 were not sequenced for this protein. Symbol "f" indicates that the reported sequence for Ad-7 pVIII is 197aa, and the homology begins at aa30 of the chimp Ad sequences. The homology between the chimp Ad's and Ad-7 for the 197 aa region is 98% for C-1 and 90% for C-68.

FIG. 5A is a schematic drawing of plasmid pGPGK. The arrow indicates the direction of the murine PGK promoter. Restriction sites and marker genes are conventionally labeled.

FIG. 5B is a schematic drawing of plasmid pNEB-C68BamE. This plasmid contains fragments of the LacZ gene (small arrow) flanking either side of the bar indicating the C68 Ad BamE fragment. The large arrow illustrates the Amp® gene. Restriction sites and marker genes are conventionally labeled.

FIG. 5C is a schematic drawing of plasmid pGPGK-C68BamE in which the BamE fragment from pNEB-C68BamE has been cloned downstream from the PGK promoter of pGPGK.

FIG. 5D is a representation of the PCR amplification of the C68 sequence from pNEB-C68BamE, illustrating the use of primers to introduce a KpnI site just upstream of the C68 E1 region translation initiation codon at nucleotide 576 of the C68 genomic DNA and reduce the sequence distance between the promoter and C68 coding sequence. Location of the primers is indicated.

FIG. 5E is a schematic drawing of plasmid pGPGK-C68E1-ATG, in which the ATG translational start codon was moved closer to the PGK promoter.

FIG. 5F is a schematic drawing of plasmid pBS-C68BamF, in which the BamF fragment was cloned into the BamHI site of pGPGK-C68E1-ATG to generate pGPGK-C68E1 (FIG. 5G).

FIG. 5G is a schematic drawing of plasmid pGPGK-C68E1, containing the complete chimpanzee C68 Ad E1 region under the control of the murine PGK promoter.

FIG. 6A is a schematic drawing of plasmid pGPGK, a duplication of FIG. 5A for purposes of explaining construction of the C1 Ad E1 expression plasmid.

FIG. 6B illustrates the isolation of the 5' end of the C1 E1 region as a 1.9kb SnaBI-XbaI fragment.

FIG. 6C illustrates the use of primers to introduce by PCR amplification a KpnI site just upstream of the C1 E1 region translation initiation codon E1-ATG at nucleotide 577 of the C1 genomic DNA.

FIG. 6D is a schematic drawing of plasmid pGPGK-C1 mu1.3–6.6 (7.4kb).

FIG. 6E is a schematic drawing of plasmid pGPGK-C1-E1ATG.

FIG. 6F is a schematic drawing of plasmid pBS-C1BamI.

FIG. 6G is a schematic drawing of plasmid pGPGK-C1E1, containing the complete chimpanzee C1 Ad E1 region under the control of the murine PGK promoter.

FIG. 7A is a schematic drawing of plasmid pSP72-Pac with indicated restriction endonuclease enzyme cleavage sites.

FIG. 7B is a schematic drawing of plasmid pNEB-C1-BamG.

FIG. 7C is a schematic drawing of plasmid pSP-C1-mu0–1.3.

FIG. 7D is a schematic drawing of plasmid pCMV-β.

FIG. 7E is a schematic drawing of plasmid pSP-C1-mu0–1.3-CMV-B.

FIG. 7F is a schematic drawing of plasmid pGEM-3Z.

FIG. 7G is a schematic drawing of plasmid pBS-C1-BamI.

FIG. 7H is a schematic drawing of plasmid pGEM-C1-mu9–10.

FIG. 7I is a schematic drawing of plasmid pBS-C1-BamE.

FIG. 7J is a schematic drawing of plasmid pGEM-C1-mu9–17.

FIG. 7K is a schematic drawing of plasmid pC1-CMV-LacZ, illustrating C1 Ad mu 0 to 1.3, followed by the CMV promoter, a splice donor/splice acceptor sequence (SD/SA), the LacZ gene, a SV40 poly A sequence and C1 Ad mu 9–17, and additional plasmid sequence. The plasmid also contains an ori and Amp® sequence.

FIG. 8A is a schematic drawing of pSP72-Pac with indicated restriction endonuclease enzyme cleavage sites.

FIG. 8B is a schematic drawing of pNEB-C68-BamE.

FIG. 8C is a schematic drawing of pSP-C68-mu 0–1.3.

FIG. 8D is a schematic drawing of pCMV-β.

FIG. 8E is a schematic drawing of pSP-C68-mu 0–1.3-CMV-β.

FIG. 8F is a schematic drawing of pGEM-3Z.

FIG. 8G is a schematic drawing of pBS-C68-BamF.

FIG. 8H is a schematic drawing of pGEM-C68-mu9–10.

FIG. 8I is a schematic drawing of pBS-C68-BamB.

FIG. 8J is a schematic drawing of pGEM-C68-mu9–16.7.

FIG. 8K is a schematic drawing of pC68-CMV-LacZ, illustrating C68 Ad mu 0 to 1.3, followed by the CMV promoter, an SD/SA, the LacZ gene, a SV40 poly A sequence and C68 Ad mu 9–16.7, and additional plasmid sequence. The plasmid also contains an ori and an Amp® sequence.

FIG. 9A is a schematic drawing of pEGFP-1 (Clontech, Palo Alto, Calif.).

FIG. 9B is a schematic drawing of a Not-I synthetic linker (New England Biolabs).

FIG. 9C is a schematic drawing of pEGFP-Notx2.

FIG. 9D is a schematic drawing of pC1-CMV-LacZ (from FIG. 7K).

FIG. 9E is a schematic drawing of pC68-CMV-LacZ (from FIG. 8K).

FIG. 9F is a schematic drawing of pC1-CMV-GFP, in which the GFP coding region replaces the LacZ gene of pC1-CMV-LacZ.

FIG. 9G is a schematic drawing of pC68-CMV-GFP, in which the GFP coding region replaces the LacZ gene of pC68-CMV-LacZ.

FIG. 10A is a schematic drawing of pC68-CMV-GFP as discussed in FIG. 9G.

FIG. 10B is a schematic drawing of the C68 genome.

FIG. 10C is a schematic drawing of the C68-SspI-A fragment, which is 35,199 nucleotides.

FIG. 10D is a schematic drawing of the C68-CMV-GFP genome, which is formed by homologous recombination between the C68 mu 9–16.7 sequence in pC68-CMV-GFP and the homologous sequence in the C68-SspI-A fragment.

FIG. 11A is a schematic drawing of pNEB-C1-BamG.

FIG. 11B is a schematic drawing of the C1 genome.

FIG. 11C is a schematic drawing of pNEB-C1-AscI-B.

FIG. 11D is a schematic drawing of a Not-I synthetic linker (New England Biolabs).

FIG. 11E is a schematic drawing of pNEB-C1-AscI-B-NotI.

FIG. 11F is a schematic drawing of the C1 genome.

FIG. 11G is a schematic drawing of the AscI-A fragment of the C1 genome.

FIG. 11H is a schematic drawing of the C1 genome engineered to have a unique NotI site replacing the Spe-I site in the E1B 21K protein coding region.

DETAILED DESCRIPTION OF THE INVENTION

Figure 1C:
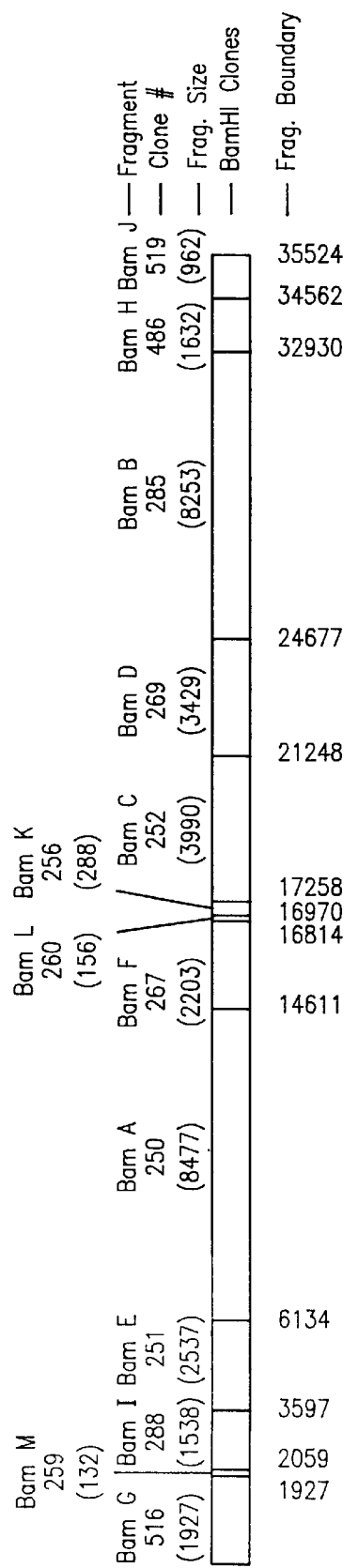
FIG. 1C is a bar graph illustrating the various Bam HI clones obtained for the C1 Ad, indicating nucleotide numbers, fragment size in nucleotides, clone numbers, and fragment boundaries in nucleotides.

The present invention provides novel adenovirus vectors and packaging cell lines to produce those vectors for use in the in vitro production of recombinant proteins or fragments or other reagents, and for use in the treatment of inherited or acquired genetic disorders and abnormalities in humans and other mammals. The present invention also provides novel vaccine compositions which comprise those vectors, the vectors comprising an inserted heterologous gene encoding an antigen from an infectious agent.

The methods of the invention involve delivering one or more selected heterologous gene(s) to a mammalian patient by administering a vector of the invention. Because the various vector constructs are derived from chimpanzee rather than from human adenoviruses, the immune system of the patient is not primed to respond immediately to the vector as a foreign antigen. A similar response would be expected where the patient was any mammal other than chimpanzee.

Use of the compositions of this invention thus permits a more stable expression of the selected transgene when administered to a non-chimpanzee, preferably human patient. Use of the compositions of this invention for vaccination permits presentation of a selected antigen for the elicitation of protective immune responses. The recombinant chimpanzee adenoviruses of this invention may also be used for producing heterologous gene products in vitro.

I. Cloning of Chimpanzee Adenovirus Sequences

Chimpanzee adenovirus, strain Bertha or C1 [ATCC Accession No. VR-20] and chimpanzee adenovirus, strain Pan-9 or CV68 [ATCC Accession No. VR-594] were obtained from the American Type Culture Collection, 12301 Parklawn Drive, Rockville, Md. For convenience, the virus CV68 is referred to throughout this specification as "C68". The viruses were originally isolated from feces [C1, Rowe et al, *Proc. Soc. Exp. Med.*, 91:260 (1956)] or mesenteric lymph node [C68, Basnight et al, *Am. J. Epidemiol.*, 94:166 (1971)] of infected chimpanzees.

Little is known about these viruses. However, limited restriction and immunological analyses have been published. For example, C1 was shown to be most similar to Subgroup B human adenoviruses, but it was not neutralized by heterologous sera, and no hemagglutination inhibition was observed [Wigand et al, *Intervirology*, 30:1 (1989)]. Restriction analysis demonstrated that C68 was most similar to human Ad4 serotype (Subgroup E), but only 1 in 16 enzymes tested did not distinguish C68 and Ad4 [Kitchingman, *Gene*, 20:205 (1982)].

Both chimpanzee adenoviruses grow well in human cells and were propagated in human embryonic kidney 293 cells. As described in detail in Examples 1 and 2 below, genomic DNA was isolated from purified virus stocks and digested with a panel of restriction enzymes and the restriction fragments cloned and sequenced. The genomic nucleotide sequence of C1 adenovirus is set out in SEQ ID NO: 1. The genomic nucleotide sequence of C68 adenovirus is set out in SEQ ID NO: 2.

Preliminary analysis of the sequence homology between C1, C68 and human adenoviruses was in agreement with the previously mentioned immunologic or restriction enzyme analysis. By reference to FIGS. 1A–1C and 3A to 3D, it is shown that the putative E1 region of C1 occurs between about nucleotides 480 and about 3958; and of C68 between about nucleotides 480 and about 3956.

Other gene regions of C1 are identified by homology of the C1 sequence of SEQ ID NO: 1 to the known sequences of human adenoviruses Ad3, Ad5 and Ad7. Similarly, other gene regions of C68 are identified by homology of the C68 sequence of SEQ ID NO: 2 to the known sequence of human adenovirus Ad4 and Ad5. The genomic regions encoding early gene functions for E2a, E2b, E3, E4, as well as the regions of C1 and C68 encoding late adenoviral gene products, are identified in Tables I and II below.

TABLE I

C1 Chimpanzee Genome

| Gene | Nucleotides | Map Units | Size (nucl./mu) |
|------|-------------|-----------|-----------------|
| E1A  | 480–1540    | 1.4–4.3   | 1060/3.0        |
| E1B  | 1566–3958   | 4.4–11.1  | 2392/6.7        |
| E2A  | 23665–22065 | 66.6–62.1 | 1600/4.5        |
| E2B  | 10379–3959  | 29.2–11.1 | 6420/18.1       |
| E3   | 27181–31375 | 76.5–88.3 | 4194/11.8       |
| E4   | 35228–32535 | 99.2–91.6 | 2693/7.6        |
| L1   | 10893–13864 | 30.7–39.0 | 2971/8.4        |
| L2   | 13925–17591 | 39.2–49.5 | 3666/10.3       |
| L3   | 17641–22083 | 49.7–62.2 | 4442/12.5       |
| L4   | 23697–27813 | 66.7–78.3 | 4116/11.6       |
| L5   | 31556–32551 | 88.8–91.6 | 995/2.8         |

TABLE II

C68 Chimpanzee Genome

| Gene | Nucleotides | Map Units | Size (nucl./mu) |
|------|-------------|-----------|-----------------|
| E1A  | 480–1521    | 1.3–4.2   | 1041/2.9        |
| E1B  | 1560–3956   | 4.3–10.8  | 2396/6.6        |
| E2A  | 23370–21787 | 64.0–59.7 | 1583/4.3        |
| E2B  | 10346–3957  | 28.3–10.8 | 6389/17.5       |
| E3   | 26806–31877 | 73.4–87.3 | 5071/13.9       |
| E4   | 36193–33486 | 99.1–91.7 | 2707/7.4        |
| L1   | 10823–13817 | 29.6–37.8 | 2994/8.2        |
| L2   | 13884–17431 | 38.0–47.7 | 3547/9.7        |
| L3   | 17480–21804 | 47.9–59.7 | 4324/11.8       |
| L4   | 23399–27439 | 64.1–75.1 | 4040/11.1       |
| L5   | 32134–33502 | 88.0–91.7 | 1368/3.7        |

Our preliminary experiments demonstrated that human antisera do not neutralize the chimpanzee adenoviruses in neutralizing antibody assays (see, e.g., International patent application PCT95/03035), thus indicating the desirability of vectors prepared from these sequences for gene therapy in humans. As further described in the examples, plasmids establishing chimpanzee adenovirus E1-expressing cell lines and recombinant E1-deleted adenoviruses expressing a transgene are prepared.

The viral sequences used in the vectors and cell lines described below may be generated by using the teachings and references contained herein, coupled with standard recombinant molecular cloning techniques known and practiced by those skilled in the art.

II. E1-Expressing Complementation Cell Lines

To generate recombinant chimpanzee adenoviruses (Ad) deleted in any of the genes described above, the function of the deleted gene region, if essential to the replication and infectivity of the virus, must be supplied to the recombinant virus by a helper virus or cell line, i.e., a complementation or packaging cell line. For example, to generate a replication-defective chimpanzee adenovirus vector, a cell line is needed which expresses the E1 gene products of the chimpanzee adenovirus. The protocol for the generation of the cell lines expressing the chimpanzee E1 gene products (Examples 3 and 4) is followed to generate a cell line which expresses any selected chimpanzee adenovirus gene.

Conventional assays were not useful in identifying the chimpanzee adenovirus E1-expressing cell line and a novel AAV augmentation assay was developed to identify the chimpanzee adenovirus E1-expressing cell line. This assay is useful to identify E1 function in cell lines made by using the E1 genes of other uncharacterized adenoviruses, e.g., from other species. That assay is described in Example 4B below.

According to this invention, the selected chimpanzee adenovirus gene, e.g., E1, is under the transcriptional control of a promoter for expression in a selected parent cell line. Inducible or constitutive promoters may be employed for this purpose. Among inducible promoters are included the sheep metallothionine promoter, inducible by zinc, or the mouse mammary tumor virus (MMTV) promoter, inducible by a glucocorticoid, particularly, dexamethasone. Other inducible promoters, such as those identified in International patent application WO95/13392, published May 18, 1995, and incorporated by reference herein may also be used in the production of packaging cell lines according to this invention. Constitutive promoters in control of the expression of the chimpanzee adenovirus gene may be employed also. The promoter used to express E1 as exemplified below is the well-known constitutive murine PGK promoter.

A parent cell is selected for the generation of a novel cell line expressing any desired C1 or C68 gene. Without limitation, such a parent cell line may be HeLa [ATCC Accession No. CCL 2], A549 [ATCC Accession No. CCL 185], KB [CCL 17], Detroit [e.g., Detroit 510, CCL 72] and WI-38 [CCL 75] cells. These cell lines are all available from the American Type Culture Collection, 12301 Parklawn Drive, Rockville, Md., USA. Other suitable parent cell lines may be obtained from other sources.

The present invention provides an exemplary cell line which contains and expresses the chimpanzee C68 or C1 Ad E1 gene, as described in detail in Examples 3 and 4 below. Briefly described, the entire chimpanzee adenovirus E1 region was cloned and, by a series of plasmid manipulations, it was placed under the control of a murine PGK promoter in a desired shuttle vector. See FIGS. 5A–5G and 6A–6G.

After the desired shuttle vector containing the adenoviral sequences (i.e., pGPGK-C68 E1 described in Example 3) was transfected into the selected parental cell line (e.g., HeLa), expression of the E1 gene was detected. Conventional G418 selection as described in Example 4A was used to generate stable clones of these E1-expressing cells. The resulting cell line is thus able to provide chimpanzee Ad E1 gene products to the replication-defective recombinant virus (see Example 5) to allow productive infection and recovery of the recombinant virus.

The E1-expressing cell lines are useful in the generation of recombinant chimpanzee adenovirus E1 deleted vectors. Cell lines constructed using essentially the same procedures that express one or more other chimpanzee adenoviral gene products are useful in the generation of recombinant chimpanzee adenovirus vectors deleted in the genes that encode those products.

Further, cell lines which express other human Ad E1 gene products are also useful in generating the chimpanzee recombinant Ads of this invention.

III. Recombinant Viral Particles as Vectors

The compositions of this invention comprise desirable viral vectors, that deliver a functional, normal or therapeutic gene to cells. Such vectors comprise chimpanzee adenovirus DNA sequence and a selected heterologous gene operatively linked to regulatory sequences which direct expression of the gene. The vector is capable of expressing the gene product in an infected mammalian cell. The vector is preferably functionally deleted in one or more viral genes. A minigene comprises the heterologous gene under the control of regulatory sequences. Optional helper viruses and/or packaging cell lines supply to the chimpanzee viral vectors any necessary products of deleted adenoviral genes.

The term "functionally deleted" means that a sufficient amount of the gene region is removed or otherwise damaged, e.g., by mutation or modification, so that the gene region is no longer capable of producing functional products of gene expression. If desired, the entire gene region may be removed.

The viral sequences, helper viruses, if needed, and recombinant viral particles, and other vector components and sequences employed in the construction of the vectors described herein are obtained as described above. The DNA sequences of the two chimpanzee adenoviruses are employed to construct vectors and cell lines useful in the preparation of such vectors.

Modifications of the nucleic acid sequences forming the vectors of this invention, including sequence deletions, insertions, and other mutations may be generated using standard molecular biological techniques and are within the scope of this invention.

A. The "Minigene"

The methods employed for the selection of the transgene, the cloning and construction of the "minigene" and its insertion into the viral vector are within the skill in the art given the teachings provided herein. By "minigene" is meant the combination of a selected heterologous gene and the other regulatory elements necessary to transcribe the gene and express the gene product in a host cell. The gene is operatively linked to regulatory components in a manner which permits its transcription. Such components include conventional regulatory elements necessary to drive expression of the transgene in a cell transfected with the viral vector. Thus the minigene also contains a selected promoter which is linked to the transgene and located, with other regulatory elements, within the selected viral sequences of the recombinant vector.

Selection of the promoter is a routine matter and is not a limitation of this invention. Useful promoters may be constitutive promoters or regulated (inducible) promoters, which will enable control of the amount of the transgene to be expressed. For example, a desirable promoter is that of the cytomegalovirus immediate early promoter/enhancer [see, e.g., Boshart et al, Cell, 41:521–530 (1985)]. Another desirable promoter includes the Rous sarcoma virus LTR promoter/enhancer. Still another promoter/enhancer sequence is the chicken cytoplasmic β-actin promoter [T. A. Kost et al, Nucl. Acids Res., 11(23):8287 (1983)]. Other suitable or desirable promoters may be selected by one of skill in the art.

The minigene may also desirably contain nucleic acid sequences heterologous to the viral vector sequences including sequences providing signals required for efficient polyadenylation of the transcript (poly-A or pA) and introns with functional splice donor and acceptor sites. A common poly-A sequence which is employed in the exemplary vectors of this invention is that derived from the papovavirus SV-40. The poly-A sequence generally is inserted in the minigene following the transgene sequences and before the viral vector sequences. A common intron sequence is also derived from SV-40, and is referred to as the SV-40 T intron sequence. A minigene of the present invention may also contain such an intron, desirably located between the promoter/enhancer sequence and the transgene. Selection of these and other common vector elements are conventional [see, e.g., Sambrook et al, "Molecular Cloning. A Laboratory Manual.", 2d edit., Cold Spring Harbor Laboratory, New York (1989) and references cited therein] and many such sequences are available from commercial and industrial sources as well as from Genbank.

As above stated, the minigene is located in the site of any selected deletion in the viral vector, such as the site of the E1 gene region deletion or E3 gene region deletion, among others which may be selected.

B. Construction of The Viral Plasmid Vector

The chimpanzee adenovirus vectors useful in this invention include recombinant, defective adenoviruses, that is, chimpanzee adenovirus sequences functionally deleted in the E1a or E1b genes, and optionally bearing other mutations, e.g., temperature-sensitive mutations or deletions in other genes. It is anticipated that these chimpanzee sequences are also useful in forming hybrid vectors from other adenovirus and/or adeno-associated virus sequences. Homologous adenovirus vectors prepared from human adenoviruses are described in the published literature [see, for example, Kozarsky I and II, cited above, and references cited therein, U.S. Pat. No. 5,240,846].

In the construction of useful chimpanzee adenovirus vectors for delivery of a gene to the human (or other mammalian) cell, a range of adenovirus nucleic acid sequences can be employed in the vectors. A vector comprising minimal chimpanzee adenovirus sequences may be used in conjunction with a helper virus to produce an infectious recombinant virus particle. The helper virus provides essential gene products required for viral infectivity and propagation of the minimal chimpanzee adenoviral vector. When only one or more selected deletions of chimpanzee adenovirus genes are made in an otherwise functional viral vector, the deleted gene products can be supplied in the viral vector production process by propagating the virus in a selected packaging cell line that provides the deleted gene functions in trans.

1. Recombinant Minimal Adenovirus

A minimal chimpanzee Ad virus is a viral particle containing only the adenovirus cis-elements necessary for replication and virion encapsidation, which cis-elements flank the heterologous gene. That is, the vector contains only the cis-acting 5' and 3' inverted terminal repeat (ITR) sequences of the adenoviruses of this invention (which function as origins of replication) and the native 5' packaging/enhancer domains (that contain sequences necessary for packaging linear Ad genomes and enhancer elements for the E1 promoter). See, for example, the techniques described for preparation of a "minimal" human Ad vector in International Patent Application WO96/13597, published May 9, 1996, and incorporated herein by reference.

2. Other Defective Adenoviruses

Recombinant, replication-deficient adenoviruses of this invention may also contain more than the minimal chimpanzee adenovirus sequences defined above. These other Ad vectors can be characterized by deletions of various portions of gene regions of the virus, and infectious virus particles formed by the optional use of helper viruses and/or packaging cell lines, as described herein.

As one example, suitable vectors may be formed by deleting all or a sufficient portion of the adenoviral immediate early gene E1a and delayed early gene E1b, so as to eliminate their normal biological functions. Replication-defective E1-deleted viruses are capable of replicating and producing infectious virus when grown on a chimpanzee adenovirus-transformed, complementation cell line containing functional adenovirus E1a and E1b genes which provide the corresponding gene products in trans. Based on the homologies to known adenovirus sequences, it is anticipated that, as is true for the human recombinant E1-deleted adenoviruses of the art, the resulting recombinant chimpanzee adenovirus is capable of infecting many cell types and can express a transgene, but cannot replicate in most cells that do not carry the chimpanzee E1 region DNA unless the cell is infected at a very high multiplicity of infection.

As another example, all or a portion of the adenovirus delayed early gene E3 may be eliminated from the chimpanzee adenovirus sequence which forms a part of the recombinant virus. The function of chimpanzee E3 is believed to be irrelevant to the function and production of the recombinant virus particle.

Chimpanzee adenovirus vectors may also be constructed having a deletion of the E4 gene. Still another vector of this invention contains a deletion in the delayed early gene E2a.

Deletions may also be made in any of the late genes L1 through L5 of the chimpanzee adenovirus genome. Similarly, deletions in the intermediate genes IX and IVa$_2$ may be useful for some purposes. Other deletions may be made in the other structural or non-structural adenovirus genes.

The above discussed deletions may be used individually, i.e., an adenovirus sequence for use in the present invention may contain deletions of E1 only. Alternatively, deletions of entire genes or portions thereof effective to destroy their biological activity may be used in any combination. For example, in one exemplary vector, the adenovirus sequence may have deletions of the E1 genes and the E4 gene, or of the E1, E2a and E3 genes, or of the E1 and E3 genes, or of E1, E2a and E4 genes, with or without deletion of E3, and so on. As discussed above, such deletions may be used in combination with other mutations, such as temperature-sensitive mutations, to achieve a desired result.

The minigene containing the transgene may be inserted optionally into any deleted region of the chimpanzee Ad virus. Alternatively, the minigene may be inserted into an existing gene region to disrupt the function of that region, if desired.

The construction of exemplary E1-deleted chimpanzee Ad virus vectors is described in detail in Example 5 below. Desirably, such a vector contains chimpanzee adenovirus sequences Ad m.u. 0–1.3, followed by a minigene containing the transgene of interest (e.g., a therapeutic gene for the correction of a genetic defect in a patient or a marker gene to visualize infected cells) and the sequence Ad m.u. 9 to 100 of C1 or C68. These recombinant adenoviruses are functionally deleted of E1a and E1b.

C. Production of the Recombinant Viral Particle

1. Helper Viruses

Depending upon the chimpanzee adenovirus gene content of the viral vectors employed to carry the minigene, a helper adenovirus or non-replicating virus fragment may be necessary to provide sufficient chimpanzee adenovirus gene sequences necessary to produce an infective recombinant viral particle containing the minigene.

Useful helper viruses contain selected adenovirus gene sequences not present in the adenovirus vector construct and/or not expressed by the packaging cell line in which the vector is transfected. A preferred helper virus is desirably replication-defective and contains a variety of adenovirus genes in addition to the sequences described above. The helper virus is desirably used in combination with the E1-expressing cell lines described herein.

Most preferably for C68, the "helper" virus is a fragment formed by clipping the C terminal end of the C68 genome with SspI, which removes about 1300 bp from the left end of the virus. This clipped virus is then co-transfected into the E1-expressing cell line with the plasmid DNA, thereby forming the recombinant virus by homologous recombination with the C68 sequences in the plasmid.

Because there is no similarly unique restriction site in the 5' end of C1, to create a recombinant virus, the SpeI site at position 1733 is replaced with a unique Not I site, generating the modified C1 NotI genome of about 35,526 bp. See, e.g., FIGS. 12A–12F.

Helper viruses may also be formed into poly-cation conjugates as described in Wu et al, *J. Biol. Chem.*, 264:16985–16987 (1989); K. J. Fisher and J. M. Wilson, *Biochem. J.*, 299:49 (Apr. 1, 1994). Helper virus may optionally contain a second reporter minigene. A number of such reporter genes are known to the art. The presence of a reporter gene on the helper virus which is different from the transgene on the adenovirus vector allows both the Ad vector and the helper virus to be independently monitored. This second reporter is used to enable separation between the resulting recombinant virus and the helper virus upon purification.

2. Assembly of Viral Particle and Infection of a Cell Line

Assembly of the selected DNA sequences of the adenovirus, and the transgene and other vector elements into various intermediate plasmids and shuttle vectors, and the use of the plasmids and vectors to produce a recombinant viral particle are all achieved using conventional techniques. Such techniques include conventional cloning techniques of cDNA such as those described in texts [Sambrook et al, cited above], use of overlapping oligonucleotide sequences of the adenovirus genomes, polymerase chain reaction, and any suitable method which provides the desired nucleotide sequence. Standard transfection and co-transfection techniques are employed, e.g., $CaPO_4$ precipitation techniques. Other conventional methods employed include homologous recombination of the viral genomes, plaquing of viruses in agar overlay, methods of measuring signal generation, and the like.

For example, following the construction and assembly of the desired minigene-containing viral vector, the vector is transfected in vitro in the presence of a helper virus into the packaging cell line. Homologous recombination occurs between the helper and the vector sequences, which permits the adenovirus-transgene sequences in the vector to be replicated and packaged into virion capsids, resulting in the recombinant viral vector particles. The current method for producing such virus particles is transfection-based. However, the invention is not limited to such methods.

The resulting recombinant chimpanzee adenoviruses are useful in transferring a selected transgene to a selected cell. In in vivo experiments with the recombinant virus grown in the packaging cell lines, the E1-deleted recombinant chimpanzee adenovirus demonstrates utility in transferring a transgene to a non-chimpanzee, preferably a human, cell.

IV. Use of the Recombinant Virus Vectors

The resulting recombinant chimpanzee adenovirus containing the minigene (produced by cooperation of the adenovirus vector and helper virus or adenoviral vector and packaging cell line, as described above) thus provides an efficient gene transfer vehicle which can deliver the transgene to a human patient in vivo or ex vivo.

The above-described recombinant vectors are administered to humans according to published methods for gene therapy. A chimpanzee viral vector bearing the selected transgene may be administered to a patient, preferably suspended in a biologically compatible solution or pharmaceutically acceptable delivery vehicle. A suitable vehicle includes sterile saline. Other aqueous and non-aqueous isotonic sterile injection solutions and aqueous and non-aqueous sterile suspensions known to be pharmaceutically acceptable carriers and well known to those of skill in the art may be employed for this purpose.

The chimpanzee adenoviral vectors are administered in sufficient amounts to transduce the human cells and to provide sufficient levels of gene transfer and expression to provide a therapeutic benefit without undue adverse or with medically acceptable physiological effects, which can be determined by those skilled in the medical arts. Conventional and pharmaceutically acceptable routes of administration include, but are not limited to, direct delivery to the liver, intranasal, intravenous, intramuscular, subcutaneous, intradermal, oral and other parental routes of administration. Routes of administration may be combined, if desired.

Dosages of the viral vector will depend primarily on factors such as the condition being treated, the age, weight and health of the patient, and may thus vary among patients. For example, a therapeutically effective human dosage of the viral vector is generally in the range of from about 20 to about 100 ml of saline solution containing concentrations of from about $1 \times 10^9$ to $1 \times 10^{11}$ pfu/ml virus vector. A preferred human dosage is estimated to be about 50 ml saline solution at $2 \times 10^{10}$ pfu/ml. The dosage will be adjusted to balance the therapeutic benefit against any side effects and such dosages may vary depending upon the therapeutic application for which the recombinant vector is employed. The levels of expression of the transgene can be monitored to determine the frequency of dosage administration.

An optional method step involves the co-administration to the patient, either concurrently with, or before or after administration of the viral vector, of a suitable amount of a short acting immune modulator. The selected immune modulator is defined herein as an agent capable of inhibiting the formation of neutralizing antibodies directed against the recombinant vector of this invention or capable of inhibiting cytolytic T lymphocyte (CTL) elimination of the vector. The immune modulator may interfere with the interactions between the T helper subsets ($T_{H1}$ or $T_{H2}$) and B cells to inhibit neutralizing antibody formation. Alternatively, the immune modulator may inhibit the interaction between $T_{H1}$ cells and CTLs to reduce the occurrence of CTL elimination of the vector.

A variety of useful immune modulators and dosages for use of same are disclosed, for example, in Yang et al., *J. Virol.*, 70(9) (Sept., 1996); International Patent Application No. WO96/12406, published May 2, 1996; and International Patent Application No.PCT/US96/03035, all incorporated herein by reference.

The recombinant chimpanzee adenoviruses may also be employed as vaccines or immune response-inducing compositions. The present invention provides a recombinant replication-defective chimpanzee Ad which can contain in any of its adenovirus sequence deletions a gene encoding a desired antigen. The chimpanzee adenovirus is likely to be better suited for use as a live recombinant virus vaccine in different animal species compared to an adenovirus of human origin. The recombinant adenoviruses can be used as prophylactic or therapeutic vaccines against any pathogen for which the antigen(s) crucial for induction of an immune response and able to limit the spread of the pathogen has been identified and for which the cDNA is available.

Because the recombinant chimpanzee adenoviruses described above are deleted in the E1 sequences, the adenoviruses are replication defective and thus highly unlikely to spread within a host or among individuals. The recombinant virus lacks oncogenic potential because the E1 gene, that can function as an oncogene in some adenovirus strains, has been deleted.

With respect to efficacy, the recombinant, replication-defective adenoviruses of this invention are expected to be highly efficacious at inducing cytolytic T cells and antibodies to the inserted heterologous antigenic protein expressed by the virus. This has been demonstrated with a recombinant, replication-defective human Ad containing a sequence encoding the rabies virus glycoprotein as the heterologous gene. See, e.g., Z. Q. Xiang et al., Virol., 219:220–227 (1996).

As described above and in the examples below, in the site of the E1 deletion of either of the two chimpanzee adenoviruses of this invention, and under control of a promoter heterologous to adenovirus, a sequence encoding a protein heterologous to the adenovirus is inserted using techniques known to those of skill in the art. The heterologous nucleic acid encodes a protein which is desirably capable of inducing an immune response to a pathogen when administered to an immunocompetent host. Such a protein may be a protein from, among others, rabies virus, human papilloma virus, human immunodeficiency virus (HIV), and respiratory syncytial virus (RSV), as well as antigens associated with diseases of other mammals.

It is also anticipated that the vaccine method of the present invention may be employed with a tumor-associated protein specific for a selected malignancy. These tumor antigens include viral oncogenes, such as E6 and E7 of human papilloma virus, or cellular oncogenes such as mutated ras or p53. Particularly, where the condition is human immunodeficiency virus (HIV) infection, the protein is preferably HIV glycoprotein 120 for which sequences are available from GenBank. Where the condition is human papilloma virus infection, the protein is selected from the group consisting of E6, E7 and/or L1 [Seedorf, K. et al, Virol., 145:181–185 (1985)]. Where the condition is respiratory syncytial virus infection, the protein is selected from the group consisting of the glyco- (G) protein and the fusion (F) protein, for which sequences are available from GenBank. In addition to these proteins, other virus-associated proteins, including proteins which are antigens for disease-causing agents of other mammals, e.g., domestic animals, horses, farm animals, etc., are readily available to those of skill in the art. Selection of the heterologous proteins is not a limiting factor in the design of vaccine compositions of this invention.

A recombinant replication-defective chimpanzee adenoviral vector bearing a gene encoding an immunogenic protein may be administered to a human or other mammalian patient, preferably suspended in a biologically compatible solution or pharmaceutically acceptable delivery vehicle. A suitable vehicle is sterile saline. Other aqueous and non-aqueous isotonic sterile injection solutions and aqueous and non-aqueous sterile suspensions known to be pharmaceutically acceptable carriers and well known to those of skill in the art may be employed for this purpose.

Optionally, a vaccinal composition of the invention may be formulated to contain other components, including, e.g. adjuvants, stabilizers, pH adjusters, preservatives and the like. Such components are well known to those of skill in the vaccine art.

The recombinant, replication defective adenoviruses are administered in a "pharmaceutically effective amount", that is, an amount of recombinant adenovirus that is effective in a route of administration to transfect the desired cells and provide sufficient levels of expression of the selected gene to provide a vaccinal benefit, i.e., some measurable level of protective immunity.

Conventional and pharmaceutically acceptable routes of administration include, but are not limited to, intranasal, intramuscular, intratracheal, subcutaneous, intradermal, rectal, oral and other parental routes of administration. Routes of administration may be combined, if desired, or adjusted depending upon the immunogen or the disease. For example, in prophylaxis of rabies, the subcutaneous, intratracheal and intranasal routes are preferred. The route of administration primarily will depend on the nature of the disease being treated.

Doses or effective amounts of the recombinant replication-defective Ad virus will depend primarily on factors such as the condition, the selected gene, the age, weight and health of the animal, and may thus vary among animals. For example, a prophylactically effective amount or dose of the Ad vaccine is generally in the range of from about 100 μl to about 10 ml of saline solution containing concentrations of from about $1 \times 10^4$ to $1 \times 10^7$ plaque forming units (pfu) virus/ml. A preferred dose is from about 1 to about 10 ml saline solution at the above concentrations. The levels of immunity of the selected gene can be monitored to determine the need, if any, for boosters. Following an assessment of antibody titers in the serum, optional booster immunizations may be desired.

An additional use of the recombinant adenovirus vectors described herein resides in their use as expression vectors for the production of the products encoded by the heterologous genes. For example, the recombinant adenoviruses containing a gene inserted into the location of an E1 deletion may be transfected into an E1-expressing cell line as described above. The transfected cells are then cultured in the conventional manner, allowing the recombinant adenovirus to express the gene product from the promoter. The gene product may then be recovered from the culture medium by known conventional methods of protein isolation and recovery from culture.

The following examples illustrate the cloning of the chimpanzee adenoviruses and the construction and testing of the chimpanzee Ad E1 expressing cell line and the construction of exemplary recombinant adenovirus vectors of the present invention. These examples are illustrative only, and do not limit the scope of the present invention.

EXAMPLE 1

Virus Stocks and Propagation

The C1 [ATCC Accession No. VR-20] and C68 [ATCC Accession No. 594] virus stocks were obtained and propagated in 293 cells [ATCC CRL1573] cultured in Dulbecco's Modified Eagles Medium (DMEM; Sigma, St. Louis, Mo.) supplemented with 10% fetal calf serum (FCS) [Sigma or Hyclone, Logan, Utah] and 1% Penicillin-Streptomycin (Sigma). Infection of 293 cells was carried out in DMEM supplemented with 2% FCS for the first 24 hours, after which FCS was added to bring the final concentration to 10%. Infected cells were harvested when 100% of the cells exhibited virus-induced cytopathic effect (CPE), collected, and concentrated by centrifugation. Cell pellets were resuspended in 10 mM Tris (pH 8.0), and lysed by 3 cycles of freezing and thawing.

Virus preparations were obtained following two ultra centrifugation steps on cesium chloride density gradients and stocks of virus were diluted to $1 \times 10^{12}$ particles/ml in 10 mM Tris/100 mM NaCl/50% glycerol and stored at −70° C.

EXAMPLE 2

Cloning and Sequencing of Viral Genomic DNA

Genomic DNA was isolated from the purified virus preparations of Example 1, following standard methods [see, e.g., M. S. Horwitz et al, "Adenoviridae and Their Replication", *Virology,* second edition, pp. 1712, ed. B. N. Fields et al, Raven Press Ltd., New York (1990); B. J. Carter, in "Handbook of Parvoviruses", ed. P. Tijsser, CRC Press, pp. 155–168 (1990)] and digested with a panel of 16 restriction enzymes following the manufacturers' recommendations. Enzymes that cut the DNA 10–15 times were utilized for cloning of the viral DNA into pBluescript SK+. Except as noted, all restriction and modifying enzymes used in this and the following examples were obtained from Boehringer Mannheim, Indianapolis, Ind..

Manipulation of the genomic DNA to remove the covalently attached terminal protein was performed [Berkner and Sharp, *Nucleic Acids Res.,* 11: 6003 (1983)]. Taking advantage of the absence of Pac-I restriction sites, synthetic PacI linkers (New England Biolabs, Beverly, Mass.) were ligated onto the ends of the genomic DNA. Genomic DNA was digested with BamHI, PstI, SalI or XbaI and the restriction fragments (all but the genomic terminal fragments) were cloned into pBluescript SK+ (Stratagene, La Jolla, Calif.). Fragments containing the left and right genomic termini were cloned into pNEB-193 (New England Biolabs, Beverly, Mass.) as Pac-I/BamHI or Pac-I/Pst-I fragments.

Figure 3A:
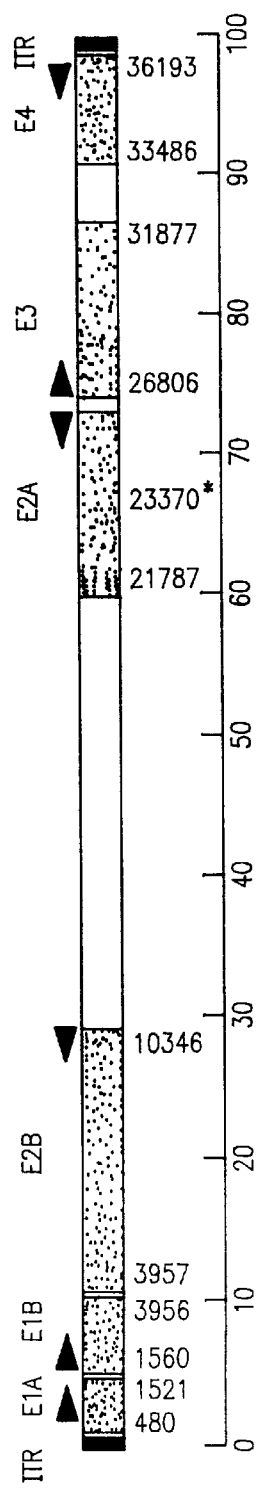
FIG. 3A is a diagrammatic bar graph illustrating the structure of the chimpanzee adenovirus C68 and the location of the adenovirus genes thereon by nucleotide position and by map unit numbers appearing under the bar graph. The locations of the late genes are represented as described for FIG. 1A. The location of the E2a region early TATA box and transcriptional start site was not determined. The E2a region is estimated to begin approximately at nucleotide 26,800. The position of the translation initiation codon for the E2a encoded DNA binding protein is indicated by an asterisk. Although the entire genome of C68 has been cloned, certain of the fragments in FIG. 3 have been individually cloned (white bars) or not cloned (shaded bars).
Figure 3B:
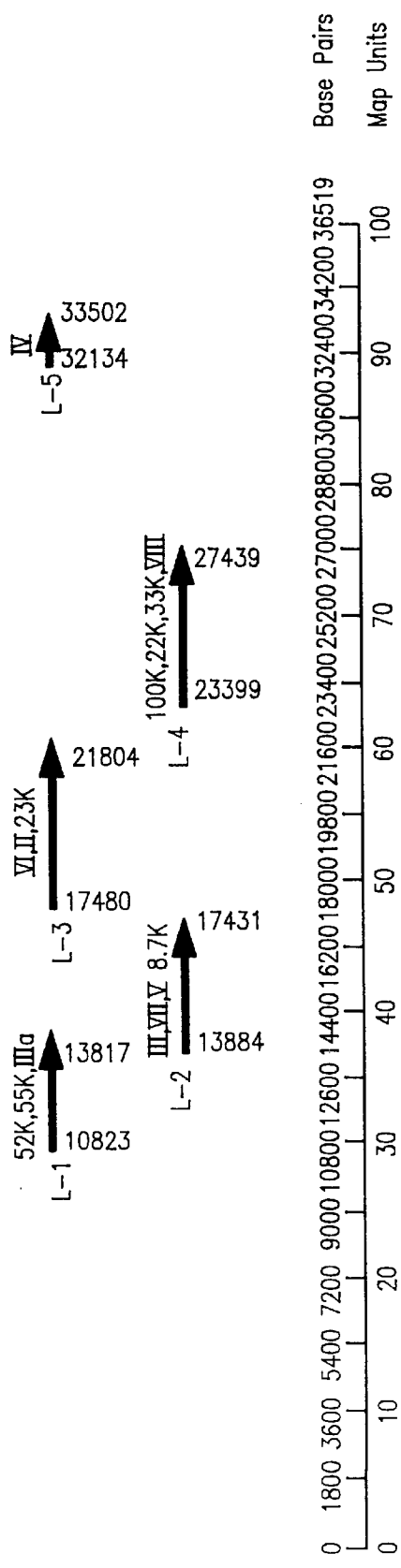
FIG. 3B is a line graph showing the correlation between map units and nucleotide (base) pairs of the sequence of C68 [SEQ ID NO: 2]. White and shaded boxes are defined as in FIG. 3A.
Figure 3C:
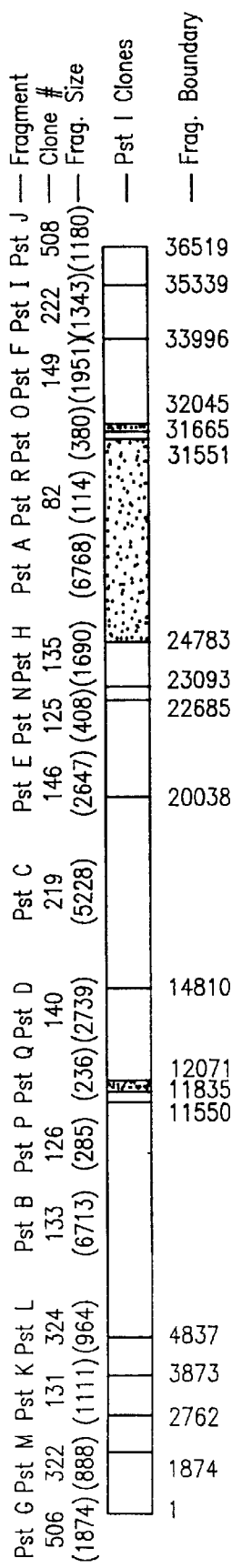
FIG. 3C is a bar graph illustrating the various Pst fragments obtained for the C68 Ad, indicating nucleotide numbers, fragment sizes in nucleotides, clone numbers and fragment boundaries in nucleotides. White and shaded boxes are defined as in FIG. 3A.
Figures 3D, 3E:
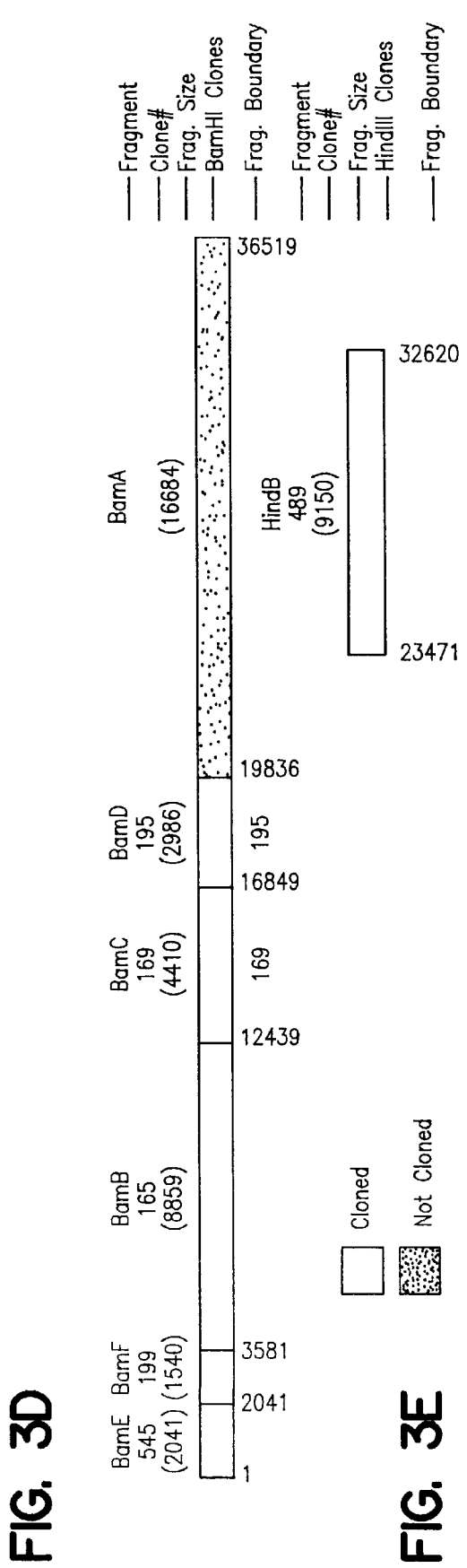
FIG. 3D is a bar diagram illustrating Bam HI fragments of the C68 genome indicating nucleotide numbers, fragment size in nucleotides, clone numbers, and fragment boundaries in nucleotides. White and shaded boxes are defined as in FIG. 3A.
FIG. 3E is a bar diagram illustrating the HindIII-B fragment and its nucleotide boundaries and size. White and shaded boxes are defined as in FIG. 3A.

The clones generated for C1 and C68 are illustrated in FIGS. 1C and 3C, respectively. The cloned fragments are described in Table III(C1) [nucleotide sequence numbers correspond with SEQ ID NO: 1] and Table IVA–IVB (C68) [nucleotide sequence numbers correspond with SEQ ID NO: 2].

TABLE III

| Construct Name | Insert Size | Clone # | Sequence |
| --- | --- | --- | --- |
| pBS: C1-Bam-A | 8477 | 250, 260, 281 | 6135–14611 |
| pBS: C1-Bam-B | 8253 | 285 | 24678–32930 |
| pBS: C1-Bam-C | 3990 | 252 | 17259–21248 |
| PBS: C1-Bam-D | 3429 | 263, 269, 275 | 21250–24677 |
| pBS: C1-Bam-E | 2537 | 251 | 3598–6134 |
| pBS: C1-Bam-F | 2203 | 267, 270, 279 | 14612–16814 |
| pNEB: C1-Bam-G | 1927 | 516 | 1–1927 left end |
| pBS: C1-Bam-H | 1632 | 486, 487 | 32931–34562 |
| pBS: C1-Bam-I | 1538 | 288–293, 483, 485 | 2060–3597 |
| pNEB: C1-Bam-J | 962 | 519 | 34563–35524 right end |
| pBS: C1-Bam-K | 288 | 256, 295, 296, 298 | 16971–17258 |
| pBS: C1-Bam-L | 156 | 260 | 16815–16970 |
| pBS: C1-Bam-M | 132 | 259, 261, 262 | 1928–2059 |
| pBS: C1-Bam-A/Pst |  | 423–428 | subclone of 250 |
| pBS: C1-Bam-B/HindIII |  | 429–434 | subclone of 285 |
| pNEB: C-1AscB | 7937 | 955 | 1–7937 left end |

TABLE IVA

| Construct Name | Size | Clone # | Sequence |
| --- | --- | --- | --- |
| pBS: C68-Pst-A | 6768 |  | 24790–31554 |
| pBS: C68-Pst-B | 6713 | 133, 141, 213–217, 303–305 | 4838–11550 |
| pBS: C68-Pst-C | 5228 | 219–221 | 14811–20038 |

TABLE IVA-continued

| Construct Name | Size | Clone # | Sequence |
| --- | --- | --- | --- |
| pBS: C68-Pst-D | 2739 | 78, 140 | 12072–14810 |
| pBS: C68-Pst-E | 2647 | 127, 129, 146, 151 | 20039–22685 |
| pBS: C68-Pst-F | 1951 | 138, 149 | 32046–33996 |
| pNEB: C68-Pst-G | 1874 | 502, 505, 506 | 1–1874 left end |
| pBS: C68-Pst-H | 1690 | 128, 135, 145, 152 | 23094–24783 |
| pBS: C68-Pst-I | 1343 | 222–224 | 33997–35339 |
| pNEB: C68-Pst-J | 1180 | 508 | 35340–36519 right end |
| pBS: C68-Pst-K | 1111 | 87, 131, 132, 136, 225–230 | 2763–3873 |
| pBS: C68-Pst-L | 964 | 320, 321, 323, 324 | 3874–4837 |
| pBS: C68-Pst-M | 888 | 319, 322 | 1875–2762 |
| pBS: C68-Pst-N | 408 | 84, 125, 130 | 22686–23093 |
| pBS: C68-Pst-O | 380 |  | 31666–32045 |
| pBS: C68-Pst-P | 285 | 79, 126 | 11551–11835 |
| pBS: C68-Pst-Q | 236 |  | 11836–12071 |
| pBS: C68-Pst-R | 114 | 82 | 31552–31665 |

TABLE IVB

|  | Size | Clone # | Sequence |
| --- | --- | --- | --- |
| BamHI Fragments |  |  |  |
| pBS: C68-Bam-A | 16684 |  | 19836–36519 right end |
| pBS: C68-Bam-B | 8858 | 95, 99, 101–103, 119–121, 165, 166, 169, 171 | 3582–12439 |
| pBS: C68-Bam-C | 4410 | 104, 106, 167, 179, 171 | 12440–16849 |
| pBS: C68-Bam-D | 2986 | 195–197 | 16850–19835 |
| pNEB: C68-Bam-E | 2041 | 537, 545 | 1–2041 left end |
| pBS: C68-Bam-F | 1540 | 198–200 | 2042–3581 |
| HindIII Fragments |  |  |  |
| pBR: C-68-Hind-B | 9150 | 489, 419, 492 | 23471–32620 |

Cloned restriction fragments were ordered in the genome by comparison to known adenoviral sequences. The nucleotide sequence of both viruses was determined [Commonwealth Biotechnologies Incorporated, Richmond, Va.]. The nucleotide sequence of the top strand of C1 DNA is reported in SEQ ID NO: 1. The nucleotide sequence of the top strand of C68 DNA is reported in SEQ ID NO: 2. Restriction maps were generated using a number of enzymes and compared to data obtained from restricted genomic DNA following electrophoreses on agarose gels.

Regulatory and coding regions in the viral DNA sequences were identified by homology to known adenoviral sequences using the Mac Vector program (Oxford Molecular Group) and a MacIntosh Quadra 610 computer (Apple Computer, Cupertino, Calif.). See Tables I and II. Open reading frames were translated and the predicted amino acid sequences examined for homology to previously described adenoviral protein sequences, Ad4, Ad5, Ad7, Ad12, and Ad40. See FIG. 2 below.

The C1 E1 coding region is defined as the sequences between the E1A translation initiation site at nucleotide 576 of SEQ ID NO: 1 and the E1B translation termination signal at nucleotide 3507 of SEQ ID NO: 1. The corresponding sequences in the C68 genome are located at nucleotides 577 and 3510 of SEQ ID NO: 2. Other open reading frames and regulatory elements of the viruses are being examined for homology with other adenoviral sequences.

Our preliminary experiments have demonstrated that human antisera do not neutralize the chimpanzee adenoviruses in neutralizing antibody assays.

EXAMPLE 3

Generation of Plasmid Vectors Expressing the C1 and C68 E1 Genes

Plasmid vectors were constructed which encode the C1 and C68 E1 region genes, and these plasmids were used to generate stable cell lines expressing viral E1 proteins.

A. pGPGK-C68 E1 pGPGK (gift of Gaung Ping Gao, University of Pennsylvania, Philadelphia, Pa.) is illustrated in FIG. 5A. pGPGK is a 5.5 kb plasmid containing the known murine PGK promoter (indicated by the arrow on FIG. 5A), followed by a multiple cloning site, a growth hormone polyA sequence, an SV40 ori, a neomycin resistance gene, an SV40 polyA sequence and an ampicillin resistance gene. The remainder of the plasmid is additional plasmid sequence.

As shown in FIG. 5B, the 5' end of the C-68 E1 region was derived from clone 245 which contains a defective version of the C-68 BamHI-E fragment (2042 base pairs) in pNEB-193, i.e., clone 245 was shown to lack approximately the first 30 base pairs of the C-68 genomic sequence, a region not included in the final product of this construction scheme, pGPGK-C68 E1. This plasmid pNEB-C68BamE was digested with BamHI and HindIII and the 2.1kb fragment was ligated with similarly digested pGPGK DNA. The resulting plasmid is designated pGPGK-C68 BamE, illustrated in FIG. 5C.

PCR primers SF-34 (GCAGGTACCGCGAGTCAGATCTACAC) [SEQ ID NO: 4] and SF-35 (CTGTCTGAGCTAGAGCTC) [SEQ ID NO: 5] were designed to introduce a KpnI restriction site 31 base pairs upstream of the E1A translation initiation site (nucleotide 577 of SEQ ID NO: 2). Using clone 245 as template, a 293 bp PCR product was obtained using reagents from Perkin Elmer (Foster City, Calif.) under the following conditions: 94=BOC×5 minutes; 25 cycles of 94=BOC×1 minute; 54=BOC×1 minute; 72=BOC×2 minutes; and a final extension cycle of 72=BOC×7 minutes. The PCR product was purified and is indicated by the hatched bar in FIG. 5D.

The PCR product was digested with KpnI and NheI, yielding a 253 bp fragment, which was purified and ligated with similarly digested pGPGK-C68 BamE (FIG. 5C) DNA to yield pGPGK-C68 E1-ATG (FIG. 5E).

The region derived from the PCR step was sequenced for several isolates and the adenovirus insert in pGPGK-C68E1-ATG was shown to match the expected sequence derived from C-68 genomic DNA. pGPGK-C68 E1-ATG (FIG. 5E) was digested with BamHI and the linearized plasmid treated with calf intestinal phosphatase. The purified/phosphatased backbone was ligated with the 1544 bp C-68 BamF fragment isolated from pBS-C68 BamF (FIG. 5F) to yield the final plasmid, designated pGPGK-C68 E1 (FIG. 5G).

The C-68 derived sequence in plasmid pGPGK-C68 E1 ends at the BamHI site corresponding to nucleotide 3581 of SEQ ID NO: 2 in the C-68 genomic sequence, which is 80 bp downstream of the end of the E1B coding region. This expression plasmid contains from about nucleotide 546 to nucleotide 3581 of SEQ ID NO: 2 which encodes E1a and E1b of chimpanzee Ad C68 under the control of the PGK promoter.

B. pGPGK-C1 E1

The C1 Ad E1 expression plasmid was constructed in a manner similar to that described above for the C68 E1 expression plasmid. Refer to FIGS. 6A through 6G.

The 5' end of the C-1 E1 region is isolated as a 1.9kb SnaBI-XbaI fragment (FIG. 6B) and is cloned into pGPGK (FIG. 6A) digested with XbaI and EcoRV. The resulting pGPGK-C1 (map units 1.3–6.6) (FIG. 6D) is used as the template for PCR. Primers are designed to introduce a KpnI site just upstream of the C1 E1 region translation initiation codon (E1-ATG) at nucleotide 578 of the C1 genomic DNA. (See FIG. 6C).

The PCR product is double digested with KpnI and KspI and ligated with similarly digested pGPGK-C1 (m.u. 1.3–6.6) to yield pGPGK-C1 E1-ATG. Partial digestion of pGPGK-C1 E1-ATG (FIG. 6E) with BamHI and isolation of the full length linear DNA, followed by XbaI digestion and isolation of the full length band, followed by ligation with similarly digested pBS-C1 Bam-I (FIG. 6F) yields the final product, pPGPK-C1 E1 (FIG. 6G). The C-1 derived sequence in plasmid pGPGK-C1 E1 ends at the BamHI site corresponding to nucleotide 3599 in the C-1 genomic sequence, which is 90 bp downstream of the end of the E1B coding region. This expression plasmid contains from about nucleotide 548 to about nucleotide 3581 of SEQ ID NO: 1 which encodes E1a and E1b of Ad C1 under the control of the PGK promoter.

EXAMPLE 4

Generation of Cell Lines Expressing Chimpanzee Adenovirus E1 Proteins

Cell lines expressing viral E1 proteins were generated by transfecting HeLa (ATCC Acc. No. CCL2) and A549 (ATCC Acc. No. CCL185) cell lines with either pGPGK-C1 E1 or pGPGK-68 E1 of Example 3. These cell lines are necessary for the production of E1 deleted recombinant chimpanzee adenoviruses by co-transfection of genomic viral DNA and the expression plasmids described above. Transfection of these cell lines, as well as isolation and purification of recombinant chimpanzee adenoviruses therefrom were performed by methods conventional for other adenoviruses, i.e., human adenoviruses [see, e.g., Horwitz, cited above and other standard texts].

A. Cell lines expressing C1 and C68 E1 proteins

HeLa and A549 cells in 10 cm dishes were transfected with 10 µg of pGPGK-C1-E1 DNA or pGPGK-C68-E1 DNA using a Cellphect™ kit (Pharmacia, Uppsala, Sweden) and following the manufacturer's protocol. 22 hours post-transfection, the cells were subjected to a three minute glycerol shock (15% glycerol in Hepes Buffered Saline, pH 7.5) washed once in DMEM (HeLa) or F12K (A549; Life Technologies, Inc., Grand Island, N.Y.) media supplemented with 10% FCS, 1% Pen-Strep, then incubated for six hours at 37° C. in the above described media. The transfected cells were then split into duplicate 15 cm plates at ratios of 1:20, 1:40, 1:80, 1:160, and 1:320. Following incubation at 37° C. overnight, the media was supplemented with G418 (Life Technologies, Inc.) at a concentration of 1 µg/ml. The media was replaced every 5 days and clones were isolated 20 days post-transfection.

Thirty-two A549 and 16 HeLa C1 E1 cell clones and 40 A549 and 37 HeLa C68 E1 cell clones were isolated and assayed for their ability to augment adeno-associated virus (AAV) infection and expression of recombinant LacZ protein as described below.

B. AAV Augmentation Assay for Screening E1 Expressing Cell Lines

AAV requires adenovirus-encoded proteins in order to complete its life cycle. The adenoviral E1 proteins as well as the E4 region encoded ORF-6 protein are necessary for the augmentation of AAV infection. A novel assay for E1 expression based on AAV augmentation is disclosed herein. Briefly, the method for identifying adenoviral E1-expressing cells comprises the steps of infecting in separate cultures a putative adenovirus E1-expressing cell and a cell containing no adenovirus sequence, with both an adeno-associated virus (AAV) expressing a marker gene and an AAV expressing the ORF6 of the E4 gene of human adenovirus, for a suitable time. The marker gene activity in the resulting cells is measured and those cells with significantly greater measurable marker activity than the control cells are selected as confirmed E1-expressing cells. In the following experiment, the marker gene is a lacZ gene and the marker activity is the appearance of blue stain.

For example, the cell lines described above, as well as untransfected control cells (A549 and HeLa) are infected with 100 genomes per cell of an AAV vector bearing a marker gene, e.g., AV.LacZ [K. Fisher et al., *J. Virol.*, 70:520 (1996)] and an AAV vector expressing the ORF6 region of human Ad5 (AV.orf6) (see SEQ ID NO: 3). The DNA sequence [SEQ ID NO: 3] of the plasmid pAV.CMVALP.GRE-ORF6, also called AV.orf6, generates a novel recombinant adeno-associated virus (rAAV) containing the LacZ transgene and the Ad E4 ORF 6, which is an open reading frame whose expression product facilitates single-stranded (ss) to double-stranded (ds) conversion of rAAV genomic DNA. In SEQ ID NO: 3, the AAV 5' inverted terminal repeat (ITR) is at nucleotides 53–219; the cytomegalovirus (CMV) enhancer/promoter is at nucleotides 255–848; the human placenta alkaline phosphatase cDNA (ALP) is at nucleotides 914–2892; the SV40 polyadenylation (polyA) signal is at nucleotides 2893–3090; the glucocorticoid dependent (GRE) promoter is at nucleotides 3114–3393; the Ad5 E4-ORF6 cDNA is at nucleotides 3402–4286; the SV40 polyA signal is at nucleotides 4315–4512; and the 3' AAV ITR is at nucleotides 4547–4713. All other nucleotides are plasmid-derived. These vectors are incubated in medium containing 2% FCS and 1% Pen-Strep at 37° C. for 4 hours, at which point an equal volume of medium containing 10% FCS is added. It should be understood by one of skill in the art that any marker gene (or reporter gene) may be employed in the first AAV vector of this assay, e.g., alkaline phosphatase, luciferase, and others. An antibody-enzyme assay can also be used to quantitate levels of antigen, where the marker expresses an antigen. The assay is not limited by the identity of the marker gene. Twenty to twenty-four hours post-infection, the cells are stained for LacZ activity using standard methods. After 4 hours the cells are observed microscopically and cell lines with significantly more blue cells than the A549 or HeLa cell controls are scored as positive.

Eight A549 (A-2,3,8,13,15,18,23,38) and five HeLa (H-3, 4,15,16,20) cell clones are significantly positive in the AAV augmentation assay and the three best of each cell type (A-18, A-23, A-13 and H-16, H-4, H-20), when tested, support the growth of E1 deleted recombinant C68 viruses.

Four A549 (A-3, 6, 19, 22) and nine HeLa (H-2,5–7, 11–16) cell clones are significantly positive in the AAV augmentation assay and the three best of each cell type (A-3, A-19, A-22 and H-5, H-12, H-14), when tested, support the growth of E1 deleted recombinant C1 viruses.

EXAMPLE 5

Generation of Recombinant Chimpanzee Adenoviruses

Recombinant chimpanzee adenovirus vectors are prepared using the C1 and C68 sequences described herein and HEK293 cells. The cell lines described in Example 4 may also be used similarly. Plasmids used to construct C68 and C1 recombinant adenovirus vectors are illustrated in FIGS. 7A through 7K, and 8A through 8K, respectively. See also FIGS. 11A–11K.

A. pC1-CMV-LacZ pSP72 (Promega, Madison, Wis.) is modified by digestion with BglII, followed by filling-in of the ends with Klenow and ligation with a synthetic 12 bp PacI linker (New England Biolabs, Beverly, Mass.) to yield pSP72-Pac (FIG. 7A), which contains a large multiple cloning site with conventional restriction enzyme cleavage sites.

pSP72-Pac is digested with PacI and EcoRV and ligated with the 465 bp PacI-SnaBI fragment isolated from pBSC1-BamG (FIG. 7B) to yield pSP-C1-MU 0–1.3 (FIG. 7C). The CMV promoter-driven LacZ gene is isolated from pCMV-β (Clontech, Palo Alto, Calif.; FIG. 7D) as a 4.5kb EcoRI/SalI fragment and ligated with similarly digested pSP-C1-MU 0–1.3 DNA to yield pSP-C1-MU 0–1.3-CMV-β.

For the initial step in the isolation of the C1 Ad map units 9–16 region, pGEM-3Z (Promega, Madison, Wis.; FIG. 7F) and pBS-C1-BamI (FIG. 7G) are digested with BamHI and SphI and the 310 bp fragment from pBS-C1-BamI is ligated with the pGEM-3Z backbone to form pGEM-C1-MU9–10 (FIG. 7H). C1 map units 10–17 are isolated from pBS-C1 BamE (FIG. 7I) by digestion with BamHI. The 2.5 kb fragment is ligated with BamHI-digested pGEM-C1-MU9–10 to form pGEM-C1-MU9–17 (FIG. 7J). The 2.9 kb fragment containing C1 map unit 9–17 region is isolated from pGEM-C1-MU9–17 by digestion with HindIII and ligated with pSP-C1-MU 0–1.3-β (FIG. 7E) digested with HindIII to form the final plasmid, pC1-CMV-LacZ (FIG. 7K).

pC1-CMV-LacZ (FIG. 7K) thus contains C1 Ad mu 0 to 1.3, followed by the CMV promoter, an SD/SA, the LacZ gene, a SV40 poly A sequence and C1 Ad mu. 9–17, as well as additional plasmid sequence. This plasmid is co-transfected into the E1-expressing cell line with a left terminal clipped C1 Ad fragment (or a replication-defective C1 Ad helper virus) to produce by homologous recombination a recombinant chimpanzee adenovirus carrying the LacZ gene.

C. pC68-CMV-LacZ pSP72-Pac (FIG. 8A; also FIG. 7A) is digested with PacI and EcoRV and ligated with the 465 bp PacI-SnaBI fragment isolated from pBS-C68-BamE (FIG. 8B) to yield pSP-C68-MU 0–1.3 (FIG. 8C). As above, the CMV promoter-driven LacZ gene is isolated from pCMVβ (Clontech; FIG. 8D; also FIG. 7D) as a 4.5kb EcoRI-SalI fragment and ligated with similarly digested pSP-C68-MU 0–1.3 DNA to yield pSP-C68-MU 0–1.3-CMVβ (FIG. 8E).

For the initial step in the isolation of the map unit 9–16 region of C68, pGEM-3Z (FIG. 8F; also FIG. 7F) and pBS-C68-BamF (FIG. 8G) are double digested with BamHI and SphI and the 293 bp fragment from pBS-C68-BamF is ligated with the pGEM-3Z backbone to form pGEM-C68-MU9–10 (FIG. 8H). C68 map units 10–16.7 are isolated from pBS-C68 BamB (FIG. 8I) by digestion with XbaI, followed by filling in of the ends and digestion with BamHI. The 2.4 kb fragment is ligated with BamHI/EcoRV-digested pGEM-C68-MU9–10 to form pGEM-C68-MU9–16.7 (FIG. 8J). The C68 map unit 9–16.7 region is isolated from pGEM-C68-MU9–16 by digestion with EcoRI, filling in of the ends with Klenow and then digestion with HindIII. The 2.7 kb fragment is ligated with pSP-C68-MU 0–1.3-CMVβ (FIG. 8E), digested with HindIII and PvuII to form the final plasmid, pC68-CMV-LacZ (FIG. 8K).

pC68-CMV-LacZ (FIG. 8K) thus contains C68 Ad mu 0 to 1.3, followed by the CMV promoter, an SD/SA, the LacZ gene, a SV40 poly A sequence and C68 Ad mu 9–16.7, as well as additional plasmid sequence. This plasmid is co-transfected into the E1-expressing cell line with another C68 Ad to produce by homologous recombination a recombinant chimpanzee adenovirus carrying the LacZ gene.

D. pBS-Notx2

The LacZ gene is removed from either pC1-CMV-LacZ (FIG. 7K) or pC68-CMV-LacZ (FIG. 8K) by digestion with NotI, and replaced by the coding sequence of any desired gene. This cloning step is facilitated by having the gene of interest flanked by NotI restriction sites, preferably with the upstream site in the 5' untranslated region of the gene.

Figure 4A:
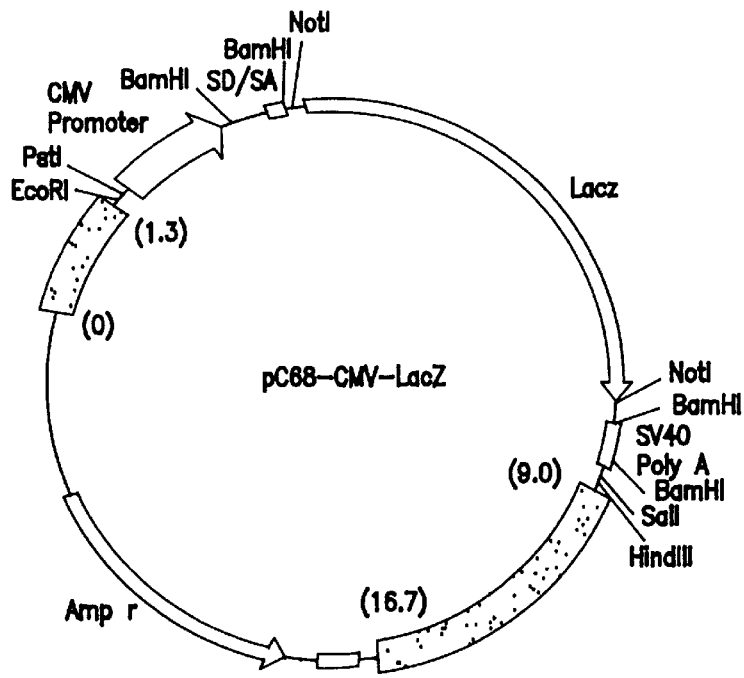
FIG. 4A is a more detailed schematic drawing of pC68-CMV-LacZ.
Figure 4B:
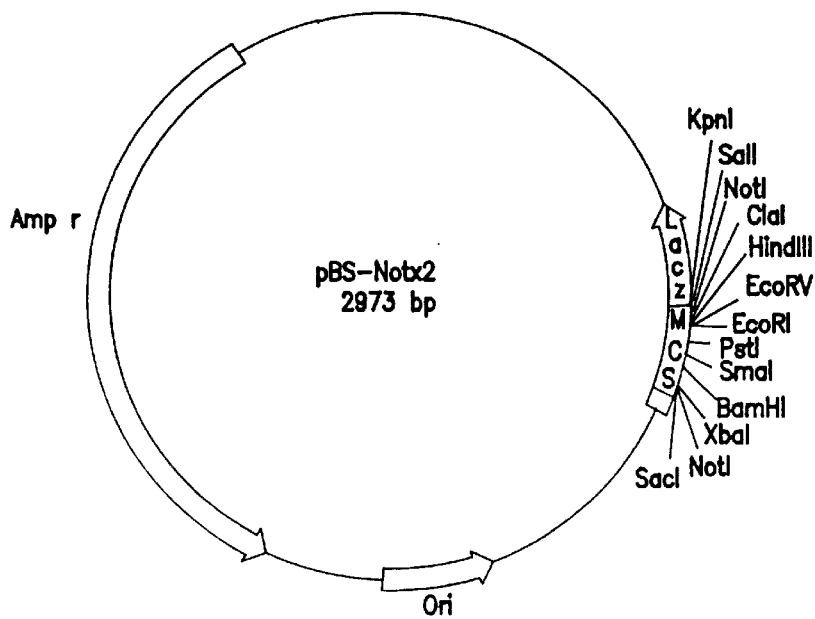
FIG. 4B is a schematic representation of pBS-Notx2.

Such a cloning vector is derived from pBluescript SK+ (Stratagene, La Jolla, Calif.) by digestion of SK+ with SalI, followed by filling in of the ends and ligation with a synthetic 8 bp NotI linker (New England Biolabs, Beverly, Mass.):
GCGGCCGC.
CGCCGGCG The resulting pBS-Notx2 shuttle vector (FIG. 4B) is thus designed to facilitate cloning of cDNAs into pC1-CMV-LacZ (FIG. 7K) and pC68-CMV-LacZ (FIG. 8K; see also FIG. 4A) as a NotI fragment. pBS-Notx2 has two NotI sites flanking a number of restriction sites suitable for cloning the cDNA to be expressed in the recombinant adenoviruses and the LacZ ORF from pBluescript is maintained, allowing blue/white screening of clones in pBS-Notx2.

E. Homologous Recombination with Helper Virus

To generate the recombinant adenoviruses from the plasmids described above, the appropriate E1-expressing packaging cell line, such as 293 cell line or a cell line of Example 4, is co-transfected with a replication defective C1 or C68 helper virus, or a left-end clipped C1 or C68 fragment, as appropriate. These helper viruses may be deleted of other non-essential genes. The infected cell line is subsequently transfected with an adenovirus vector as described above bearing the transgene of interest. Homologous recombination occurs between the helper and the plasmid, which permits the adenovirus-transgene sequences in the vector to be replicated and packaged into virion capsids, resulting in the recombinant adenovirus.

Transfection is followed by an agar overlay for 2 weeks, after which the viruses are plaqued, expanded and screened for expression of the transgene. See, for example, FIGS. 10A–10D. Several additional rounds of plaque purification are followed by another expansion of the cultures. Finally the cells are harvested, a virus extract prepared and the recombinant chimpanzee adenovirus containing the desired transgene is purified by buoyant density ultracentrifugation in a CsCl gradient. All of the above procedures are known to those of skill in the art.

F. Another C1 Recombinant Adenovirus

Another set of plasmids used to construct a C1 recombinant adenovirus is described as follows. FIGS. 11A–11H illustrate the scheme employed to generate a unique restriction site in the left end of the C1 genome. A unique site is necessary in the procedure employed in generating a recombinant adenovirus, but C1 has no such site. There are two Spe-I restriction sites, including one at position 1733, within the E1B 21K coding region. To replace this Spe-I site with a unique Not-I site, plasmid pNEB-C1-BamG (FIG. 11A), containing the left end of the C1 genome, was digested with Spe-I and Asc-I, and ligated to the 6204 bp Spe-I/Asc-I fragment from the C1 genome (FIG. 11B). The resulting plasmid, pNEB-C1-AscI-B (FIG. 11C) is then digested with Spe-I, filled in with Klenow enzyme and ligated to the synthetic 8 bp Not-I linker (FIG. 11D) described above, to yield pNEB-C1-AscI-B-NotI (FIG. 11E).

This plasmid is digested with Pac-I and Asc-I and the purified fragment is ligated overnight with the C1-Asc-I-A fragment (FIG. 11G). The ligation reaction is extracted with phenol:chloroform:iso-amyl alcohol, then chloroform, and then 3 µg of sheared salmon sperm DNA is added and the DNA is ethanol precipitated. The resuspended DNA is used to transfect 293 cells and DNA from viral plaques is tested for a Not-I site (11H).

G. GFP as a Transgene

Plasmids used to construct exemplary C68 expression plasmids containing the bacterial green fluorescent protein (GFP) gene are illustrated in FIGS. 9A through 9G, respectively. To facilitate the cloning of the GFP gene into the chimp Adeno expression vectors, pEGFP-1 (FIG. 9A, Clonetech, Palo Alto, Calif.) was digested with Sma-I and ligated to the previously described 8 bp Not-I linker (FIG. 9B). The resulting plasmid, pEGFP-Notx2 (FIG. 9C) has the GFP gene flanked by Not-I sites.

The purified pEGFP-Notx2 Not-I fragment is ligated to Not-I digested pC1-CMV-LacZ (FIGS. 7K and 9D) or pC68-CMV-LacZ (FIGS. 8K and 9E) to yield the GFP expression vectors pC1-CMV-GFP (FIG. 9F) and pC68-CMV-GFP (FIG. 9G and FIG. 10A), respectively.

EXAMPLE 6

Delivery of Transgene to Host Cell

The resulting recombinant chimpanzee adenovirus described in Example 5 above is then employed to deliver the transgene to a mammalian, preferably human, cell. For example, following purification of the recombinant C68-CMV-GFP virus of Example 5G, human embryonic kidney 293 cells and A549 cells were infected at an MOI of 50 particles per cell. GFP expression was documented 24 hours post-infection.

In vivo studies have tested the infectivity of the virus in murine liver (tail vein injection), lung (intratracheal injection) and muscle (intramuscular injection). Preliminary data indicate that the C68-CMV-GFP recombinant virus transduces all three tissues, and GFP expression can be detected.

When administered in vivo, a less severe immune response is produced by the human immune system (which is naive to the chimpanzee adenovirus sequences) than to a human adenovirus construct, thereby permitting subsequent administration of the same or another vector.

All references recited above are incorporated herein by reference. Numerous modifications and variations of the present invention are included in the scope of the above-identified specification and are expected to be obvious to one of skill in the art. Such modifications and alterations to the compositions and processes of the present invention, such as selections of different minigenes or selection or dosage of the vectors or immune modulators are believed to be within the scope of the claims appended hereto.

What is claimed is:

1. A non-simian mammalian cell that expresses a chimpanzee adenovirus gene obtained from the sequence of SEQ ID NO: 1.

2. The cell according to claim 1 wherein said gene is selected from the group consisting of the adenovirus E1A, E1B, E2A, E2B, E3, E4, L1, L2, L3, L4 and L5 of SEQ ID NO: 1.

3. A nucleic acid molecule comprising a chimpanzee adenovirus DNA sequence comprising a gene obtained from the sequence of SEQ ID NO: 1.

4. The nucleic acid molecule according to claim 3, wherein said gene is selected from the group consisting of said chimpanzee adenovirus E1A, E1B, E2A, E2B, E3, E4, L1, L2, L3, L4 and L5 genes.

5. The molecule according to claim 3 which is SEQ ID NO: 1.

6. The molecule according to claim 3, wherein said chimpanzee DNA sequence is SEQ ID NO: 1, lacking at least one gene selected from the group consisting of E1A, E1B, E2A, E2B, E3, E4, L1, L2, L3, L4 and L5 genes.

7. A vector comprising a chimpanzee adenovirus DNA sequence obtained from SEQ ID NO: 1 and a selected heterologous gene operatively linked to regulatory sequences which direct expression of said gene in a heterologous host cell wherein said chimpanzee adenovirus DNA sequence comprises at least the cis-elements necessary for replication and virion encapsidation, said cis-elements flanking said selected heterologous gene and regulatory sequences.

8. The vector according to claim 7, wherein said chimpanzee adenovirus DNA sequence comprises a gene selected from the group consisting of E1A, E1B, E2A, E2B, E3, E4, L1, L2, L3, L4 and L5 gene sequences of SEQ ID NO: 1.

9. The vector according to claim 7 wherein said chimpanzee adenovirus DNA sequence is the sequence of SEQ ID NO: 1 lacking at least one gene sequence selected from the group consisting of E1A, E1B, E2A, E2B, E3, E4, L1, L2, L3, L4 and L5 gene sequences of SEQ ID NO: 1.

10. A host cell comprising the vector of claim 7.

11. A human cell that expresses a selected gene introduced therein through introduction of the vector of claim 7 into said cell.

12. A method for delivering a heterologous gene to a mammalian cell comprising introducing into said cell an effective amount of the vector of claim 7.

13. A method for producing a selected gene product comprising introducing the vector of claim 7 into a mammalian cell, culturing said cell under suitable conditions and isolating and recovering from said cell culture the expressed gene product.

14. The vector according to claim 9, wherein the gene sequence which is lacking is the E1A gene sequence.

15. The vector according to claim 9 wherein the gene sequence which is lacking is the E1B gene sequence.

16. A non-simian mammalian cell that expresses a chimpanzee adenovirus gene obtained from the sequence of SEQ ID NO: 2.

17. The cell according to claim 16 wherein said gene is selected from the group consisting of the adenovirus E1A, E1B, E2A, E2B, E3, E4, L1, L2, L3, L4 and L5 of SEQ ID NO: 2.

18. A nucleic acid molecule comprising a chimpanzee adenovirus DNA sequence comprising a gene obtained from the sequence of SEQ ID NO: 2.

19. The nucleic acid molecule according to claim 18, wherein said gene is selected from the group consisting of said chimpanzee adenovirus E1A, E1B, E2A, E2B, E3, E4, L1, L2, L3, L4 and L5 genes.

20. The molecule according to claim 18 which is SEQ ID NO: 2.

21. The molecule according to claim 18, wherein said chimpanzee DNA sequence is SEQ ID NO: 2, lacking at least one gene selected from the group consisting of E1A, E1B, E2A, E2B, E3, E4, L1, L2, L3, L4 and L5 genes.

22. A vector comprising a chimpanzee adenovirus DNA sequence obtained from SEQ ID NO: 2 and a selected heterologous gene operatively linked to regulatory sequences which direct expression of said gene in a heterologous host cell wherein said chimpanzee adenovirus DNA sequence comprises at least the cis-elements necessary for replication and virion encapsidation, said cis-elements flanking said selected heterologous gene and regulatory sequences.

23. The vector according to claim 22, wherein said chimpanzee adenovirus DNA sequence comprises a gene selected from the group consisting of E1A, E1B, E2A, E2B, E3, E4, L1, L2, L3, L4 and L5 gene sequences of SEQ ID NO: 2.

24. The vector according to claim 22 wherein said chimpanzee adenovirus DNA sequence is the sequence of SEQ ID NO: 2 lacking at least one gene sequence selected from the group consisting of said E1A, E1B, E2A, E2B, E3, E4, L1, L2, L3, L4 and L5 gene sequences of SEQ ID NO: 1.

25. A host cell transfected with the vector of claim 22.

26. A human cell that expresses a selected gene introduced therein through introduction of the vector of claim 22 into the cell.

27. A method for delivering a heterologous gene to a mammalian cell comprising introducing into said cell an effective amount of the vector of claim 22.

28. A method for producing a selected gene product comprising introducing the vector or claim 22 into a mammalian cell, culturing said cell under suitable conditions and isolating and recovering from said cell culture the expressed gene product.

29. The vector according to claim 24, wherein the gene sequence which is lacking is the E1A gene sequence.

30. The vector according to claim 24 wherein the gene sequence which is lacking is the E1B gene sequence.

* * * * *